(12) United States Patent
Hinuma et al.

(10) Patent No.: US 7,354,726 B2
(45) Date of Patent: Apr. 8, 2008

(54) SCREENING METHOD

(75) Inventors: Syuji Hinuma, Ibaraki (JP); Ryo Fujii, Ibaraki (JP); Yuji Kawamata, Ibaraki (JP); Masanori Miwa, Osaka (JP); Masaki Hosoya, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 196 days.

(21) Appl. No.: 10/474,481

(22) PCT Filed: Apr. 11, 2002

(86) PCT No.: PCT/JP02/03613

§ 371 (c)(1),
(2), (4) Date: Oct. 8, 2003

(87) PCT Pub. No.: WO02/084286

PCT Pub. Date: Oct. 24, 2002

(65) Prior Publication Data
US 2004/0171067 A1 Sep. 2, 2004

(30) Foreign Application Priority Data

| Apr. 12, 2001 | (JP) | ............................. 2001-114203 |
| Jun. 14, 2001 | (JP) | ............................. 2001-180562 |
| Jul. 16, 2001 | (JP) | ............................. 2001-214922 |
| Dec. 27, 2001 | (JP) | ............................. 2001-397767 |
| Feb. 22, 2002 | (JP) | ............................. 2002-45728 |

(51) Int. Cl.
*C07K 14/705* (2006.01)
*C12N 15/12* (2006.01)
*G01N 33/566* (2006.01)

(52) U.S. Cl. ................. 435/7.21; 435/69.1; 435/252.3; 435/320.1; 436/501; 530/350; 536/23.5

(58) Field of Classification Search ..................... None
See application file for complete search history.

(56) References Cited

U.S. PATENT DOCUMENTS

| 6,255,059 B1 | 7/2001 | Klein et al. ................. 435/7.31 |
| 2001/0026926 A1 | 10/2001 | Klein et al. ................. 435/7.31 |
| 2004/0086898 A1 | 5/2004 | Maruyama et al. |

FOREIGN PATENT DOCUMENTS

| WO | WO99/47647 | 9/1999 |
| WO | WO99/66041 | 12/1999 |
| WO | WO 00/031261 | 6/2000 |
| WO | WO 01/36481 A1 | 5/2001 |
| WO | WO 01/77325 A1 | 10/2001 |
| WO | WO 02/40669 A1 | 5/2002 |

OTHER PUBLICATIONS

M Gräler et al., *Genomics*, vol. 53, pp. 164-169 (1998).
L. Rydelek et al., *Analytical Biochemistry*, vol. 275, pp. 54-61 (1999).
W. Chen et al., *Analytical Biochemistry* vol. 226, pp. 349-354 (1995).
C. Stratowa et al., *Current Opinion In Biotechnology*, vol. 6, pp. 574-581 (1995).

*Primary Examiner*—John Ulm
(74) *Attorney, Agent, or Firm*—David G. Conlin; Christine C. O'Day; Edwards Angell Palmer & Dodge LLP

(57) ABSTRACT

The present invention intends to provide a screening of agonist/antagonist and the like. Specifically, the invention provides a method of screening a compound or its salt that alters the binding property between a novel G protein-coupled receptor protein or its salt, and a substance relating to cholesterol metabolism, which comprises using the receptor protein or its salt, which contains the same or substantially the same amino acid sequence as the amino acid sequence represented by SEQ ID NO: 1, SEQ ID NO: 5, SEQ ID NO: 7, SEQ ID NO: 14 or SEQ ID NO: 16, and the substance relating to cholesterol metabolism.

2 Claims, 30 Drawing Sheets

Fig.1

```
              9            18           27           36           45           54
ATG ACG CCC AAC AGC ACT GGC GAG GTG CCC AGC CCC ATT CCC AAG GGG GCT TTG
--- --- --- --- --- --- --- --- --- --- --- --- --- --- --- --- --- ---
 M   T   P   N   S   T   G   E   V   P   S   P   I   P   K   G   A   L 63           72           81           90           99          108
GGG CTC TCC CTG GCC CTG GCA AGC CTC ATC ATC ACC GCG AAC CTG CTC CTA GCC
--- --- --- --- --- --- --- --- --- --- --- --- --- --- --- --- --- ---
 G   L   S   L   A   L   A   S   L   I   I   T   A   N   L   L   L   A 117          126          135          144          153          162
CTG GGC ATC GCC TGG GAC CGC CGC CTG CGC AGC CCA CCT GCT GGC TGC TTC TTC
--- --- --- --- --- --- --- --- --- --- --- --- --- --- --- --- --- ---
 L   G   I   A   W   D   R   R   L   R   S   P   P   A   G   C   F   F 171          180          189          198          207          216
CTG AGC CTA CTG CTG GCT GGG CTG CTC ACG GGT CTG GCA TTG CCC ACA TTG CCA
--- --- --- --- --- --- --- --- --- --- --- --- --- --- --- --- --- ---
 L   S   L   L   L   A   G   L   L   T   G   L   A   L   P   T   L   P 225          234          243          252          261          270
GGG CTG TGG AAC CAG AGT CGC CGG GGT TAC TGG TCC TGC CTC CTC GTC TAC TTG
--- --- --- --- --- --- --- --- --- --- --- --- --- --- --- --- --- ---
 G   L   W   N   Q   S   R   R   G   Y   W   S   C   L   L   V   Y   L
```

Fig. 2

```
        279         288         297         306         315         324
GCT CCC AAC TTC TCC TTC CTC TCC CTG CTT GCC AAC CTC TTG CTG GTG CAC GGG
--- --- --- --- --- --- --- --- --- --- --- --- --- --- --- --- --- ---
 A   P   N   F   S   F   L   S   L   L   A   N   L   L   L   V   H   G 333         342         351         360         369         378
GAG CGC TAC ATG GCA GTC CTG AGG CCA CTC CAG CCC CCT GGG AGC ATT CGG CTG
--- --- --- --- --- --- --- --- --- --- --- --- --- --- --- --- --- ---
 E   R   Y   M   A   V   L   R   P   L   Q   P   P   G   S   I   R   L 387         396         405         414         423         432
GCC CTG CTC CTC ACC TGG GCT GGT CCC CTG CTC TTT GCC AGT CTG CCC GCT CTG
--- --- --- --- --- --- --- --- --- --- --- --- --- --- --- --- --- ---
 A   L   L   L   T   W   A   G   P   L   L   F   A   S   L   P   A   L 441         450         459         468         477         486
GGG TGG AAC CAC TGG ACC CCT GGT GCC AAC TGC AGC TCC CAG GCT ATC TTC CCA
--- --- --- --- --- --- --- --- --- --- --- --- --- --- --- --- --- ---
 G   W   N   H   W   T   P   G   A   N   C   S   S   Q   A   I   F   P 495         504         513         522         531         540
GCC CCC TAC CTG TAC CTC GAA GTC TAT GGG CTC CTG CTG CCC GCC GTG GGT GCT
--- --- --- --- --- --- --- --- --- --- --- --- --- --- --- --- --- ---
 A   P   Y   L   Y   L   E   V   Y   G   L   L   L   P   A   V   G   A
```

Fig. 3

```
     549         558         567         576         585         594
GCT GCC TTC CTC TCT GTC CGC GTG CTG GCC ACT GCC CAC CGC CAG CTG CAG GAC
--- --- --- --- --- --- --- --- --- --- --- --- --- --- --- --- --- ---
 A   A   F   L   S   V   R   V   L   A   T   A   H   R   Q   L   Q   D 603         612         621         630         639         648
ATC TGC CGG CTG GAG CGG GCA GTG TGC CGC GAT GAG CCC TCC GCC CTG GCC CGG
--- --- --- --- --- --- --- --- --- --- --- --- --- --- --- --- --- ---
 I   C   R   L   E   R   A   V   C   R   D   E   P   S   A   L   A   R 657         666         675         684         693         702
GCC CTT ACC TGG AGG CAG GCA AGG GCA CAG GCT GGA GCC ATG CTG CTC TTC GGG
--- --- --- --- --- --- --- --- --- --- --- --- --- --- --- --- --- ---
 A   L   T   W   R   Q   A   R   A   Q   A   G   A   M   L   L   F   G 711         720         729         738         747         756
CTG TGC TGG GGG CCC TAC GTG GCC ACA CTG CTC CTC TCA GTC CTG GCC TAT GAG
--- --- --- --- --- --- --- --- --- --- --- --- --- --- --- --- --- ---
 L   C   W   G   P   Y   V   A   T   L   L   L   S   V   L   A   Y   E 765         774         783         792         801         810
CAG CGC CCG CCA CTG GGG CCT GGG ACA CTG TTG TCC CTC CTC TCC CTA GGA AGT
--- --- --- --- --- --- --- --- --- --- --- --- --- --- --- --- --- ---
 Q   R   P   P   L   G   P   G   T   L   L   S   L   L   S   L   G   S
```

Fig. 4

```
        819         828         837         846         855         864
GCC AGT GCA GCG GCA GTG CCC GTA GCC ATG GGG CTG GGC GAT CAG CGC TAC ACA
--- --- --- --- --- --- --- --- --- --- --- --- --- --- --- --- --- ---
 A   S   A   A   A   V   P   V   A   M   G   L   G   D   Q   R   Y   T 873         882         891         900         909         918
GCC CCC TGG AGG GCA GCC GCC CAA AGG TGC CTG CAG GGG CTG TGG GGA AGA GCC
--- --- --- --- --- --- --- --- --- --- --- --- --- --- --- --- --- ---
 A   P   W   R   A   A   A   Q   R   C   L   Q   G   L   W   G   R   A 927         936         945         954         963         972
TCC CGG GAC AGT CCC GGC CCC AGC ATT GCC TAC CAC CCA AGC AGC CAA AGC AGT
--- --- --- --- --- --- --- --- --- --- --- --- --- --- --- --- --- ---
 S   R   D   S   P   G   P   S   I   A   Y   H   P   S   S   Q   S   S 981         990
GTC GAC CTG GAC TTG AAC TAA
--- --- --- --- --- --- ---
 V   D   L   D   L   N   *
```

Fig.6
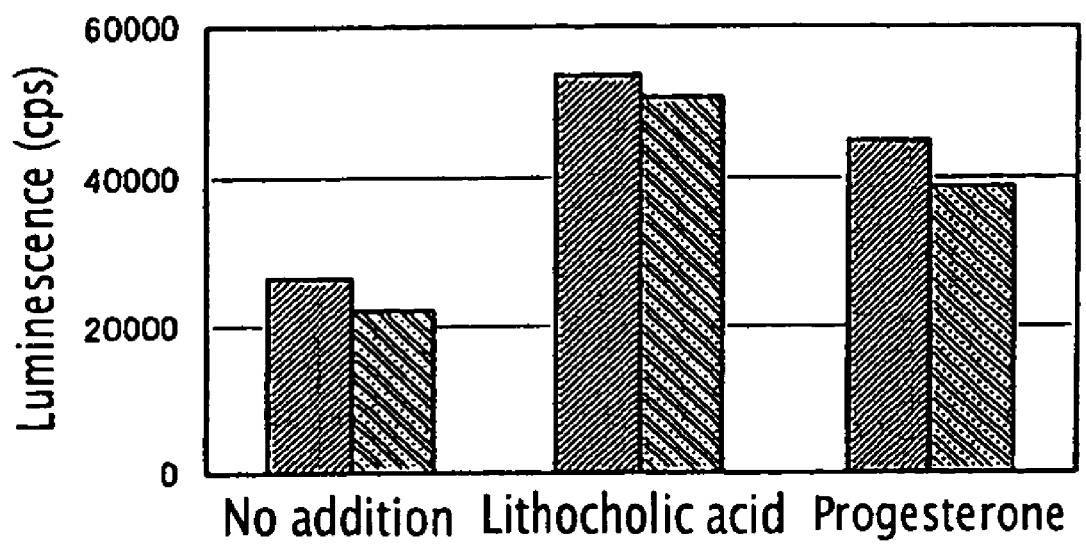
A
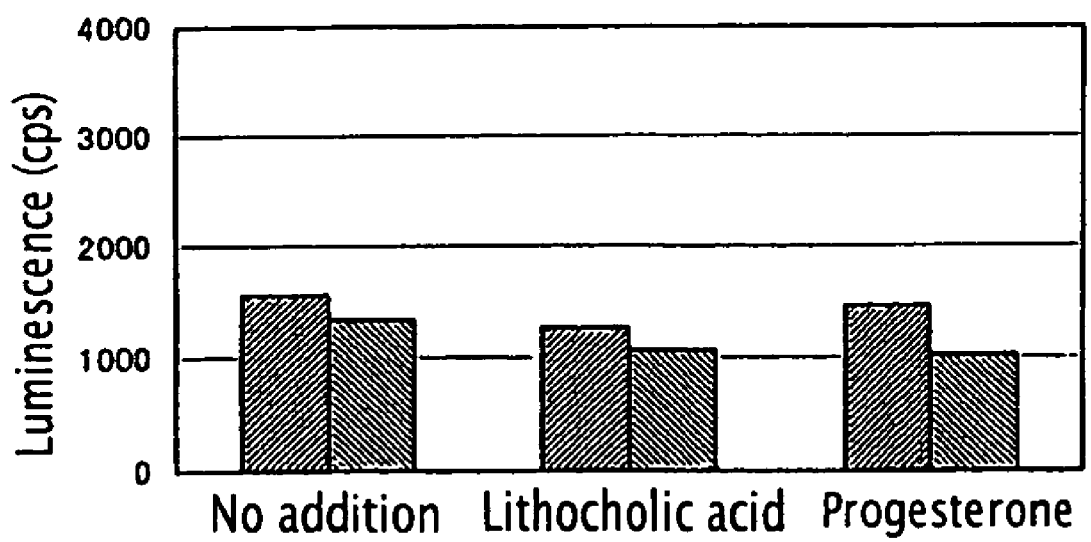
B

Fig. 28

DNA sequence

```
atggcccggt ccgcgacact ggcggccgcc gccctggcgc tgtgcctgct gctggcgccg    60
cctggcctcg cgtggtacaa gccagcggcg gggcacagct cctactcggt gggccgcgcc   120
gcggggctgc tgtccggcct ccgcaggtcc ccgtacgcgc ggcgctccca gccctacaga   180
ggggcggaac ccccgggcgg ggccggcgcc tccccggagc tgcaactgca ccccaggctg   240
cggagcctcg ctgtgtgcgt ccaggacgtc gccccaaacc tgcagaggtg cgagcggctc   300
cccgacggcc gcgggaccta ccagtgcaag gcgaacgtct tcctgtccct gcgcgcagcc   360
gactgcctcg ccgcct                                                   378
```

Fig. 29

Amino acid sequence

Met Ala Arg Ser Ala Thr Leu Ala Ala Ala Ala Leu Ala Leu Cys Leu
                    5               10              15
Leu Leu Ala Pro Pro Gly Leu Ala Trp Tyr Lys Pro Ala Ala Gly His
            20              25              30
Ser Ser Tyr Ser Val Gly Arg Ala Ala Gly Leu Leu Ser Gly Leu Arg
        35              40              45
Arg Ser Pro Tyr Ala Arg Arg Ser Gln Pro Tyr Arg Gly Ala Glu Pro
    50              55              60
Pro Gly Gly Ala Gly Ala Ser Pro Glu Leu Gln Leu His Pro Arg Leu
65              70              75              80
Arg Ser Leu Ala Val Cys Val Gln Asp Val Ala Pro Asn Leu Gln Arg
                85              90              95
Cys Glu Arg Leu Pro Asp Gly Arg Gly Thr Tyr Gln Cys Lys Ala Asn
            100             105             110
Val Phe Leu Ser Leu Arg Ala Ala Asp Cys Leu Ala Ala End
        115             120             125

SEQUENCE LISTING

```
<160> NUMBER OF SEQ ID NOS: 43

<210> SEQ ID NO 1
<211> LENGTH: 330
<212> TYPE: PRT
<213> ORGANISM: Homo sapiens

<400> SEQUENCE: 1

Met Thr Pro Asn Ser Thr Gly Glu Val Pro Ser Pro Ile Pro Lys Gly
                 5                  10                  15

Ala Leu Gly Leu Ser Leu Ala Leu Ala Ser Leu Ile Ile Thr Ala Asn
             20                  25                  30

Leu Leu Leu Ala Leu Gly Ile Ala Trp Asp Arg Arg Leu Arg Ser Pro
         35                  40                  45

Pro Ala Gly Cys Phe Phe Leu Ser Leu Leu Leu Ala Gly Leu Leu Thr
     50                  55                  60

Gly Leu Ala Leu Pro Thr Leu Pro Gly Leu Trp Asn Gln Ser Arg Arg
 65                  70                  75                  80

Gly Tyr Trp Ser Cys Leu Leu Val Tyr Leu Ala Pro Asn Phe Ser Phe
                 85                  90                  95

Leu Ser Leu Leu Ala Asn Leu Leu Leu Val His Gly Glu Arg Tyr Met
            100                 105                 110

Ala Val Leu Arg Pro Leu Gln Pro Pro Gly Ser Ile Arg Leu Ala Leu
        115                 120                 125

Leu Leu Thr Trp Ala Gly Pro Leu Leu Phe Ala Ser Leu Pro Ala Leu
    130                 135                 140

Gly Trp Asn His Trp Thr Pro Gly Ala Asn Cys Ser Ser Gln Ala Ile
145                 150                 155                 160

Phe Pro Ala Pro Tyr Leu Tyr Leu Glu Val Tyr Gly Leu Leu Leu Pro
                165                 170                 175

Ala Val Gly Ala Ala Ala Phe Leu Ser Val Arg Val Leu Ala Thr Ala
            180                 185                 190

His Arg Gln Leu Gln Asp Ile Cys Arg Leu Glu Arg Ala Val Cys Arg
        195                 200                 205

Asp Glu Pro Ser Ala Leu Ala Arg Ala Leu Thr Trp Arg Gln Ala Arg
    210                 215                 220

Ala Gln Ala Gly Ala Met Leu Leu Phe Gly Leu Cys Trp Gly Pro Tyr
225                 230                 235                 240

Val Ala Thr Leu Leu Leu Ser Val Leu Ala Tyr Glu Gln Arg Pro Pro
                245                 250                 255
```

-continued

```
Leu Gly Pro Gly Thr Leu Leu Ser Leu Leu Ser Leu Gly Ser Ala Ser
            260                 265                 270

Ala Ala Ala Val Pro Val Ala Met Gly Leu Gly Asp Gln Arg Tyr Thr
        275                 280                 285

Ala Pro Tyr Arg Ala Ala Gln Arg Cys Leu Gln Gly Leu Trp Gly
    290                 295                 300

Arg Ala Ser Arg Asp Ser Pro Gly Ser Ile Ala Tyr His Pro Ser
305                 310                 315                 320

Ser Gln Ser Ser Val Asp Leu Asp Leu Asn
                325                 330

<210> SEQ ID NO 2
<211> LENGTH: 993
<212> TYPE: DNA
<213> ORGANISM: Homo sapiens
<220> FEATURE:
<221> NAME/KEY: CDS
<222> LOCATION: (1)..(987)

<400> SEQUENCE: 2
```

| | |
|---|---|
| atg acg ccc aac agc act ggc gag gtg ccc agc ccc att ccc aag ggg<br>Met Thr Pro Asn Ser Thr Gly Glu Val Pro Ser Pro Ile Pro Lys Gly<br>1                     5                    10                 15 | 48 |
| gct ttg ggg ctc tcc ctg gcc ctg gca agc ctc atc atc acc gcg aac<br>Ala Leu Gly Leu Ser Leu Ala Leu Ala Ser Leu Ile Ile Thr Ala Asn<br>              20                    25                    30 | 96 |
| ctc ctc cta gcc ctg ggc atc gcc tgg gac cgc cgc ctg cgc agc cca<br>Leu Leu Leu Ala Leu Gly Ile Ala Trp Asp Arg Arg Leu Arg Ser Pro<br>        35                    40                    45 | 144 |
| cct gct ggc tgc ttc ttc ctg agc cta ctg ctg gct ggg ctg ctc acg<br>Pro Ala Gly Cys Phe Phe Leu Ser Leu Leu Leu Ala Gly Leu Leu Thr<br>    50                    55                    60 | 192 |
| ggt ctg gca ttg ccc aca ttg cca ggg ctg tgg aac cag agt cgc cgg<br>Gly Leu Ala Leu Pro Thr Leu Pro Gly Leu Trp Asn Gln Ser Arg Arg<br>65                     70                    75                    80 | 240 |
| ggt tac tgg tcc tgc ctc ctc gtc tac ttg gct ccc aac ttc tcc ttc<br>Gly Tyr Trp Ser Cys Leu Leu Val Tyr Leu Ala Pro Asn Phe Ser Phe<br>                  85                    90                    95 | 288 |
| ctc tcc ctg ctt gcc aac ctc ttg ctg gtg cac ggg gag cgc tac atg<br>Leu Ser Leu Leu Ala Asn Leu Leu Leu Val His Gly Glu Arg Tyr Met<br>              100                  105                 110 | 336 |
| gca gtc ctg agg cca ctc cag ccc cct ggg agc att cgg ctg gcc ctg<br>Ala Val Leu Arg Pro Leu Gln Pro Pro Gly Ser Ile Arg Leu Ala Leu<br>        115                    120                    125 | 384 |
| ctc ctc acc tgg gct ggt ccc ctg ctc ttt gcc agt ctg ccc gct ctg<br>Leu Leu Thr Trp Ala Gly Pro Leu Leu Phe Ala Ser Leu Pro Ala Leu<br>    130                    135                    140 | 432 |
| ggg tgg aac cac tgg acc cct ggt gcc aac tgc agc tcc cag gct atc<br>Gly Trp Asn His Trp Thr Pro Gly Ala Asn Cys Ser Ser Gln Ala Ile<br>145                    150                    155                    160 | 480 |
| ttc cca gcc ccc tac ctg tac ctc gaa gtc tat ggg ctc ctg ctg ccc<br>Phe Pro Ala Pro Tyr Leu Tyr Leu Glu Val Tyr Gly Leu Leu Leu Pro<br>              165                  170                 175 | 528 |
| gcc gtg ggt gct gct gcc ttc ctc tct gtc cgc gtg ctg gcc act gcc<br>Ala Val Gly Ala Ala Ala Phe Leu Ser Val Arg Val Leu Ala Thr Ala<br>        180                    185                    190 | 576 |
| cac cgc cag ctg cag gac atc tgc cgg ctg gag cgg gca gtg tgc cgc<br>His Arg Gln Leu Gln Asp Ile Cys Arg Leu Glu Arg Ala Val Cys Arg<br>    195                    200                    205 | 624 |

```
gat gag ccc tcc gcc ctg gcc cgg gcc ctt acc tgg agg cag gca agg    672
Asp Glu Pro Ser Ala Leu Ala Arg Ala Leu Thr Trp Arg Gln Ala Arg
    210                 215                 220 gca cag gct gga gcc atg ctg ctc ttc ggg ctg tgc tgg ggg ccc tac    720
Ala Gln Ala Gly Ala Met Leu Leu Phe Gly Leu Cys Trp Gly Pro Tyr
225                 230                 235                 240 gtg gcc aca ctg ctc ctc tca gtc ctg gcc tat gag cag cgc ccg cca    768
Val Ala Thr Leu Leu Leu Ser Val Leu Ala Tyr Glu Gln Arg Pro Pro
                245                 250                 255 ctg ggg cct ggg aca ctg ttg tcc ctc ctc tcc cta gga agt gcc agt    816
Leu Gly Pro Gly Thr Leu Leu Ser Leu Leu Ser Leu Gly Ser Ala Ser
            260                 265                 270 gca gcg gca gtg ccc gta gcc atg ggg ctg ggc gat cag cgc tac aca    864
Ala Ala Ala Val Pro Val Ala Met Gly Leu Gly Asp Gln Arg Tyr Thr
        275                 280                 285 gcc ccc tgg agg gca gcc gcc caa agg tgc ctg cag ggg ctg tgg gga    912
Ala Pro Trp Arg Ala Ala Ala Gln Arg Cys Leu Gln Gly Leu Trp Gly
    290                 295                 300 aga gcc tcc cgg gac agt ccc ggc ccc agc att gcc tac cac cca agc    960
Arg Ala Ser Arg Asp Ser Pro Gly Pro Ser Ile Ala Tyr His Pro Ser
305                 310                 315                 320 agc caa agc agt gtc gac ctg gac ttg aac taa                        993
Ser Gln Ser Ser Val Asp Leu Asp Leu Asn
                325                 330

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Designed
      oligonucleotide primer to amplify DNA encoding TGR5

<400> SEQUENCE: 3
gatgacgccc aacagcactg gcgaggtgcc                                   30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Designed
      oligonucleotide primer to amplify DNA encoding TGR5

<400> SEQUENCE: 4
ttagttcaag tccaggtcga cactgctttg g                                 31

<210> SEQ ID NO 5
<211> LENGTH: 329
<212> TYPE: PRT
<213> ORGANISM: Mus musculus

<400> SEQUENCE: 5

Met Met Thr Pro Asn Ser Thr Glu Leu Ser Ala Ile Pro Met Gly Val
                5                   10                  15

Leu Gly Leu Ser Leu Ala Leu Ala Ser Leu Ile Val Ile Ala Asn Leu
            20                  25                  30

Leu Leu Ala Leu Gly Ile Ala Leu Asp Arg His Leu Arg Ser Pro Pro
        35                  40                  45

Ala Gly Cys Phe Phe Leu Ser Leu Leu Leu Ala Gly Leu Leu Thr Gly
    50                  55                  60
```

```
Leu Ala Leu Pro Met Leu Pro Gly Leu Trp Ser Arg Asn His Gln Gly
 65                  70                  75                  80

Tyr Trp Ser Cys Leu Leu His Leu Thr Pro Asn Phe Cys Phe Leu
                 85                  90                  95

Ser Leu Leu Ala Asn Leu Leu Leu Val His Gly Glu Arg Tyr Met Ala
                100                 105                 110

Val Leu Gln Pro Leu Arg Pro His Gly Ser Val Arg Leu Ala Leu Phe
            115                 120                 125

Leu Thr Trp Val Ser Ser Leu Phe Phe Ala Ser Leu Pro Ala Leu Gly
    130                 135                 140

Trp Asn His Trp Ser Pro Asp Ala Asn Cys Ser Ser Gln Ala Val Phe
145                 150                 155                 160

Pro Ala Pro Tyr Leu Tyr Leu Glu Val Tyr Gly Leu Leu Leu Pro Ala
                165                 170                 175

Val Gly Ala Thr Ala Leu Leu Ser Val Arg Val Leu Ala Thr Ala His
            180                 185                 190

Arg Gln Leu Cys Glu Ile Arg Arg Leu Glu Arg Ala Val Cys Arg Asp
        195                 200                 205

Val Pro Ser Thr Leu Ala Arg Ala Leu Thr Trp Arg Gln Ala Arg Ala
210                 215                 220

Gln Ala Gly Ala Thr Leu Leu Phe Leu Leu Cys Trp Gly Pro Tyr Val
225                 230                 235                 240

Ala Thr Leu Leu Leu Ser Val Leu Ala Tyr Glu Arg Arg Pro Pro Leu
                245                 250                 255

Gly Pro Gly Thr Leu Leu Ser Leu Ile Ser Leu Gly Ser Thr Ser Ala
            260                 265                 270

Ala Ala Val Pro Val Ala Met Gly Leu Gly Asp Gln Arg Tyr Thr Ala
        275                 280                 285

Pro Trp Arg Thr Ala Ala Gln Arg Cys Leu Arg Val Leu Arg Gly Arg
    290                 295                 300

Ala Lys Arg Asp Asn Pro Gly Pro Ser Thr Ala Tyr His Thr Ser Ser
305                 310                 315                 320

Gln Cys Ser Ile Asp Leu Asp Leu Asn
                325
```

<210> SEQ ID NO 6
<211> LENGTH: 990
<212> TYPE: DNA
<213> ORGANISM: Mus musculus

<400> SEQUENCE: 6

```
atgatgacac ccaacagcac tgagctgtcg gccattccca tgggggttct ggggctttcc      60
ttggccctgg caagcctcat cgtcatcgcc aacctgctcc tggccctagg catcgccctg     120
gaccgccact gcgcagccc acctgctggc tgcttcttcc taagcctact actagccggg     180
ctgctcacag ggctggcact gcccatgctg cctgggctat ggagccggaa ccatcagggc     240
tactggtcct gctccttct ccacttgacc cccaactttt gtttcctttc cctgcttgcc     300
aatctgctgc tggtgcatgg ggaacgctac atggcagtgt tgcagccact ccggccccat     360
ggaagtgtgc ggctagccct gttcctcacc tgggtcagct ccctgttctt tgccagcctg     420
cctgctctgg gctggaacca ttggagccct gatgccaact gcagctccca agctgtcttc     480
ccagcccct acctctacct ggaagtttat ggcctcctgt tgcctgccgt ggggccact     540
gcccttctct ctgtccgcgt gttggccact gcccaccgcc agctgtgtga gatccgccga     600
```

```
ctggagcggg cagtgtgccg cgatgtaccc tcaaccctgg ctagggctct cacctggagg      660
caggctaggg cacaggcagg agccacactg ctcttcttgc tgtgttgggg ccctatgtg       720 gccacattgc tcctgtcagt cttggcctat gagcgtcgcc caccactagg gcctggaact      780
ctgttatcgc tcatctcatt gggcagcacc agtgctgccg ctgtgcctgt ggccatgggg      840
ctgggtgatc agcgctacac agccccctgg aggacagctg cccaaaggtg tctacgagtg      900
cttcgaggaa gagccaagag ggacaatcca ggccccagca ctgcctacca caccagtagc      960
caatgcagca ttgacctgga cttgaattag                                       990
```

```
<210> SEQ ID NO 7
<211> LENGTH: 329
<212> TYPE: PRT
<213> ORGANISM: Rattus sp.

<400> SEQUENCE: 7
```

Met Met Ser His Asn Thr Thr Glu Leu Ser Ala Ile Pro Arg Gly Val
                 5                  10                  15

Gln Glu Leu Ser Leu Val Leu Ala Ser Leu Ile Val Ile Ala Asn Leu
             20                  25                  30

Leu Leu Ala Leu Gly Ile Val Leu Asp Arg His Leu Arg Ser Pro Pro
         35                  40                  45

Ala Gly Cys Phe Phe Leu Ser Leu Leu Ala Gly Leu Leu Thr Gly
     50                  55                  60

Leu Ala Leu Pro Thr Leu Pro Gly Leu Trp Asn Arg Ser His Gln Gly
 65                  70                  75                  80

Tyr Trp Ser Cys Leu Leu His Leu Ala Pro Asn Phe Cys Phe Leu
                 85                  90                  95

Ser Leu Leu Ala Asn Leu Leu Val His Gly Glu Arg Tyr Met Ala
            100                 105                 110

Val Leu Gln Pro Leu Arg Pro His Gly Ser Val Arg Leu Ala Leu Phe
            115                 120                 125

Leu Thr Trp Ile Ser Ser Leu Leu Phe Ala Ser Leu Pro Ala Leu Gly
        130                 135                 140

Trp Asn His Trp Ser Pro Gly Ala Asn Cys Ser Ser Gln Ala Ile Phe
145                 150                 155                 160

Pro Ala Pro Tyr Leu Tyr Leu Glu Val Tyr Gly Leu Leu Leu Pro Ala
                165                 170                 175

Val Gly Ala Thr Ala Leu Leu Ser Val Arg Val Leu Ala Thr Ala His
            180                 185                 190

His Gln Leu Arg Glu Ile Arg Arg Leu Glu Arg Ala Val Cys Arg Asp
        195                 200                 205

Ala Pro Ser Thr Leu Ala Arg Ala Leu Thr Trp Arg Gln Ala Arg Ala
    210                 215                 220

Gln Ala Gly Ala Thr Leu Leu Phe Leu Leu Cys Trp Gly Pro Tyr Val
225                 230                 235                 240

Ala Thr Leu Leu Leu Ser Val Leu Ala Tyr Glu Arg Arg Pro Pro Leu
                245                 250                 255

Gly Pro Val Thr Leu Leu Ser Leu Ile Ser Leu Gly Ser Ala Ser Ala
            260                 265                 270

Ala Val Pro Val Ala Met Gly Leu Gly Asp Gln Arg Tyr Thr Ala
        275                 280                 285

Pro Trp Arg Thr Ala Ala Gln Arg Trp Leu Gln Val Leu Arg Gly Arg
    290                 295                 300

Pro Lys Arg Ala Asn Pro Gly Pro Ser Thr Ala Tyr His Ser Ser Ser
305                 310                 315                 320

Gln Cys Ser Thr Asp Leu Asp Leu Asn
                325

<210> SEQ ID NO 8
<211> LENGTH: 990
<212> TYPE: DNA
<213> ORGANISM: Rattus sp.

<400> SEQUENCE: 8

| | | |
|---|---|---|
| atgatgtcac acaacaccac tgagctgtca gccattccca gaggggttca ggagctttcc | 60 |
| ctggtcctgg caagcctcat cgtcatcgcc aacctgctcc tggccctagg cattgtcctg | 120 |
| gaccgccact acgcagccca acctgctggc tgcttctttc taagcctact actagctggg | 180 |
| ctactcacag ggttggcact gcccacgctg cctgggctat ggaataggag ccatcagggg | 240 |
| tactggtcct gcctccttct ccacttggcc cccaactttt gtttcctctc cctgcttgcc | 300 |
| aatctgctgc tggtgcatgg ggaacgctac atggcagtgt tgcagccact ccggccccat | 360 |
| gggagtgtgc ggctagccct gttcctcacc tggatcagct ccctgctctt tgccagcctg | 420 |
| cctgctctgg gctggaacca ctggagtcct ggtgccaact gcagctccca ggctatcttc | 480 |
| ccagccccct acctttacct cgaagtctat gggctcctgc tgcccgctgt gggggccact | 540 |
| gcccttctct ctgtccgagt gttggccact gcccaccacc agctgcggga gatccgcaga | 600 |
| ctggagcggg cggtgtgccg tgatgcaccc tcaaccctag cgagggctct cacctggagg | 660 |
| caggctaggg cacaggcagg agccacactg ctcttttgc tgtgttgggg gccctatgtg | 720 |
| gccacattgc tcctgtcagt cttggcctat gagcggcggc caccactagg gcctgtaact | 780 |
| ctgttatctc tcatctcatt gggcagtgcc agtgctgcag ttgtgcctgt ggccatgggt | 840 |
| ctgggtgatc agcgctacac ggcccccctgg aggacagctg cccaaaggtg gctacaagtg | 900 |
| cttcgaggaa gacccaagag ggccaatcca ggccccagca ctgcctacca ctccagtagc | 960 |
| caatgcagca ctgacttgga cttgaattag | 990 |

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer 1 used in Example 5

<400> SEQUENCE: 9
aaagtcgacc catgatgaca cccaacagca c                                31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer 2 used in Example 5

<400> SEQUENCE: 10
aaaactagtc ctaattcaag tccaggtcaa t                                31

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
     primer 3 used in Example 5

<400> SEQUENCE: 11
aaagtcgacc atgatgtcac aca                                           23

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
     primer 4 used in Example 5

<400> SEQUENCE: 12
aaaactagtc ctaattcaag tccaagtcag tgc                                33

<210> SEQ ID NO 13
<211> LENGTH: 990
<212> TYPE: DNA
<213> ORGANISM: Bos sp.

<400> SEQUENCE: 13
atgacatcca acagcaccag ggaggtgccc agccccgttc ctgcaggggc cctggggctc    60
tccctggccc tggcaagcct catcgtcgct gccaacctgc tcctggccgt gggtatcgcc   120
ggggaccgcc gcctgcgcag cccgcccgct ggctgcttct tcctgagtct tctgctggca   180
gggctgctca cggggctggc gctgcccgcg ctgcccgtcc tatggagcca gagccgccgg   240
ggctactggt cctgcctctt cctctacttg gctcccaact tctgcttcct ctccctgctc   300
gccaacctcc tactggtgca cggggagcgc tacatggccg tgctgcggcc cctgcggccc   360
cgtgggagca tgcggctggc cctgctcctc acctgggctg ccccttgct ctttgccagc    420 ctgcctgccc tgggctggaa ccactgggcc cctggtggca actgcagctc ccaggccgtc   480
ttcccagccc cctacctcta cctcgaaatc tatgggctcc tgctgccggc tgtgggcgcg   540
gccgccctcc tctcggtccg cgtgctggtc actgcgcacc gccagctgca ggacatccgc   600
cggctggagc gggccgtgtg ccgcggggcg ccctcggccc tggcccgagc cctcacctgg   660
cggcaggcca gggcgcaggc tggggccacg ttgctctttg gctgtgtgct ggggccctac   720
gtggccaccc tgctgctctc tgtcctggcc tttgagcagc gcccgccact agggcccgga   780
actctgctgt ccctcatctc actgggcagc gccagtgcgg cggccgtgcc cgtggccatg   840
gggctgggtg atcagcgcta cagggcccc tggagggtgg ccgcccagaa gtggctccgg    900
atgctgcggg gcagaccgca gagcagtcct ggtcccagca ccgcctacca taccagcagc   960
caaagcagcg tggaccttga cttgaactag                                     990

<210> SEQ ID NO 14
<211> LENGTH: 329
<212> TYPE: PRT
<213> ORGANISM: Bos sp.

<400> SEQUENCE: 14

Met Thr Ser Asn Ser Thr Arg Glu Val Pro Ser Pro Val Pro Ala Gly
                5                   10                  15

Ala Leu Gly Leu Ser Leu Ala Leu Ala Ser Leu Ile Val Ala Ala Asn
            20                  25                  30

Leu Leu Leu Ala Val Gly Ile Ala Gly Asp Arg Arg Leu Arg Ser Pro
        35                  40                  45

```
Pro Ala Gly Cys Phe Phe Leu Ser Leu Leu Leu Ala Gly Leu Leu Thr
     50                  55                  60
Gly Leu Ala Leu Pro Ala Leu Pro Val Leu Trp Ser Gln Ser Arg Arg
 65                  70                  75                  80
Gly Tyr Trp Ser Cys Leu Phe Leu Tyr Leu Ala Pro Asn Phe Cys Phe
                 85                  90                  95
Leu Ser Leu Leu Ala Asn Leu Leu Val His Gly Glu Arg Tyr Met
            100                 105                 110
Ala Val Leu Arg Pro Leu Arg Pro Arg Gly Ser Met Arg Leu Ala Leu
            115                 120                 125
Leu Leu Thr Trp Ala Ala Pro Leu Leu Phe Ala Ser Leu Pro Ala Leu
        130                 135                 140
Gly Trp Asn His Trp Ala Pro Gly Gly Asn Cys Ser Ser Gln Ala Val
145                 150                 155                 160
Phe Pro Ala Pro Tyr Leu Tyr Leu Glu Ile Tyr Gly Leu Leu Leu Pro
                165                 170                 175
Ala Val Gly Ala Ala Ala Leu Leu Ser Val Arg Val Leu Val Thr Ala
            180                 185                 190
His Arg Gln Leu Gln Asp Ile Arg Arg Leu Glu Arg Ala Val Cys Arg
        195                 200                 205
Gly Ala Pro Ser Ala Leu Ala Arg Ala Leu Thr Trp Arg Gln Ala Arg
210                 215                 220
Ala Gln Ala Gly Ala Thr Leu Leu Phe Gly Leu Cys Trp Gly Pro Tyr
225                 230                 235                 240
Val Ala Thr Leu Leu Leu Ser Val Leu Ala Phe Glu Gln Arg Pro Pro
                245                 250                 255
Leu Gly Pro Gly Thr Leu Leu Ser Leu Ile Ser Leu Gly Ser Ala Ser
            260                 265                 270
Ala Ala Ala Val Pro Val Ala Met Gly Leu Gly Asp Gln Arg Tyr Thr
        275                 280                 285
Gly Pro Trp Arg Val Ala Ala Gln Lys Trp Leu Arg Met Leu Arg Gly
290                 295                 300
Arg Pro Gln Ser Ser Pro Gly Pro Ser Thr Ala Tyr His Thr Ser Ser
305                 310                 315                 320
Gln Ser Ser Val Asp Leu Asp Leu Asn
                325

<210> SEQ ID NO 15
<211> LENGTH: 993
<212> TYPE: DNA
<213> ORGANISM: Oryctolagus cuniculus

<400> SEQUENCE: 15
atgacaccca acagcaccgg ggaggtgcct ggccccatcc ccaggggcgc cctggagctg      60
tcactggccc tggcaagcct catcatcgca gccaacctgc tcctggcgct gggcatcgcc     120
tgcgaccgcc gccttcgcag cccaccggcc ggctgcttct tcctgagcct gttgctggcc     180
gggctgctta cggggctggc actgcccact ctgccagggc tctggagaca gagccaccgg     240
ggctattggt cctgcctgct cgtctacttg gctcccaact tctccttcct ctccctgctc     300
gccaacctcc tgctggtgca cggggagcgc tatgtggcgg tgctgcggcc actccagcct     360
ccggggagca tccggctggc cctgctcctc acctggaccg gccccctgct ctttgccagc     420
ctgccggccc tgggctggaa ccactggggc cctgaggcca actgcagctc ccagaccatc     480
```

-continued

```
ttcccagcgc cctacctcta cctcgaagtc tacgggctcc tgctgccggc cgtgggggcc      540
gcggcccttc tctcggctca cgtgctgctg ccgcccacc gccagctgca ggacatccgc       600
cggctggagc gggccgtgtg ccgcgacgcg ccctccgccc tggcccgggc ccttacctgg      660
aggcaggcgc gggcgcaggc tggagccacg ctgctctttg gctgtgctg ggggccctat       720 gtggccacgc tgttcctgtc ggtcctggcc tatgagcagc gcccacctct agggcccgga     780
actctgctgt ctctcctctc cctgggcagt gccagcgcgg cggccgtgcc cgtggccatg     840 ggctgggtg atcaccgcta cacagcgccc tggagggcgg ccgcccggag gtggctgcgg      900
gggctgcggg ggagaggctc ccaggctagc cctggcccca gcactgccta ccacaccagc    960
agccaaagca gcgtggacgt ggacttgaac tga                                  993
```

<210> SEQ ID NO 16
<211> LENGTH: 330
<212> TYPE: PRT
<213> ORGANISM: Oryctolagus cuniculus

<400> SEQUENCE: 16

```
Met Thr Pro Asn Ser Thr Gly Glu Val Pro Gly Pro Ile Pro Arg Gly
                 5                  10                  15

Ala Leu Glu Leu Ser Leu Ala Leu Ala Ser Leu Ile Ile Ala Ala Asn
            20                  25                  30

Leu Leu Leu Ala Leu Gly Ile Ala Cys Asp Arg Arg Leu Arg Ser Pro
        35                  40                  45

Pro Ala Gly Cys Phe Phe Leu Ser Leu Leu Leu Ala Gly Leu Leu Thr
    50                  55                  60

Gly Leu Ala Leu Pro Thr Leu Pro Gly Leu Trp Arg Gln Ser His Arg
65                  70                  75                  80

Gly Tyr Trp Ser Cys Leu Leu Val Tyr Leu Ala Pro Asn Phe Ser Phe
                85                  90                  95

Leu Ser Leu Leu Ala Asn Leu Leu Val His Gly Glu Arg Tyr Val
            100                 105                 110

Ala Val Leu Arg Pro Leu Gln Pro Pro Gly Ser Ile Arg Leu Ala Leu
        115                 120                 125

Leu Leu Thr Trp Thr Gly Pro Leu Leu Phe Ala Ser Leu Pro Ala Leu
    130                 135                 140

Gly Trp Asn His Trp Gly Pro Glu Ala Asn Cys Ser Ser Gln Thr Ile
145                 150                 155                 160

Phe Pro Ala Pro Tyr Leu Tyr Leu Glu Val Tyr Gly Leu Leu Leu Pro
                165                 170                 175

Ala Val Gly Ala Ala Ala Leu Leu Ser Ala His Val Leu Leu Ala Ala
            180                 185                 190

His Arg Gln Leu Gln Asp Ile Arg Arg Leu Glu Arg Ala Val Cys Arg
        195                 200                 205

Asp Ala Pro Ser Ala Leu Ala Arg Ala Leu Thr Trp Arg Gln Ala Arg
    210                 215                 220

Ala Gln Ala Gly Ala Thr Leu Leu Phe Gly Leu Cys Trp Gly Pro Tyr
225                 230                 235                 240

Val Ala Thr Leu Phe Leu Ser Val Leu Ala Tyr Glu Gln Arg Pro Pro
                245                 250                 255

Leu Gly Pro Gly Thr Leu Leu Ser Leu Leu Ser Leu Gly Ser Ala Ser
            260                 265                 270

Ala Ala Ala Val Pro Val Ala Met Gly Leu Gly Asp His Arg Tyr Thr
        275                 280                 285
```

```
Ala Pro Trp Arg Ala Ala Arg Arg Trp Leu Arg Gly Leu Arg Gly
    290                 295                 300

Arg Gly Ser Gln Ala Ser Pro Gly Pro Ser Thr Ala Tyr His Thr Ser
305                 310                 315                 320

Ser Gln Ser Ser Val Asp Val Asp Leu Asn
                325                 330

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      bF primer

<400> SEQUENCE: 17
gtcgacatga catccaacag caccagggag gtg                                33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      bR primer

<400> SEQUENCE: 18
gctagcctag ttcaagtcaa ggtccacgct gct                                33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      rabbitF primer

<400> SEQUENCE: 19
gtcgacatga cacccaacag caccggggag gtg                                33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      rabbitR primer

<400> SEQUENCE: 20
actagttcag ttcaagtcca cgtccacgct gct                                33

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer designed for IL-1 alfa mRNA quantification

<400> SEQUENCE: 21
gaagatgaac ctgtgctgct a                                             21

<210> SEQ ID NO 22
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer designed for IL-1 alfa mRNA quantification

<400> SEQUENCE: 22
tcactctcgc tgtctgtgat g                                            21

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      probe designed for IL-1 alfa mRNA quantification, labeled
      5'-terminal with FAM and 3'-terminal with TAMRA

<400> SEQUENCE: 23
aggaaatgcc tgagacaccc agga                                         24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer designed for IL-1 beta mRNA quantification

<400> SEQUENCE: 24
gcacgtatga gctgaaagct                                              20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer designed for IL-1 beta mRNA quantification

<400> SEQUENCE: 25
actcatggag aacaccactt gt                                           22

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Probe
      designed for IL-1 beta mRNA quantification, labeled 5'-terminal
      with FAM and 3'-terminal with TAMRA

<400> SEQUENCE: 26
tccacctcaa tgcagagaat ctga                                         24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer designed for IL-6 mRNA quantification

<400> SEQUENCE: 27
agcatcctgg agaccatcaa g                                            21

<210> SEQ ID NO 28
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer designed for IL-6 mRNA quantification

<400> SEQUENCE: 28
cctttctgtt catgcagttg ac                                              22

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Probe
      designed for IL-6 mRNA quantification, labeled 5'-terminal with
      FAM and 3'-terminal with TAMRA

<400> SEQUENCE: 29
agctgaggaa agagatgtgt gaccatga                                        28

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer designed for IL-8 mRNA quantification

<400> SEQUENCE: 30
ctctttgtga agctgcagtt ct                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer designed for IL-8 mRNA quantification

<400> SEQUENCE: 31
ggtgtggagt gtgtctttat gc                                              22

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Probe
      designed for IL-8 mRNA quantification, labeled 5'-terminal with
      FAM and 3'-terminal with TAMRA

<400> SEQUENCE: 32
cacggattgg tacagagctt cgatgc                                          26

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer designed for TNF alfa mRNA quantification

<400> SEQUENCE: 33
tcaccctcag atcagcttct c                                               21

<210> SEQ ID NO 34
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer designed for TNF alfa mRNA quantification

<400> SEQUENCE: 34
tggttgtccg tgagcttca                                                  19

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Probe
      designed for TNF alfa mRNA quantification, labeled 5'-terminal
      with FAM and 3'-terminal with TAMRA

<400> SEQUENCE: 35
cgtagtagca aacccgcaag tgga                                            24

<210> SEQ ID NO 36
<211> LENGTH: 125
<212> TYPE: PRT
<213> ORGANISM: Homo sapiens

<400> SEQUENCE: 36

Met Ala Arg Ser Ala Thr Leu Ala Ala Ala Leu Ala Leu Cys Leu
                 5                  10                  15

Leu Leu Ala Pro Pro Gly Leu Ala Trp Tyr Lys Pro Ala Ala Gly His
             20                  25                  30

Ser Ser Tyr Ser Val Gly Arg Ala Ala Gly Leu Leu Ser Gly Leu Arg
         35                  40                  45

Arg Ser Pro Tyr Ala Arg Arg Ser Gln Pro Tyr Arg Gly Ala Glu Pro
     50                  55                  60

Pro Gly Gly Ala Gly Ala Ser Pro Glu Leu Gln Leu His Pro Arg Leu
 65                  70                  75                  80

Arg Ser Leu Ala Val Cys Val Gln Asp Val Ala Pro Asn Leu Gln Arg
                 85                  90                  95

Cys Glu Arg Leu Pro Asp Gly Arg Gly Thr Tyr Gln Cys Lys Ala Asn
                100                 105                 110

Val Phe Leu Ser Leu Arg Ala Ala Asp Cys Leu Ala Ala
            115                 120                 125

<210> SEQ ID NO 37
<211> LENGTH: 376
<212> TYPE: DNA
<213> ORGANISM: Homo sapiens

<400> SEQUENCE: 37
atggcccggt ccgcgacact ggcggccgcc gccctggcgc tgtgcctgct gctggcgccg     60
cctggcctcg cgtggtacaa gccagcggcg gggcacagct cctactcggt gggccgcgcc    120
gcggggctgc tgtccggcct ccgcaggtcc cgtacgcgc ggcgctccca gccctacaga    180
ggggcggaac cccgggcgg ggccggcgcc tccccggagc tgcaactgca ccccaggctg    240
cggagcctcg ctgtgtgcgt ccaggacgtc gccccaaacc tgcagaggtg cgagcggctc    300
cccgacggcc gcgggaccta ccagtgcaag gcgaacgtct tcctgtccct gcgcgcagcc    360
gactgcctcg ccgcct                                                    376
```

```
<210> SEQ ID NO 38
<211> LENGTH: 328
<212> TYPE: PRT
<213> ORGANISM: Homo sapiens

<400> SEQUENCE: 38

Met Asp Asn Ala Ser Phe Ser Glu Pro Trp Pro Ala Asn Ala Ser Gly
1               5                   10                  15

Pro Asp Pro Ala Leu Ser Cys Ser Asn Ala Ser Thr Leu Ala Pro Leu
                20                  25                  30

Pro Ala Pro Leu Ala Val Ala Val Pro Val Val Tyr Ala Val Ile Cys
            35                  40                  45

Ala Val Gly Leu Ala Gly Asn Ser Ala Val Leu Tyr Val Leu Leu Arg
        50                  55                  60

Ala Pro Arg Met Lys Thr Val Thr Asn Leu Phe Ile Leu Asn Leu Ala
65                  70                  75                  80

Ile Ala Asp Glu Leu Phe Thr Leu Val Leu Pro Ile Asn Ile Ala Asp
                85                  90                  95

Phe Leu Leu Arg Gln Trp Pro Phe Gly Glu Leu Met Cys Lys Leu Ile
            100                 105                 110

Val Ala Ile Asp Gln Tyr Asn Thr Phe Ser Ser Leu Tyr Phe Leu Thr
        115                 120                 125

Val Met Ser Ala Asp Arg Tyr Leu Val Val Leu Ala Thr Ala Glu Ser
130                 135                 140

Arg Arg Val Ala Gly Arg Thr Tyr Ser Ala Ala Arg Ala Val Ser Leu
145                 150                 155                 160

Ala Val Trp Gly Ile Val Thr Leu Val Val Leu Pro Phe Ala Val Phe
                165                 170                 175

Ala Arg Leu Asp Asp Glu Gln Gly Arg Arg Gln Cys Val Leu Val Phe
            180                 185                 190

Pro Gln Pro Glu Ala Phe Trp Trp Arg Ala Ser Arg Leu Tyr Thr Leu
        195                 200                 205

Val Leu Gly Phe Ala Ile Pro Val Ser Thr Ile Cys Val Leu Tyr Thr
210                 215                 220

Thr Leu Leu Cys Arg Leu His Ala Met Arg Leu Asp Ser His Ala Lys
225                 230                 235                 240

Ala Leu Glu Arg Ala Lys Lys Arg Val Thr Phe Leu Val Val Ala Ile
                245                 250                 255

Leu Ala Val Cys Leu Leu Cys Trp Thr Pro Tyr His Leu Ser Thr Val
            260                 265                 270

Val Ala Leu Thr Thr Asp Leu Pro Gln Thr Pro Leu Val Ile Ala Ile
        275                 280                 285

Ser Tyr Phe Ile Thr Ser Leu Ser Tyr Ala Asn Ser Cys Leu Asn Pro
290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325         328

<210> SEQ ID NO 39
<211> LENGTH: 1000
<212> TYPE: DNA
<213> ORGANISM: Homo sapiens

<400> SEQUENCE: 39
```

```
atcgatatgg acaacgcctc gttctcggag ccctggcccg ccaacgcatc gggcccggac    60
ccggcgctga gctgctccaa cgcgtcgact ctggcgccgc tgccggcgcc gctggcggtg   120
gctgtaccag ttgtctacgc ggtgatctgc gccgtgggtc tggcgggcaa ctccgccgtg   180
ctgtacgtgt tgctgcgggc gccccgcatg aagaccgtca ccaacctgtt catcctcaac   240
ctggccatcg ccgacgagct cttcacgctg gtgctgccca tcaacatcgc cgacttcctg   300
ctgcggcagt ggcccttcgg ggagctcatg tgcaagctca tcgtggctat cgaccagtac   360
aacaccttct ccagcctcta cttcctcacc gtcatgagcg ccgaccgcta cctggtggtg   420
ttggccactg cggagtcgcg ccgggtggcc ggccgcacct acagccgcg cgcgcggtg    480 agcctggccg tgtgggggat cgtcacactc gtcgtgctgc ccttcgcagt cttcgcccgg   540
ctagacgacg agcagggccg cgccagtgc gtgctagtct ttccgcagcc cgaggccttc   600
tggtggcgcg cgagccgcct ctacacgctc gtgctgggct cgccatccc cgtgtccacc   660 atctgtgtcc tctataccac cctgctgtgc cggctgcatg ccatgcgct ggacagccac   720 gccaaggccc tggagcgcgc caagaagcgg gtgaccttcc tggtggtggc aatcctggcg   780
gtgtgcctcc tctgctggac gccctaccac ctgagcaccg tggtggcgct caccaccgac   840
ctcccgcaga cgccgctggt catcgctatc tcctacttca tcaccagcct gagctacgcc   900
aacagctgcc tcaaccccct cctctacgcc ttcctggacg ccagcttccg caggaacctc   960
cgccagctga taacttgccg cgcggcagcc tgacactagt                        1000

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtcgacatgg cccggtccgc gacactggcg gcc                               33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gctagcagcg gtgccaggag aggtccgggc tca                               33

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atcgatatgg acaacgcctc gttctcggag cc                                32

<210> SEQ ID NO 43
<211> LENGTH: 32
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 43
actagtgtca ggctgccgcg cggcaagtta tc                                    32
```

SCREENING METHOD

FIELD OF THE INVENTION

The present invention relates to a screening method by using a human spleen-derived novel G protein-coupled receptor protein or its salt, and a substance relating to cholesterol metabolism, which is a ligand, a novel G protein-coupled receptor protein derived from mouse, rat, bovine or rabbit, and the DNA thereof, a method of determining a ligand for orphan receptor, and the like.

BACKGROUND ART

Physiological active substances such as various hormones and neurotransmitters regulate the biological function via specific receptor proteins present on cell membranes. Many of these receptor proteins are coupled with guanine nucleotide-binding protein (hereinafter sometimes simply referred to as G protein) and mediate the intracellular signal transduction via activation of G protein. These receptor proteins possess the common structure containing seven transmembrane domains and are thus collectively referred to as G protein-coupled receptors or seven-transmembrane receptors (7TMR).

G protein-coupled receptor proteins present on the cell surface of each functional cell and organ in the body, and play important physiological roles as the target of the molecules that regulate the functions of the cells and organs, e.g., hormones, neurotransmitters, physiologically active substances and the like. Receptors transmit signals to cells via binding with physiologically active substances, and the signals induce various reactions such as activation and inhibition of the cells.

To clarify the relationship between substances that regulate complex biological functions in various cells and organs, and their specific receptor proteins, in particular, G protein-coupled receptor proteins, would elucidate the functional mechanisms in various cells and organs in the body to provide a very important means for development of drugs closely associated with the functions.

For example, in various organs, their physiological functions are controlled in vivo through regulation by many hormones, hormone-like substances, neurotransmitters or physiologically active substances. In particular, physiologically active substances are found in numerous sites of the body and regulate the physiological functions through their corresponding receptor proteins. However, it is supposed that many unknown hormones, neurotransmitters or many other physiologically active substances still exist in the body and, as to their receptor proteins, many of these proteins have not yet been reported. In addition, it is still unknown if there are subtypes of known receptor proteins.

It is very important for development of drugs to clarify the relationship between substances that regulate elaborated functions in vivo and their specific receptor proteins. Furthermore, for efficient screening of agonists and antagonists to receptor proteins in development of drugs, it is required to clarify functional mechanisms of receptor protein genes expressed in vivo and express the genes in an appropriate expression system.

In recent years, random analysis of cDNA sequences has been actively studied as a means for analyzing genes expressed in vivo. The sequences of cDNA fragments thus obtained have been registered on and published to databases as Expressed Sequence Tag (EST). However, since many ESTs contain sequence information only, it is difficult to predict their functions from the information.

Substances that inhibit binding between G protein-coupled proteins and physiologically active substances (i.e., ligands) and substances that bind and induce signals similar to those induced by physiologically active substances (i.e., ligands) have been used as pharmaceuticals, as antagonists and agonists specific to the receptors, that regulate the biological functions. Therefore, discovery and gene cloning (e.g., cDNA) of a novel G protein-coupled receptor that can be targeted for pharmaceutical development are very important means in search for a specific ligand, agonist, and antagonist of the novel G protein-coupled receptor.

However, not all G protein-coupled receptors have been discovered. There are unknown G protein-coupled receptors and many of these receptors in which the corresponding ligands are yet unidentified are called orphan receptors. Therefore, search and functional elucidation of a novel G protein-coupled receptor is awaited.

G protein-coupled receptors are useful in searching for a novel physiological active substance (i.e., ligand) using the signal transduction activity as the index and in search for agonists and antagonists of the receptor. Even if no physiological ligand is found, agonists and antagonist of the receptor may be prepared by analyzing the physiological action of the receptor through inactivation experiment of the receptor (knockout animal). Ligands, agonists, antagonists, etc. of the receptor are expected to be used as prophylactic/therapeutic and diagnostic agents for diseases associated with dysfunction of the G protein-coupled receptor.

Lowering or accentuation in functions of the G protein coupled receptor due to genetic aberration of the receptor in vivo causes some disorders in many cases. In this case, the G protein coupled receptor may be used not only for administration of antagonists or agonists of the receptor, but also for gene therapy by transfer of the receptor gene into the body (or some specific organs) or by introduction of the antisense nucleic acid of the receptor gene into the body (or the specific organ). In the gene therapy, information on the base sequence of the receptor gene is essentially required for investigating deletion or mutation in the gene. The receptor gene is also applicable as prophylactic/therapeutic and diagnostic agents for diseases associated with dysfunction of the receptor.

On the other hand, in a conventional method of screening and determining a ligand or the like, when a binding molecule to a receptor is screened using, for example, eukaryotic cells, so-called stable cell line, in which the receptor is stably expressed, must be established. Further, specific cells are required for an establishment of the cell line. In addition, for a screening, it is necessary for a combination of multiple assays. Thus, when a number of test compounds exist, it takes a long time to assay and is unable to carry out the assay. That is, in a conventional method of screening and determining a ligand or the like, problems described below are presented:

(1) Usable cell lines are restricted;

(2) It takes a long time to establish the cell lines;

(3) Because of a comnination of multiple assays, a number of samples become large and it comes with difficulty to assay. In order to solve the problems, it may be desired to develop a method, for which various cell lines can be used, and assays can be carried out for a short time.

DISCLOSURE OF THE INVENTION

As a result of extensive investigations, the present inventors have found a screening method, which is not necessary for specific cell lines. In addition, they have found that a ligand for human spleen-derived G protein-coupled receptor protein is a substance relating to cholesterol metabolism. Based on these findings, the present inventors have continued further extensive studies and as a result, have come to accomplish the present invention.

Thus, the present invention relates to the following features:

[1] A method of screening a compound or salts thereof that alter the binding property between a G protein-coupled receptor protein or salts thereof, and a substance relating to cholesterol metabolism, which comprises using (1) the receptor protein containing the same or substantially the same amino acid sequence as the amino acid sequence represented by SEQ ID NO: 1, a partial peptide of the receptor protein or salts thereof, and (2) the substance relating to cholesterol metabolism;

[2] The screening method according to [1], using a G protein-coupled receptor protein containing the amino acid sequence represented by SEQ ID NO: 5, a partial peptide of the receptor protein, or salts thereof;

[3] The screening method according to [1], using a G protein-coupled receptor protein containing the amino acid sequence represented by SEQ ID NO: 7, a partial peptide of the receptor protein, or salts thereof;

[4] The screening method according to [1], using a G protein-coupled receptor protein containing the amino acid sequence represented by SEQ ID NO: 14, a partial peptide of the receptor protein, or salts thereof;

[5] The screening method according to [1], using a G protein-coupled receptor protein containing the amino acid sequence represented by SEQ ID NO: 16, a partial peptide of the receptor protein, or salts thereof;

[6] A kit for screening a compound or salts thereof that alter the binding property between a G protein-coupled receptor protein or salts thereof, and a substance relating to cholesterol metabolism, which comprises using (1) the receptor protein containing the same or substantially the same amino acid sequence as the amino acid sequence represented by SEQ ID NO: 1, a partial peptide of the receptor protein or salts thereof, and (2) the substance relating to cholesterol metabolism;

[7] A compound that alters the binding property between the substance relating to cholesterol metabolism and the G protein-coupled receptor protein containing the same or substantially the same amino acid sequence represented by SEQ iD NO: 1 or salts thereof, which is obtainable by the screening method of [1] or the screening kit of [6], or salts thereof;

[8] A medicine comprising the compound or salts thereof according to [7];

[9] A prophylactic and/or therapeutic agent for inflammatory diseases or hyper immunoreaction after implantation comprising an agonist to the G protein-coupled receptor protein containing the same or substantially the same amino acid sequence represented by SEQ ID NO: 1, which is obtainable by the screening method of [1] or the screening kit of [6], or salts thereof;

[10] A prophylactic and/or therapeutic agent for immunodeficiency diseases or infectious diseases comprising an agonist to the G protein-coupled receptor protein containing the same or substantially the same amino acid sequence represented by SEQ ID NO: 1, which is obtainable by the screening method of [1] or the screening kit of [6], or salts thereof;

[11] A method of prophylaxis and/or therapy for inflammatory diseases or hyper immunoreaction after implantation, which comprises administering an effective doses of the agonist to the G protein-coupled receptor protein containing the same or substantially the same amino acid sequence represented by SEQ ID NO: 1, which is obtainable by the screening method of [1] or the screening kit of [6], or salts thereof, to mammals;

[12] A method of prophylaxis and/or therapy for immunodeficiency diseases or infectious diseases, which comprises administering an effective doses of the agonist to the G protein-coupled receptor protein containing the same or substantially the same amino acid sequence represented by SEQ ID NO: 1, which is obtainable by the screening method of [1] or the screening kit of [6], or salts thereof, to mammals;

[13] Use of the agonist to the G protein-coupled receptor protein containing the same or substantially the same amino acid sequence represented by SEQ ID NO: 1, which is obtainable by the screening method of [1] or the screening kit of [6], or salts thereof, for manufacturing a prophylactic and/or therapeutic agent for inflammatory diseases or hyper immunoreaction after implantation;

[14] Use of the agonist to the G protein-coupled receptor protein containing the same or substantially the same amino acid sequence represented by SEQ ID NO: 1, which is obtainable by the screening method of [1] or the screening kit of [6], or salts thereof, for manufacturing a prophylactic and/or therapeutic agent for immunodeficiency diseases or infectious diseases;

[15] A prophylactic and/or therapeutic agent for inflammatory diseases or hyper immunoreaction after implantation comprising a compound or salts thereof that increase an expression level of the G protein-coupled receptor protein containing the same or substantially the same amino acid sequence represented by SEQ ID NO:1;

[16] A prophylactic and/or therapeutic agent for immunodeficiency diseases or infectious diseases comprising a compound or salts thereof that reduce an expression level of the G protein-coupled receptor protein containing the same or substantially the same amino acid sequence represented by SEQ ID NO: 1;

[17] A method of prophylaxis and/or therapy for inflammatory diseases or hyper immunoreaction after implantation, which comprises administering an effective dose of the compound or salts thereof that increase an expression level of the G protein-coupled receptor protein containing the same or substantially the same amino acid sequence represented by SEQ ID NO: 1, to mammals;

[18] A method of prophylaxis and/or therapy for immunodeficiency diseases or infectious diseases, which comprises administering an effective doses of the compound or salts thereof that reduce an expression level of the G protein-coupled receptor protein containing the same or substantially the same amino acid sequence represented by SEQ ID NO: 1, to mammals;

[19] Use of the compound or salts thereof that increase an expression level of the G protein-coupled receptor protein containing the same or substantially the same amino acid sequence represented by SEQ ID NO: 1, for manufacturing a prophylactic and/or therapeutic agent for inflammatory diseases or hyper immunoreaction after implantation;

[20] Use of the compound or salts thereof that reduce an expression level of the G protein-coupled receptor protein containing the same or substantially the same amino acid sequence represented by SEQ ID NO: 1, for manufacturing a prophylactic and/or therapeutic agent for immunodeficiency diseases or infectious diseases;

[21] A prophylactic and/or therapeutic agent for inflammatory diseases or hyper immunoreaction after implantation comprising the G protein-coupled receptor protein containing the same or substantially the same amino acid sequence represented by SEQ ID NO: 1, its partial peptide, or salts thereof;

[22] A prophylactic and/or therapeutic agent for inflammatory diseases or hyper immunoreaction after implantation comprising a polynucleotide containing the polynucleotide encoding the G protein-coupled receptor protein containing the same or substantially the same amino acid sequence represented by SEQ ID NO: 1 or its partial peptide;

[23] A diagnostic for central diseases, inflammatory diseases, circuratory diseases, canser, respiratory diseases, diabetes, immune system disorders, diseases of liver and gallbladder, alimentary diseases, infectious diseases, adiposis or hyper immunoreaction after implantation comprising a polynucleotide containing the polynucleotide encoding the G protein-coupled receptor protein containing the same or substantially the same amino acid sequence represented by SEQ ID NO: 1 or its partial peptide;

[24] A prophylactic and/or therapeutic agent for immunodeficiency diseases or infectious diseases comprising an antibody against the G protein-coupled receptor protein containing the same or substantially the same amino acid sequence represented by SEQ ID NO: 1, its partial peptide, or salts thereof;

[25] A diagnostic for central diseases, inflammatory diseases, circuratory diseases, canser, respiratory diseases, diabetes, immune system disorders, diseases of liver and gallbladder, alimentary diseases, infectious diseases, adiposis or hyper immunoreaction after implantation comprising an antibody against the G protein-coupled receptor protein containing the same or substantially the same amino acid sequence represented by SEQ ID NO: 1, its partial peptide, or salts thereof;

[26] A prophylactic and/or therapeutic agent for immunodeficiency diseases or infectious diseases comprising an antisense polynucleotide containing a base sequence complementary to a polynucleotide containing the polynucleotide encoding the G protein-coupled receptor protein containing the same or substantially the same amino acid sequence represented by SEQ ID NO: 1 or its partial peptide, or a portion thereof;

[27] A diagnostic for central diseases, inflammatory diseases, circuratory diseases, canser, respiratory diseases, diabetes, immune system disorders, diseases of liver and gallbladder, alimentary diseases, infectious diseases, adiposis or hyper immunoreaction after implantation comprising an antisense polynucleotide containing a base sequence complementary to a polynucleotide containing the polynucleotide encoding the G protein-coupled receptor protein containing the same or substantially the same amino acid sequence represented by SEQ ID NO: 1 or its partial peptide, or a portion thereof;

[28] A method of prophylaxis and/or therapy for inflammatory diseases or hyper immunoreaction after implantation, which comprises administering an effective dose of the G protein-coupled receptor protein containing the same or substantially the same amino acid sequence represented by SEQ ID NO: 1, its partial peptide, or salts thereof, to mammals;

[29] A method of prophylaxis and/or therapy for inflammatory diseases or hyper immunoreaction after implantation, which comprises administering an effective dose of the polynucleotide containing the polynucleotide encoding the G protein-coupled receptor protein containing the same or substantially the same amino acid sequence represented by SEQ ID NO: 1 or its partial peptide, to mammals;

[30] A method of prophylaxis and/or therapy for immunodeficiency diseases or infectious diseases, which comprises administering an effective dose of the antibody against the G protein-coupled receptor protein containing the same or substantially the same amino acid sequence represented by SEQ ID NO: 1, its partial peptide, or salts thereof, to mammals;

[31] A method of prophylaxis and/or therapy for immunodeficiency diseases or infectious diseases, which comprises administering an effective dose of the antisense polynucleotide containing a base sequence complementary to a polynucleotide containing the polynucleotide encoding the G protein-coupled receptor protein containing the same or substantially the same amino acid sequence represented by SEQ ID NO: 1 or its partial peptide, or a portion thereof, to mammals;

[32] Use of the G protein-coupled receptor protein containing the same or substantially the same amino acid sequence represented by SEQ ID NO: 1, its partial peptide, or salts thereof, for manufacturing a prophylactic and/or therapeutic agent fot inflammatory diseases or hyper immunoreaction after implantation;

[33] Use of the polynucleotide containing the polynucleotide encoding the G protein-coupled receptor protein containing the same or substantially the same amino acid sequence represented by SEQ ID NO: 1 or its partial peptide, for manufacturing a prophylactic and/or therapeutic agent fot inflammatory diseases or hyper immunoreaction after implantation;

[34] Use of the antibody against the G protein-coupled receptor protein containing the same or substantially the same amino acid sequence represented by SEQ ID NO: 1, its partial peptide, or salts thereof, for manufacturing a prophylactic and/or therapeutic agent fot immunodeficiency diseases or infectious diseases;

[35]0 Use of the antisense polynucleotide containing a base sequence complementary to a polynucleotide containing the polynucleotide encoding the G protein-coupled receptor protein containing the same or substantially the same amino acid sequence represented by SEQ ID NO: 1 or its partial peptide, or a portion thereof, for manufacturing a prophylactic and/or therapeutic agent fot immunodeficiency diseases or infectious diseases;

[36] A G protein-coupled receptor protein, which comprises containing the same or substantially the same amino acid sequence as the amino acid sequence represented by SEQ ID NO: 5, SEQ ID NO: 7, SEQ ID NO: 14 or SEQ ID NO: 16, or salts thereof;

[37] A partial peptide of the G protein-coupled receptor protein according to [36], or salts thereof;

[38] A polynucleotide containing the polypeptide encoding the G protein-coupled receptor protein according to [36] or the partial peptide according to [37];

[39] The polynucleotide according to [38], which is DNA;

[40] The polynucleotide according to [38], which has a base sequence represented by SEQ ID NO: 6, SEQ ID NO: 8, SEQ ID NO: 13 or SEQ ID NO: 15;

[41] A recombinant vector containing the polynucleotide according to [38];

[42] A transformant, which is transformed with the recombinant vector according to [41];

[43] A method of manufacturing the G protein-coupled receptor protein or salts thereof according to [36], which comprises culturing the transformant according to [42] and producing the G protein-coupled receptor protein according to [36];

[44] An antibody against the G protein-coupled receptor protein according to [36] or the partial peptide according to [37], or salts thereof;

[45] The antibody according to [44], which is a neutralizing antibody that inactivates a signal transduction by the G protein-coupled receptor protein according to [36];

[46] A diagnostic comprising the antibody according to [44];

[47] The diagnostic according to [46], which is a diagnostic for central diseases, inflammatory diseases, circuratory diseases, canser, respiratory diseases, diabetes, immune system disorders, diseases of liver and gallbladder, alimentary diseases, infectious diseases, adiposis or hyper immunoreaction after implantation;

[48] A medicine comprising the antibody according to [44];

[49] The medicine according to [48], which is a prophylactic and/or therapeutic agent for immunodeficiency or infectious diseases;

[50] A medicine comprising the G protein-coupled receptor protein according to [36], a partial peptide thereof, or salts thereof;

[51] The medicine according to [50], which is a prophylactic and/or therapeutic agent for inflammatory diseases or hyper immunoreaction after implantation;

[52] A medicine comprising the polynucleotide according to [38];

[53] The medicine according to [52], which is a prophylactic and/or therapeutic agent for inflammatory diseases or hyper immunoreaction after implantation;

[54] A diagnostic comprising the polynucleotide according to [38];

[55] The diagnostic according to [54], which is a diagnostic for central diseases, inflammatory diseases, circuratory diseases, canser, respiratory diseases, diabetes, immune system disorders, diseases of liver and gallbladder, alimentary diseases, infectious diseases, adiposis or hyper immunoreaction after implantation;

[56] An antisense polynucleotide, which comprises a base sequence complimentary to the polynucleotide according to [38], or a portion thereof;

[57] A medicine comprising the antisense polynucleotide according to [56];

[58] The medicine according to [57], which is a prophylactic and/or therapeutic agent for immunodeficiency or infectious diseases;

[59] A diagnostic comprising the antisense polynucleotide according to [56];

[60] The diagnostic according to [59], which is a diagnostic for central diseases, inflammatory diseases, circuratory diseases, canser, respiratory diseases, diabetes, immune system disorders, diseases of liver and gallbladder, alimentary diseases, infectious diseases, adiposis or hyper immunoreaction after implantation;

[61] A method of determining a ligand to the receptor protein, which comprises adding a test compound to animal cells expressing a receptor protein, which the ligand is not determined, and containing a plasmid, which a DNA encoding reporter protein is ligated downstream cAMP response element/promoter, and measuring an activity of the reporter protein;

[62] The method according to [61], which comprises adding a test compound to animal cells containing (1) a plasmid containing a DNA encoding a receptor protein, which the ligand is not determined, and (2) a plasmid, which a DNA encoding reporter protein is ligated downstream cAMP response element/promoter, and measuring an activity of the reporter protein;

[63] The method according to [61] or [62], wherein the receptor protein is a G protein-coupled receptor protein;

[64] The method according to [63], wherein the G protein-coupled receptor protein is a G protein-coupled receptor protein containing the same or substantially the same amino acid sequence as the amino acid sequence represented by SEQ ID NO: 5, SEQ ID NO: 7, SEQ ID NO: 14 or SEQ ID NO: 16;

[65] The method according to [61] or [62], wherein the promoter is a TATA-like sequence;

[66] The method according to [61] or [62], wherein the reporter protein is a luciferase;

[67] The method according to [61] or [62], wherein the plasmid is a plasmid, to which a TATA-like promoter and a gene encoding the reporter protein are ligated downstream cAMP response element;

[68] The method according to [61] or [62], wherein the animal cells express two or more receptor proteins, which the ligand is not determined;

[69] The method according to [61] or [62], wherein the cells contain a plasmid containing a gene encoding inhibitory G protein α subunit Gi;

[70] The method according to [61] or [62], wherein further forskolin is added;

[71] The method according to [68], which comprises that two or more receptor proteins have similar characteristics;

[72] The method according to [68], wherein the similar characteristics is a basic expression level of the reporter protein and (or) an expression level of the reporter protein at the time of adding forskolin;

[73] The method according to [68], which comprises measuring the basic expression level of the reporter protein when two or more receptor proteins are independently expressed, and (or) the expression level of the reporter protein when forskolin is added, and expressing a combination of two or more receptor proteins, wherein the expression level of the reporter protein is at the same level as each other.

BRIEF DESCRIPTION OF THE DRAWINGS

FIG. 1 shows a base sequence of cDNA (residues 1–270 of SEQ ID NO: 2) encoding TGR5 obtained in Reference Example 1, and a predicted amino acid sequence (residues 1–90 of SEQ ID NO: 1) (one letter code) therefrom.

FIG. 2 shows a base sequence of cDNA (residues 271–540 of SEQ ID NO: 2) encoding TGR5 obtained in Reference Example 1, and a predicted amino acid sequence (residues 91–180 of SEQ ID NO: 1) (one letter code) therefrom (continued from FIG. 1).

FIG. 3 shows a base sequence of cDNA (residues 541–810 of SEQ ID NO: 2) encoding TGR5 obtained in Reference Example 1, and a predicted amino acid sequence (residues 181–270 of SEQ ID NO: 1) (one letter code) therefrom (continued from FIG. 2).

FIG. 4 shows a base sequence of cDNA (residues 811–993 of SEQ ID NO: 2) encoding TGR5 obtained in Reference Example 1, and a predicted amino acid sequence (residues 271–330 of SEQ ID NO: 1) (one letter code) therefrom (continued from FIG. 3).

FIG. 6 shows the result of detection for the activity of the substance relating cholesterol metabolism (n=2) in HEK293 cells (A), wherein the TGR5 expression vector was introduced, and in HEK293 cells (B), wherein the original vector.was introduced.

FIG. 28 shows a DNA sequence of human GPR7 ligand precursor H (SEQ ID NO: 37).

FIG. 29 shows an amino acid sequence of human GPR7 ligand precursor H (SEQ ID NO: 36).

BEST MODE FOR CARRYING OUT THE INVENTION

Figure 5:
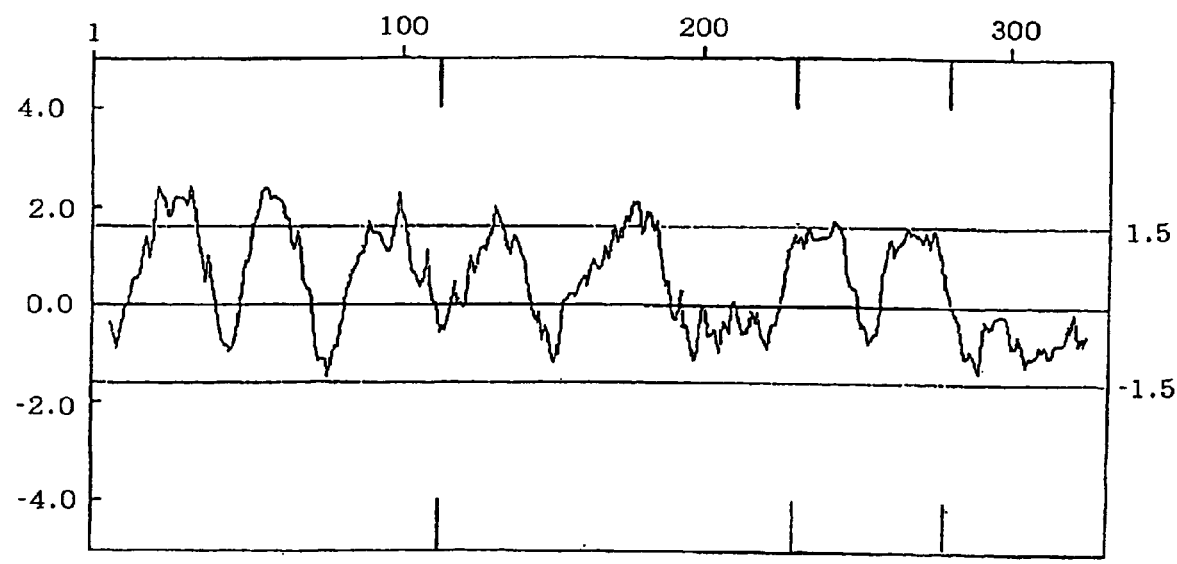
FIG. 5 shows a hydrophobicity plot of TGR5.

The G protein-coupled receptor protein of the present invention (hereinafter sometimes merely referred to as the receptor protein) is a receptor protein, which contains the same or substantially the same amino acid sequence as the amino acid sequence represented by SEQ ID NO: 1, SEQ ID NO: 5, SEQ ID NO: 7, SEQ ID NO: 14, or SEQ ID NO: 16.

The receptor protein of the present invention may be any protein derived from any cells (e.g., splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.) or hematocyte, or any tissues where such cells are present, e.g., brain or any region of the brain (e.g., olfactory bulb, amygdaloid nucleus, basal ganglia, hippocampus, thalamus, hypothalamus, subthalamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, peripheral blood cells, prostate, testis, ovary, placenta, uterus, bone, joint, skeletal muscle, etc., from human and other mammals (e.g., guinea pigs, rats, mice, rabbits, swine, sheep, bovine, monkeys, etc.). The receptor protein may also be a synthetic protein.

The amino acid sequence which has substantially the same amino acid sequence as that represented by SEQ ID NO: 1, SEQ ID NO: 5, SEQ ID NO: 7, SEQ ID NO: 14, or SEQ ID NO: 16 includes an amino acid sequence having at least about 50% homology, preferably at least about 60% homology, more preferably at least about 70% homology, much more preferably at least about 80% homology, among others preferably at least about 90% homology and most preferably at least about 95% homology, to the amino acid sequence represented by SEQ ID NO: 1 SEQ ID NO: 5, SEQ ID NO: 7, SEQ ID NO: 14, or SEQ ID NO: 16.

Examples of the protein of the invention, which contains substantially the same amino acid sequence as that shown by SEQ ID NO: 1, SEQ ID NO: 5, SEQ ID NO: 7, SEQ ID NO: 14, or SEQ ID NO: 16, include a protein having substantially the same amino acid sequence as that shown by SEQ ID NO: 1, SEQ ID NO: 5, SEQ ID NO: 7, SEQ ID NO: 14, or SEQ ID NO: 16 and having the activity substantially equivalent to the amino acid sequence represented by SEQ ID NO: 1, SEQ ID NO: 5, SEQ ID NO: 7, SEQ ID NO: 14, or SEQ ID NO: 16, etc.

Examples of the substantially equivalent activity include a ligand binding activity, a signal transduction activity, etc. The term "substantially equivalent" is used to mean that the nature of the activity is the same. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of the activity, a molecular weight of the protein, etc, may differ.

The activities such as ligand binding and signal transduction activities or the like can be determined according to a publicly known method with some modifications, for example, by the ligand determination methods or the screening methods that will be later described.

Proteins containing the following amino acid sequences are used as the receptor protein of the present invention: (1) (i) amino acid sequences represented by SEQ ID NO: 1, SEQ ID NO: 5, SEQ ID NO: 7, SEQ ID NO: 14, or SEQ ID NO: 16, wherein at least 1 or 2 amino acids (preferably approximately 1 to 30 amino acids, more preferably approximately 1 to 10 amino acids, most preferably several (1 to 5) amino acids) are deleted; (ii) amino acid sequences represented by SEQ ID NO: 1, SEQ ID NO: 5, SEQ ID NO: 7, SEQ ID NO: 14, or SEQ ID NO: 16, to which at least 1 or 2 amino acids (preferably approximately 1 to 30 amino acids, more preferably approximately 1 to 10 amino acids, and most preferably several (1 to 5) amino acids) are added; (iii) amino acid sequences represented by SEQ ID NO: 1, SEQ ID NO: 5, SEQ ID NO: 7, SEQ ID NO: 14, or SEQ ID NO: 16, in which at least 1 or 2 amino acids (preferably approximately 1 to 30 amino acids, more preferably approximately 1 to 10 amino acids, and most preferably several (1 to 5) amino acids) are substituted by other amino acids; or (iv) combination of the amino acid sequences described in the above.

Throughout the present specification, the receptor proteins are represented in accordance with the conventional way of describing peptides, that is, the N-terminus (amino terminus) at the left hand and the C-terminus (carboxyl terminus) at the right hand. In the receptor proteins of the present invention including the receptor proteins containing the amino acid sequence shown by SEQ ID NO: 1, the C-terminus is usually in the form of a carboxyl group (—COOH) or a carboxylate (—COO⁻) but may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the receptor protein of the present invention contains a carboxyl group (or a carboxylate) at a position other than the C-terminus, it may be amidated or esterified and such an amide or ester is also included within the receptor protein of the present invention. The ester group may be the same group as that described with respect to the C-terminus described above.

Furthermore, examples of the receptor protein of the present invention include variants of the above receptor proteins, wherein the amino group at the N-terminal methionine residue of the protein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of the receptor protein of the present invention which can be used include a receptor protein containing an amino acid sequence represented by SEQ ID NO: 1, SEQ ID NO: 5, SEQ ID NO: 7, SEQ ID NO: 14, or SEQ ID NO: 16, etc.

As partial peptides of the receptor protein of the present invention (hereinafter sometimes referred to as the partial peptides), any partial peptide can be used so long as it can be a partial peptide of the receptor protein. Among the receptor protein molecules of the present invention, for example, those having a site exposed to the outside of a cell membrane and having a receptor binding activity can be used.

Specifically, the partial peptide of the receptor protein containing the amino acid sequence represented by SEQ ID NO: 1, SEQ ID NO: 5, SEQ ID NO: 7, SEQ ID NO: 14, or SEQ ID NO: 16 is a peptide containing the parts analyzed to be extracellular domains (hydrophilic domains) in the hydrophobic plotting analysis. A peptide containing a hydrophobic domain in part can be used as well. In addition, the peptide may contain each domain separately or plural domains together.

In the receptor protein of the present invention, preferred partial peptides are those having at least 20, preferably at least 50, and more preferably at least 100 amino acids, in the amino acid sequence which constitutes the receptor protein of the present invention.

The amino acid sequence having substantially the same amino acid sequence includes an amino acid sequence having at least about 50% homology, preferably at least about 60% homology, more preferably at least about 70% homology, much more preferably at least about 80% homology, among others preferably at least about 90% homology and most preferably at least about 95% homology, to these amino acid sequences.

Herein, the term "receptor binding activity substantially equivalent" refers to the same significance as defined above. The "receptor binding activity substantially equivalent" can be assayed in the same manner as given above.

The partial peptide of the present invention may contain an amino acid sequence, wherein at least 1 or 2 amino acids (preferably approximately 1 to 10 amino acids, more preferably several (1 to 5) amino acids) are deleted; to which at least 1 or 2 amino acids (preferably approximately 1 to 20 amino acids, more preferably approximately 1 to 10 amino acids, and most preferably several (1 to 5) amino acids) are added; or, in which at least 1 or 2 amino acids (preferably approximately 1 to 10 amino acids, more preferably several and most preferably approximately 1 to 5 amino acids) are substituted by other amino acids.

Although in the partial peptide of the present invention, the C-terminus is normally a carboxyl group (—COOH) or carboxylate (—COO⁻), the C-terminus may be in the form of an amide (—CONH$_2$) or an ester (—COOR). Where the partial peptide of the invention has a carboxyl group (or carboxylate) other than C-terminus, amidated or esterified carboxyl group was included in the partial peptide of the invention. For ester in this case, for example, ester at the C-terminus described above can be used.

As in the receptor protein of the present invention described above, the partial peptide of the present invention further includes those in which the amino group of the amino acid residue of the N-terminal methionine residue is protected by a protecting group, those in which the N-terminal residue is cleaved in vivo and the produced glutamine residue is pyroglutaminated, those in which substituents on the side chains of amino acids in the molecule are protected by appropriate protecting groups, conjugated peptides such as so-called glycoproteins, to which sugar chains are bound, and the like.

For salts of the receptor protein or the partial peptide of the present invention, preferred are salts with physiologically acceptable acids, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The receptor protein of the present invention or salts thereof may be manufactured by a publicly known method used to purify a receptor protein from human and other mammalian cells or tissues described above, or by culturing a transformant that contains the DNA encoding the receptor protein of the present invention, as will be later described. Furthermore, the receptor protein or its salts may also be manufactured by the methods for synthesizing proteins or by modifications thereof, which will also be described hereinafter.

Where the receptor protein or its salts are manufactured from human and mammalian tissues or cells, human and mammalian tissues or cells are homogenized, then extracted with an acid or the like, and the extract is isolated and purified by a combination of chromatography techniques such as reverse phase chromatography, ion exchange chromatography, and the like.

To synthesize the receptor protein of the present invention, its partial peptide, or salts or amides thereof according to the present invention, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the receptor protein is cut out from the resin and at the same time, the protecting groups are removed. Then, intramolecular disulfide bond-forming reaction is performed in a highly diluted solution to obtain the objective protein or its amides.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, elimination of the protecting groups and activation of functional groups involved in the reaction may be appropriately selected from publicly known groups and publicly known means and applied.

In another method for obtaining the amides of the protein, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group in the peptide chain has been eliminated from the protein and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the ester form of the desired protein.

The partial peptide or its salts in the protein of the present invention can be manufactured by publicly known methods for peptide synthesis, or by cleaving the protein of the present invention with an appropriate peptidase. For the methods for peptide synthesis, for example, either solid phase synthesis or liquid phase synthesis may be used. That is, the partial peptide or amino acids that can construct the protein of the present invention are condensed with the remaining part. Where the product contains protecting groups, these protecting groups are removed to give the desired peptide. Publicly known methods for condensation and elimination of the protecting groups are described in (1)–(5) below.

(1) M. Bodanszky & M. A. Ondetti: Peptide Synthesis, Interscience Publishers, New York (1966)

(2) Schroeder & Luebke: The Peptide, Academic Press, New York (1965)

(3) Nobuo Izumiya, et al.: *Peptide Gosei-no-Kiso to Jikken* (Basics and experiments of peptide synthesis), published by Maruzen Co. (1975)

(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(5) Haruaki Yajima, ed.: *Zoku lyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt by a publicly known method; when the protein is obtained in a salt form, it can be converted into a free form by a publicly known method.

The polynucleotide encoding the receptor protein of the present invention may be any polynucleotide so long as it contains the base sequence (DNA or RNA, preferably DNA) encoding the receptor protein of the present invention described above. Such a polynucleotide may also be any one of DNA encoding the receptor protein of the present invention, RNA such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the receptor protein of the present invention, mRNA of the receptor protein of the present invention can be quantified by, for example, the publicly known method published in separate volume of *Jikken Igaku* 15 (7) "New PCR and its application" (1997), or by its modifications.

The DNA encoding the receptor protein of the present invention may be any of genomic DNA, genomic DNA library, cDNA derived from the cells or tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding the receptor protein of the present invention may be (1) DNA containing the base sequence shown by SEQ ID NO: 2, SEQ ID NO: 6, SEQ ID NO: 8, SEQ ID NO: 13 or SEQ ID NO: 15, or DNA hybridizable to DNA containing the base sequence represented by SEQ ID NO: 2, SEQ ID NO: 6, SEQ ID NO: 8, SEQ ID NO: 13 or SEQ ID NO: 15 under highly stringent conditions and encoding a receptor protein having the activities substantially equivalent to those of the receptor protein of the invention (e.g., a ligand binding activity, a signal transduction activity, etc.).

Specific examples of the DNA hybridizable to the base sequence represented by SEQ ID NO: 2, SEQ ID NO: 6, SEQ ID NO: 8, SEQ ID NO: 13 or SEQ ID NO: 15 under highly stringent conditions include DNA containing a base sequence having at least about 70% homology, preferably at least about 80% homology, more preferably at least about 90% homology and most preferably at least about 95% homology, to the base sequence represented by SEQ ID NO: 2, SEQ ID NO: 6, SEQ ID NO: 8, SEQ ID NO: 13 or SEQ ID NO: 15.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

More specifically, for the DNA encoding the receptor protein containing the amino acid sequence represented by SEQ ID NO: 1, there may be employed DNA having the base sequence represented by SEQ ID NO: 2.

Further, for the DNA encoding the receptor protein containing the amino acid sequence represented by SEQ ID NO: 5, there may be employed DNA having the base sequence represented by SEQ ID NO: 6.

For the DNA encoding the receptor protein containing the amino acid sequence represented by SEQ ID NO: 7, there may be employed DNA having the base sequence represented by SEQ ID NO: 8.

For the DNA encoding the receptor protein containing the amino acid sequence represented by SEQ ID NO: 14, there may be employed DNA having the base sequence represented by SEQ ID NO: 13.

For the DNA encoding the receptor protein containing the amino acid sequence represented by SEQ ID NO: 16, there may be employed DNA having the base sequence represented by SEQ ID NO: 15.

The polynucleotide comprising a part of the base sequence of the DNA encoding the receptor protein of the present invention or a part of the base sequence complementary to the DNA is used to mean to embrace not only the DNA encoding the partial peptide of the present invention described below but also RNA.

According to the present invention, antisense polynucleotides (nucleic acids) that can inhibit the replication or expression of G protein-coupled receptor protein genes can be designed and synthesized based on the base sequence information of the cloned or determined DNA encoding the G protein-coupled receptor protein. Such a polynucleotide (nucleic acid) is capable of hybridizing to RNA of G protein-coupled receptor protein gene to inhibit the synthesis or function of said RNA or capable of modulating or controlling the expression of a G protein-coupled receptor protein gene via interaction with G protein-coupled receptor protein-associated RNA. Polynucleotides complementary to the selected sequences of RNA associated with G protein-coupled receptor protein and polynucleotides specifically hybridizable to the G protein-coupled receptor protein-associated RNA are useful in modulating or controlling the expression of a G protein-coupled receptor protein gene in vivo and in vitro, and useful for the treatment or diagnosis of diseases. The term "corresponding" is used to mean homologous to or complementary to a particular sequence of the nucleotide, base sequence or nucleic acid including the gene. The term "corresponding" between nucleotides, base sequences or nucleic acids and peptides (proteins) usually refer to amino acids of a peptide (protein) under the order derived from the sequence of nucleotides (nucleic acids) or their complements. In the G protein-coupled receptor protein genes, the 5' end hairpin loop, 5' end 6-base-pair repeats, 5' end untranslated region, polypeptide translation initiation codon, protein coding region, ORF translation initiation codon, 3' end untranslated region, 3' end palindrome region, and 3' end hairpin loop, may be selected as preferred target regions, though any other region may be selected as a target in the G protein-coupled receptor protein genes.

The relationship between the targeted nucleic acids and the polynucleotides complementary to at least a part of the target, specifically the relationship between the target and the polynucleotides hybridizable to the target, can be denoted to be "antisense". Examples of the antisense polynucleotides include polydeoxynucleotides containing 2-deoxy-D-ribose, polynucleotides containing D-ribose, any other type of polynucleotides which are N-glycosides of a purine or pyrimidine base, or other polymers containing non-nucleotide backbones (e.g., protein, nucleic acids and synthetic sequence-specific nucleic acid polymers commercially available) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., α anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain altered or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation. system of the G protein-coupled receptor protein in vivo and in vitro. The nucleic acid can also be applied to cells by a variety of publicly known methods.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by RT-PCR using mRNA fraction prepared from the cells and tissues described above.

Specifically, the DNA encoding the partial peptide of the present invention may be any one of, for example, (1) DNA having a partial base sequence of the DNA containing the base sequence represented by SEQ ID NO: 2, SEQ ID NO: 6, SEQ ID NO: 8, SEQ ID NO: 13 or SEQ ID NO: 15, (2) DNA having a DNA hybridizable to the DNA containing the base sequence represented by SEQ ID NO: 2, SEQ ID NO: 6, SEQ ID NO: 8, SEQ ID NO: 13 or SEQ ID NO: 15 under highly stringent conditions and having a partial base sequence of the DNA:encoding a protein which has the activities (e.g., a ligand-biding activity, a signal transduction activity, etc.) substantially equivalent to those of the peptide of the receptor protein of the invention.

Specific examples of the DNA that is hybridizable to the base sequence represented by SEQ ID NO: 2, SEQ ID NO: 6, SEQ ID NO: 8, SEQ ID NO: 13 or SEQ ID NO: 15 under highly stringent conditions include DNA containing a base sequence having at least about 70% homology, preferably at least about 80% homology, more preferably at least about 90% homology and most preferably at least about 95% homology, to the base sequence represented by SEQ ID NO: 2, SEQ ID NO: 6, SEQ ID NO: 8, SEQ ID NO: 13 or SEQ ID NO: 15.

For cloning of the DNA that completely encodes the receptor protein of the present invention or its partial peptide (hereinafter sometimes collectively referred to as the receptor protein of the present invention), the DNA may be either amplified by PCR using synthetic DNA primers containing a part of the base sequence encoding the receptor protein of the present invention, or the DNA inserted into an appropriate vector can be selected by hybridization with a labeled DNA fragment or synthetic DNA that encodes a part or entire region of the receptor protein of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Substitution of the base sequence of the DNA can be effected by publicly known methods such as the ODA-LA PCR method, the Gupped duplex method or the Kunkel method or its modification by using a publicly known kit available as Mutan™-G or Mutan™-K (both manufactured by Takara Shuzo Co., Ltd.).

The cloned DNA encoding the receptor protein can be used as it is, depending upon purpose or, if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons may also be added by using an appropriate synthetic DNA adapter.

The expression vector for the receptor protein of the present invention can be manufactured, for example, by (a) excising the desired DNA fragment from the DNA containing the DNA encoding the receptor protein of the present invention (for example, cDNA), and then (b) ligating the DNA fragment with an appropriate expression vector downstream a promoter in the vector.

Examples of the vector include plasmids derived form E. coli (e.g., pBR322, pBR325, pUC12, pUC13), plasmids derived from Bacillus subtilis (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV promoter or SRα promoter is preferably used. Where the host is bacteria of the genus Escherichia, preferred examples of the promoter include trp promoter, lac promoter, recA promoter, $\lambda P_L$ promoter, lpp promoter, etc. In the case of using bacteria of the genus Bacillus as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker in CHO (dhfr⁻) cells, selection can also be made on thymidine free media.

If necessary and desired, a signal sequence that matches with a host is added to the N-terminus of the receptor protein of the present invention. Examples of the signal sequence that can be used are Pho A signal sequence, OmpA signal sequence, etc. in the case of using bacteria of the genus Escherichia as the host; α-amylase signal sequence, subtilisin signal sequence, etc. in the case of using bacteria of the genus Bacillus as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the receptor protein of the present invention thus constructed, transformants can be manufactured.

Examples of the host, which may be employed, are bacteria belonging to the genus Escherichia, bacteria belonging to the genus Bacillus, yeast, insect cells, insects and animal cells, etc.

Specific examples of the bacteria belonging to the genus Escherichia include Escherichia coli K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus Bacillus include Bacillus subtilis MI114 (Gene, 24, 255 (1983)), 207-21 (Journal of Biochemistry, 95, 87 (1984)), etc.

Examples of yeast include Saccharomyces cereviseae AH22, AH22R⁻, NA87-11A, DKD-5D, 20B-12, Schizosaccharomyces pombe NCYC1913, NCYC2036, Pichia pastoris KM71, etc.

Examples of insect cells include, for the virus AcNPV, Spodoptera frugiperda cells (Sf cells), MG1 cells derived from mid-intestine of Trichoplusia ni, High Five™ cells derived from egg of Trichoplusia ni, cells derived from Mamestra brassicae, cells derived from Estigmena acrea, etc.; and for the virus BmNPV, Bombyx mori N cells (BmN cells), etc. are used. Examples of the Sf cell which can be used are Sf9 cells (ATCC CRL1711) and Sf21 cells (both cells are described in Vaughn, J. L. et al., In Vivo, 13, 213–217 (1977)).

As the insect, for example, a larva of Bombyx mori can be used (Maeda, et al., Nature, 315, 592 (1985)).

Examples of animal cells include monkey cells COS-7, Vero, Chinese hamster cells CHO (hereinafter referred to as CHO cells), dhfr gene deficient Chinese hamster cells CHO (hereinafter simply referred to as CHO(dhfr⁻) cell), mouse L cells, mouse AtT-20, mouse myeloma cells, rat GH3, human FL cells, human HEK293 cells, etc.

Bacteria belonging to the genus Escherichia can be transformed, for example, by the method described in Proc. Natl. Acad. Sci. U.S.A., 69, 2110 (1972) or Gene, 17, 107 (1982).

Bacteria belonging to the genus Bacillus can be transformed, for example, by the method described in Molecular & General Genetics, 168, 111 (1979).

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263–267 (1995), published by Shujunsha, or Virology, 52, 456 (1973).

Thus, the transformant transformed with the expression vector containing the DNA encoding the G protein-coupled receptor protein can be obtained.

Where the host is bacteria belonging to the genus Escherichia or the genus Bacillus, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus Escherichia is M9 medium supplemented with glucose and Casamino acids (Miller, Journal of Experiments in Molecular Genetics, 431–433, Cold Spring Harbor Laboratory, New York, 1972). If necessary and desired, a chemical such as 3β-indolylacrylic acid can be added to the medium thereby to activate the promoter efficiently.

Where the bacteria belonging to the genus Escherichia are used as the host, the transformant is usually cultivated at about 15° C. to about 43° C. for about 3 hours to about 24 hours. If necessary and desired, the culture may be aerated or agitated.

Where the bacteria belonging to the genus Bacillus are used as the host, the transformant is cultivated generally at about 30° C. to about 40° C. for about 6 hours to about 24 hours. If necessary and desired, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505

(1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the G protein-coupled receptor protein of the present invention can be produced into the cell, in the cell membrane or out of the cell of the transformant.

The receptor protein of the present invention can be separated and purified from the culture described above by the following procedures.

When the receptor protein of the present invention is extracted from the culture or cells, after cultivation the transformants or cells are collected by a publicly known method and suspended in a appropriate buffer. The transformants or cells are then disrupted by publicly known methods such as ultrasonication, a treatment with lysozyme and/or freeze-thaw cycling, followed by centrifugation, filtration, etc. Thus, the crude extract of the receptor protein of the present invention can be obtained. The buffer used for the procedures may contain a protein modifier such as urea or guanidine hydrochloride, or a surfactant such as Triton X-100™, etc. When the receptor protein is secreted in the culture, after completion of the cultivation the supernatant can be separated from the transformants or cells to collect the supernatant by a publicly known method.

The receptor protein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the receptor protein thus obtained is in a free form, it can be converted into the salt by publicly known methods or modifications thereof. On the other hand, when the receptor protein is obtained in the form of a salt, it can be converted into the free form or in the form of a different salt by publicly known methods or modifications thereof.

The receptor protein produced by the recombinant can be treated, prior to or after the purification, with an appropriate protein modifying enzyme so that the receptor protein can be appropriately modified to partially remove a polypeptide. Examples of the protein-modifying enzyme include trypsin, chymotrypsin, arginyl endopeptidase, protein kinase, glycosidase or the like.

The activity of the thus produced receptor protein of the present invention or salts thereof can be determined by a test binding to a labeled ligand, by an enzyme immunoassay using a specific antibody, or the like.

Hereinafter, a screening method of the invention will be described in detail.

A method of screening a compound (an agonist, an antagonist etc.) that alters the binding property between the G protein-coupled receptor protein of the invention and a substance relating to cholesterol metabolism Using the protein of the invention, which contains a specific amino acid sequence (for example, the receptor protein of the invention, a partial peptide thereof, or salts thereof (hereinafter, sometimes referred to as the receptor protein of the invention)), or using the receptor binding assay system of the expression system constructed using the recombinant receptor protein etc., compounds (for example, peptides, proteins, non-peptide compounds, synthetic compounds, fermentation products, etc.) or salt thereof that alter the binding property between test compounds (for example, substances relating to cholesterol metabolism, which is a ligand (for example, bile acid (for example, taurolithocholic acid, glycolithocholic acid, taurodeoxycholic acid, glycodeoxycholic acid, nordeoxycholic acid, 7-ketolithocholic acid, 5β-pregnane-3,20-one, cholic acid, lithocholic acid, deoxycholic acid, taurocholic acid, glycocholic acid, chenodeoxycholic acid, ursodeoxycholic acid, taurochenodeoxycholic acid, glycochenodeoxycholic acid), epiandrosterone, (+)-4-androstene-3,17-dione, cis-androsterone, 11β-hydroxyprogesterone, 17α-hydroxyprogesterone, 11-deoxycorticosterone, 11-deoxycortizol, dehydroisoandrosterone, 3α-hydroxy-5α-pregnane-20-one, 4-pregnene-20α-ol-3-one, 5α-dehydroteststerone, teststerone, progesterone and salts thereof, etc.)) and the protein of the invention, can be efficiently screened.

Such test compounds include (a) compounds that have cell-stimulating activities (e.g., activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., activity that induces an expression of reporter gene), which are mediated by a certain protein (for example, G protein-coupled receptor protein), (so-called agonists to the receptor protein of the invention); (b) compounds that do not have the cell-stimulating activity (so-called antagonists to the receptor protein of the invention); (c) compounds that potentiate the binding affinity between physiologically active substances (for example, substances relating to cholesterol metabolism) and the G protein-coupled receptor protein of the invention; or (d) compounds that reduce the binding affinity between physiologically active substances (for example, substances relating to cholesterol metabolism) and the G protein-coupled receptor protein of the invention (it is preferred to screen the compounds described in (a) using the ligand determination methods described above).

In the invention, (1) a binding activity in the case of test compound 1 alone is assayed, and (2) further, a binding activity for test compound 2 is measured. Then, (3) the results of (1) and (2) are compared. That is, the present invention provides methods of screening compounds or their salts thereof that alter the binding property between substances relating to cholesterol metabolism and the receptor protein of the invention, its partial peptide or salts thereof, which comprises comparing (i) the case wherein the receptor protein of the invention, its partial peptide or salts thereof are brought in contact with substances relating to cholesterol metabolism, with (ii) the case wherein the receptor protein of the invention, its partial peptide or salts thereof are brought in contact with substances relating to cholesterol metabolism and test compounds.

The screening methods of the present invention are characterized by assaying, for example, the amount of substance relating to cholesterol metabolism bound to the receptor protein etc., the cell-stimulating activity, and the like, and comparing the property between (i) and (ii).

More specifically, the present invention provides the following screening methods:

(1) A method of screening a compound or its salt that alters the binding property between a substance relating to cholesterol metabolism and the receptor protein etc. of the invention, which comprises: measuring the amount of a labeled substances relating to cholesterol metabolism, bound to the receptor protein etc., when the labeled substance relating to cholesterol metabolism is brought in contact with the receptor protein etc. of the invention and when the labeled substance relating to cholesterol metabolism and a test compound are brought in contact with the receptor protein etc. of the invention, and comparing the binding property between them;

(2) A method of screening a compound or its salt that alters the binding property between a substance relating to cholesterol metabolism and the receptor protein etc. of the invention, which comprises: measuring the amount of a labeled substance relating to cholesterol metabolism bound to cells or the membrane fraction of the cells, when the labeled substance relating to cholesterol metabolism is brought in contact with the cells or cell membrane fraction containing the receptor protein etc. of the invention and when the labeled substance relating to cholesterol metabolism and a test compound are brought in contact with the cells or cell membrane fraction containing the receptor protein etc. of the invention, and comparing the binding property between them;

(3) A method of screening a compound or its salt that alters the binding property between a substance relating to cholesterol metabolism and the receptor protein etc. of the invention, which comprises measuring the amount of a labeled substance relating to cholesterol metabolism to the receptor protein etc., when the labeled substance relating to cholesterol metabolism is brought in contact with the receptor protein etc. expressed on the cell membrane induced by culturing a transformant containing the DNA of the invention and when the labeled substance relating to cholesterol metabolism and a test compound are brought in contact with the receptor protein etc. of the invention expressed on the cell membrane induced by culturing a transformant containing the DNA of the invention, and comparing the binding property between them;

(4) A method of screening a compound or its salt that alters the binding property between a substance relating to cholesterol metabolism and the receptor protein etc. of the invention, which comprises measuring the receptor-mediated cell-stimulating activity (e.g., the activity that promotes or suppresses arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., the activity that induces an expression of reporter gene), when a compound (e.g., a substance relating to cholesterol metabolism for the receptor protein etc. of the invention) that activates the receptor protein etc. of the invention is brought in contact with cells containing the receptor protein etc. of the invention and when the compound that activates the receptor protein etc. of the invention and a test compound are brought in contact with cells containing the receptor protein etc. of the invention, and comparing the binding property between them; and, (5) A method of screening a compound or its salt that alters the binding property between a substance relating to cholesterol metabolism and the receptor protein etc. of the invention, which comprises measuring the receptor-mediated cell-stimulating activity (e.g., the activity that promotes or suppresses arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., the activity that induces an expression of reporter gene), when a compound (e.g., a substance relating to cholesterol metabolism for the receptor protein etc. of the invention) that activates the receptor protein etc. of the invention is brought in contact with the receptor protein etc. of the invention expressed on the cell membrane induced by culturing a transformant containing the DNA of the invention and when the compound that activates the receptor protein etc. of the invention and a test compound are brought in contact with the receptor protein etc. of the invention expressed on the cell membrane induced by culturing a transformant containing the DNA of the invention, and comparing the binding property between them.

First, for the receptor protein etc. of the present invention used for the screening methods of the present invention, any substance may be used so long as it contains the receptor protein etc. of the present invention described above. The cell membrane fraction from mammalian organs containing the receptor protein etc. of the present invention is preferred. However, it is very difficult to obtain human organs. It is thus preferable to use rat-derived receptor proteins or the like, produced by large-scale expression using recombinants.

To manufacture the receptor protein etc. of the present invention, the methods described above are used, and it is preferred to express the DNA of the present invention in mammalian and insect cells. For the DNA fragment encoding the objective protein region, the complementary DNA, but not necessarily limited thereto, is employed. For example, the gene fragments and synthetic DNA may also be used. To introduce a DNA fragment encoding the receptor protein of the present invention into host animal cells and efficiently express the DNA there, it is preferred to insert the DNA fragment downstream of a polyhedorin promoter of nuclear polyhedrosis virus (NPV) belonging to baculovirus hosted by insects, SV40-derived promoter, retrovirus promoter, metallothionein promoter, human heat shock promoter, cytomegalovirus promoter, or SRα promoter. The amount and quality of the expressed receptor are examined by publicly known methods, for example, the method described in the literature [Nambi, P. et al., The Journal of Biological Chemistry (J. Biol. Chem.), 267, 19555–19559, 1992].

Therefore, in the screening methods of the present invention, the material that contains the receptor protein etc. of the present invention may be the receptor protein etc. purified by publicly known methods, cells containing the receptor protein etc., or the cell membrane fraction containing the receptor protein or the like.

In the screening methods of the present invention, when cells containing the receptor protein etc. of the present invention are used, the cells may be fixed with glutaraldehyde, formalin, etc. The cells can be fixed by publicly known methods.

The cells containing the receptor protein etc. of the present invention are host cells that express the receptor protein or the like. For the host cells, *Escherichia coli*, *Bacillus subtilis*, yeast, insect cells, animal cells and the like are preferred.

The cell membrane fraction refers to a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor protein etc. expressed and membrane components such as cell-derived phospholipids and membrane proteins.

The amount of the receptor protein in the cells containing the receptor protein etc. and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To screen the compounds that alter the binding property between substance relating to cholesterol metabolism and the receptor protein etc. of the invention described in (1) to (3), for example, an appropriate receptor protein fraction and a labeled substance relating to cholesterol metabolism are necessary.

The receptor protein fraction is preferably a fraction of naturally occurring receptor protein or a recombinant receptor fraction having an activity equivalent to that of the natural protein. Herein, the equivalent activity is intended to mean a ligand binding activity, a signal transduction activity or the like that is equivalent to that possessed by naturally occurring receptor proteins.

For the labeled substance relating to cholesterol metabolism, a labeled substance relating to cholesterol metabolism and a labeled substance relating to cholesterol metabolism analogue are used. For example, substances relating to cholesterol metabolism, which is labeled with $[^3H]$, $[^{251}I]$, $[^{14}C]$, $[^{35}S]$, etc., are used.

Specifically, to screen the compounds that alter the binding property between substances relating to cholesterol metabolism and the receptor protein etc. of the invention, first, the receptor protein standard is prepared by suspending cells or cell membrane fraction containing the receptor protein etc. of the invention in a buffer appropriate for the screening. For the buffer, any buffer that does not interfere with the binding of ligands to the receptor protein is usable and examples of such a buffer are phosphate buffer, Tris-hydrochloride buffer, etc., having pH of 4 to 10 (preferably pH of 6 to 8). To minimize a non-specific binding, a surfactant such as CHAPS, Tween-80™ (Kao-Atlas Co.), digitonin, deoxycholate, etc. may be added to the buffer. To inhibit degradation of the receptor and ligands by proteases, protease inhibitors such as PMSF, leupeptin, E-64 (manufactured by Peptide Research Laboratory, Co.), and pepstatin can be added. To 0.01 to 10 ml of the receptor solution, a given amount (5,000 to 500,000 cpm) of labeled substance relating to cholesterol metabolism is added, and $10^{-4}$ M–$10^{-10}$ M of a test compound is simultaneously added to be co-present. To examine non-specific binding (NSB), a reaction tube containing an unlabeled substance relating to cholesterol metabolism in large excess is also prepared. The reaction is carried out at approximately 0° C. to 50° C., preferably about 4° C. to 37° C. for about 20 minutes to about 24 hours, preferably about 30 minutes to about 3 hours. After completion of the reaction, the reaction mixture is filtrated through glass fiber filter paper and washed with an appropriate volume of the same buffer. The residual radioactivity on the glass fiber filter paper is then measured by means of a liquid scintillation counter or γ-counter. Regarding the count obtained by subtracting the amount of non-specific binding (NSB) from the count obtained in the absence of any competitive substance ($B_0$) as 100%, when the amount of specific binding (B-NSB) is, for example, 50% or less, the test compound can be selected as a candidate substance having a potential of competitive inhibition.

To perform the methods (4) and (5) above of screening the compounds that alter the binding property between substance relating to cholesterol metabolism and the receptor protein etc. of the invention, the receptor protein-mediated cell-stimulating activity (e.g., activity that promotes or inhibits arachidonic acid release, acetylcholine release, intracellular Ca release, intracellular cAMP production, intracellular cGMP production, inositol phosphate production, changes in cell membrane potential, phosphorylation of intracellular proteins, activation of c-fos, pH reduction, etc., activity that induces an expression of reporter gene) can be measured using publicly known methods or commercially available kits.

Specifically, the cells containing the receptor protein etc. of the invention are first cultured on a multi-well plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the substance used as an index (e.g., arachidonic acid) for the cell-stimulating activity due to a degrading enzyme contained in the cells, an inhibitor against such a degrading enzyme may be added prior to the assay. For detecting activities such as the suppression activity of cAMP production, the baseline production in the cells is increased by forskolin or the like and the suppressing effect on the increased baseline production can then be detected.

Screening by assaying the cell-stimulating activity requires cells that have expressed an appropriate receptor protein. For the cells that have expressed the receptor protein etc. of the invention, the cell line possessing the native receptor protein etc. of the invention, the cell line expressing the recombinant receptor protein described above and the like are desirable.

For the test compounds, for example, peptides, proteins, non-peptide compounds, synthetic compounds, fermentation products, cell extracts, plant extracts, and animal tissue extracts are used. These compounds may be novel or publicly known compounds.

The kits for screening the compounds or their salts that alter the binding property between substances relating to cholesterol metabolism and the receptor protein etc. of the invention comprise the receptor protein etc. of the invention, cells containing the receptor protein etc. of the invention, or the membrane fraction of cells containing the receptor protein etc. of the invention.

Examples of the screening kits of the invention are as follow.

1. Reagents for Screening (1) Buffers for Measurement and Washing

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.

(2) Standard G Protein-Coupled Receptor

CHO cells expressing the receptor protein of the invention are passaged in a 12-well plate at a density of $5 \times 10^5$ cells/well followed by culturing at 37° C. under 5% $CO_2$ and 95% air for 2 days.

(3) Standard Substances Relating to Cholesterol Metabolism

Substances relating to cholesterol metabolism labeled with commercially available [$^3$H], [$^{125}$I], [$^{14}$C], [$^{35}$S], etc.

Aqueous solution are stored at 4° C. or −20° C., and diluted to 1 μM with the measurement buffer.

(4) Standard Solution of Substances Relating to Cholesterol Metabolism

The substance relating to cholesterol metabolism is dissolved in PBS containing 0.1% bovine serum albumin (manufactured by Sigma Co.), adjusted to 1 mM with the above buffer and stored at −20° C.

2. Measurement Method (1) CHO cells expressing the receptor protein of the invention are cultured in a 12-well culture plate and washed twice with 1 ml of the measurement buffer, and 490 μl of the measurement buffer is added to each well.

(2) After adding 5 μl of $10^{-3}$–$10^{-10}$ M test compound solution, 5 μl of a labeled substance relating to cholesterol metabolism is added to the mixture, and the cells are incubated at room temperature for an hour. To determine the amount of the non-specific binding, 5 μl of $10^{-3}$ M substances relating to cholesterol metabolism is added in place of the test compound.

(3) The reaction solution is removed, and the wells are washed 3 times with the washing buffer. The labeled ligand bound to the cells is dissolved in 0.2N NaOH-1% SDS, and mixed with 4 ml of liquid scintillator A (manufactured by Wako Pure Chemical Industries, Ltd.)

(4) The radioactivity is measured using a liquid scintillation counter (manufactured by Beckman Co.), and the percent maximum binding (PMB) is calculated by the equation below.

$$PMB = [(B - NSB)/(B_0 - NSB)] \times 100$$

PMB: Percent maximum binding
B: Value obtained in the presence of a specimen
NSB: Non-specific binding
$B_0$: Maximum binding The compounds or their salts, which are obtained using the screening methods or the screening kits. of the invention, are the compounds that alter the binding property between substances relating to cholesterol metabolism and the receptor protein etc. of the invention. Specifically, these compounds are: (a) compounds that have the G protein-coupled receptor-mediated cell-stimulating activity (e.g., activity that promotes or inhibits arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., activity that induces an expression of reporter gene) (so-called agonists to the receptor protein of the invention); (b) compounds having no cell stimulating-activity (so-called antagonists to the receptor protein of the invention); (c) compounds that potentiate the binding affinity between substance relating to cholesterol metabolism and the G protein-coupled receptor protein of the invention; and (d) compounds that reduce the binding affinity between substance relating to cholesterol metabolism and the G protein-coupled receptor protein of the invention.

For the compounds, peptides, proteins, non-peptide compounds, synthetic compounds, fermentation products are included, and it may be novel or publicly known compounds.

Since agonists to the receptor protein etc. of the invention have the same physiological activities as those of the substances relating to cholesterol metabolism for the receptor protein etc. of the invention, the agonists are useful as safe and low toxic medicines, correspondingly to the activities, which the substance relating to cholesterol metabolism has.

Since antagonists to the receptor protein etc. of the invention can suppress the physiological activities of substances relating to cholesterol metabolism for the receptor protein etc. of the invention, the antagonists are useful as safe and low toxic medicines that inhibit the activities, which the substance relating to cholesterol metabolism has.

The compounds that potentiate the binding affinity between substances relating to cholesterol metabolism and the G protein-coupled receptor protein of the invention are useful as safe and low toxic medicines to potentiate the physiological activities that the substances relating to cholesterol metabolism for the receptor protein etc. of the invention possess.

The compounds that reduce the binding affinity between substances relating to cholesterol metabolism and the G protein-coupled receptor protein of the invention are useful as safe and low toxic medicines that reduce the physiological activities of substance relating to cholesterol metabolism for the receptor protein etc. of the invention.

For example, it is useful as a prophylactic and/or therapeutic agent for diseases such as central diseases (e.g., Alzheimer's disease, dementia, eating disorder), inflammatory diseases (e.g., allergy, rheumatism, osteoarthritis, erythematosus), circulatory diseases (e.g., hypertension, cardiac hypertrophy, cardiac angina, arteriosclerosis), cancer (e.g., non-small-cell lung cancer, ovarian cancer, prostate cancer, stomach cancer, bladder carcinoma, breast cancer, cancer of uterine cervix, colon cancer, rectum cancer), respiratory diseases (e.g., pneumonia, bronchitis, asthma, pulmonary fibrosis), diabetes, immune system diseases (e.g., Crohn's disease, atopic dermatitis, autoimmune disease, immunodeficiency, leukemia), diseases of liver and cholecyst (e.g., liver cirrhosis, hepatitis, liver failure, cholestasis, calculosis), alimentary diseases (e.g., ulcer, enterisis, malabsorption), infectious diseases, adiposis, hyperimmuno reaction after transplantation.

Among these diseases, against diseases caused by enhancement of immune function, function of macrophage or the like (e.g., inflammatory diseases, hyperimmuno reaction after transplantation), the compound that potentiates a physiological activity through the receptor protein of the invention (e.g., agonist) is particularly useful.

On the other hand, against diseases caused by suppression of immune function, function of macrophage or the like (e.g., immunodeficiency, infectious disease), the compound that reduces a physiological activity through the receptor protein of the invention (e.g., antagonist) is particularly useful.

When the compound or its salt, which is obtained by the screening methods or using the screening kits of the present invention, is employed as a pharmaceutical (composition) described above, it can be formulated in the drugs in a conventional manner.

For example, the compounds or salts thereof can be administered orally as sugar coated tablet, capsule, elixir, and microcapsule, or non-orally as injection such as aseptic solution or suspension in water or other pharmaceutically acceptable liquid. For example, the compounds or salts thereof can be manufactured by mixing with physiologically acceptable known carrier, flavor, filler, vehicle, antiseptic, stabilizer, and binder in a unit-dosage form required for generally approved drug preparation. The amount of the active ingredient is set to an appropriate volume within the specified range.

For the additive miscible with tablets, capsules, etc., for example, binders such as gelatin, cornstarch, tragacanth, and acacia, fillers such as crystalline cellulose, imbibers such as cornstarch, gelatin, and alginic acid, lubricants such as magnesium stearate, sweeteners such as sucrose and saccharin, and flavors such as peppermint, akamono oil and cherry are used. When the dosage form is a capsule, liquid carrier such as fat and oil may be contained. Aseptic compositions for injection can be formulated following the usual preparation such as dissolving or suspending the active substance in vehicle, e.g., water for injection, and natural plant oils e.g., sesame oil and coconut oil. For the aqueous solution for injection, for example, physiological saline and isotonic solutions (e.g., D-sorbitol, D-mannitol, sodium hydrochloride) containing glucose and other adjuvant are used. Appropriate dissolution-assisting agents, for example, alcohol (e.g., ethanol), polyalcohol (e.g., propylene glycol, polyethylene glycol), nonionic surfactant (e.g., polysorbate 80™, HCO-50) may be combined. For the oily solution, for example, sesame oil and soybean oil are used, and dissolution-assisting agents such as benzyl benzoate and benzyl alcohol may be combined.

The prophylactic/therapeutic agents described above may be combined, for example, with buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol), and antioxidants. The preparation for injection is usually filled in appropriate ampoules.

The drug products thus obtained are safe and low toxic, and can be administered to, for example, human and other mammals (e.g., rats, mice, rabbits, sheep, swine, bovine, cats, dogs, monkeys).

The dose of the compounds or salts thereof varies depending on subject to be administered, target organs, symptoms, routes for administration, etc.; in oral administration, e.g, for the patient with hypertension, the dose is normally about 0.1 to about 100 mg, preferably about 1.0 to about 50 mg, and more preferably about 1.0 to about 20 mg per day (as 60 kg body weight). In parenteral administration, the single dose varies depending on subject to be administered, target organ, symptoms, routes for administration, etc. but it is advantageous, e.g., for the patient with hypertension, to administer by intravenous injection in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

Further, a method of quantifying a ligand to the G protein-coupled receptor protein of the invention will be described below.

The receptor protein of the invention, etc. has a binding property to substances relating to chlesterol metabolism (e.g., bile acid (for example, taurolithocholic acid, glycolithocholic acid, taurodeoxycholic acid, glycodeoxycholic acid, nordeoxycholic acid, 7-ketolithocholic acid, 5β-pregnane-3, 20-one, cholic acid, lithocholic acid, deoxycholic acid, taurocholic acid, glycocholic acid, chenodeoxycholic acid, ursodeoxycholic acid, taurochenodeoxycholic acid, glycochenodeoxycholic acid), epiandrosterone, (+)-4-androstene-3,17-dione, cis-androsterone, 11β-hydroxyprogesterone, 17α-hydroxyprogesterone, 11-deoxycorticosterone, 11-deoxycortizol, dehydroisoandrosterone, 3α-hydroxy-5α-pregnane-20-one, 4-pregnene-20α-ol-3-one, 5α-dehydroteststerone, teststerone, progesterone and salts thereof). Thus, a concentration of the substances relating to chlesterol metabolism in the living body can sensitively be quantified.

The quantification methods of the invention can be used in combination with, for example, a competitive method. The concentration of the substances relating to chlesterol metabolism in a test sample can be measured by contacting the test sample to the receptor protein etc. of the invention. Specifically, the methods can be used in accordance with, for example, the methods described in (i) and (ii) below or its modified methods.

(i) Hiroshi Irie, ed. "Radioimmunoassay," Kodansha, published in 1974

(ii) Hiroshi Irie, ed. "Sequel to the Radioimmunoassay," Kodansha, published in 1979

In the present invention, a method of quantifying a ligand to the receptor protein wherein the ligand is unknown will be described below in detail.

The method of determining a ligand in the present invention includes (1) a method that measures an activity of a reporter protein, in which the expression is induced by adding a test compound to cells expressing a ligand-undetermined receptor protein and containing a plasmid, to which a DNA encoding the receptor protein is ligated downstream enhancer/promoter, (2) a method that measures an activity of a reporter protein, in which the expression is induced by culturing cells containing (i) a plasmid containing a DNA encoding a ligand-undetermined receptor protein, and (ii) a plasmid ligating a DNA encoding a reporter protein downstream enhancer/promoter, and adding a test compound.

For the receptor protein, for example, a G protein-coupled receptor protein and the like can be used. Specific examples include the G protein-coupled receptor protein containing the same or substantially the same amino acid sequence as the amino acid sequence represented by SEQ ID NO: 1, the G protein-coupled receptor protein described in WO 96/05302, EP-A-711831, EP-A-789076, EP-A-1103563, EP-A-1103562, Patent Kokai number Hei8-154682 Publication, Patent Kokai number Hei8-283295 Publication, Patent Kokai number Hei8-196278 Publication, Patent Kokai number Hei8-245697 Publication, Patent Kokai number Hei8-266280 Publication, Patent Kokai number Hei9-51795 Publication, Patent Kokai number Hei9-121865 Publication, Patent Kokai number Hei9-2388686 Publication, and Patent Kokai number Hei10-146192 Publication, and the like.

For the receptor-expressing plasmid, a plasmid containing a promoter for the expression of the receptor protein in eukaryotic cells, a drug resistance gene (e.g, ampicilin resistant gene) that can be used as a selection marker in the case of amplification in prokaryote, and the like.

For the plasmid transducible to the (eukaryotic) cells containing the DNA encoding the receptor protein downstream enhancer/promoter, any plasmid such as a commercially available plasmid may be usable. Preferably a plasmid containing an enzyme gene, wherein the enzyme activity can be detected by a publicly known method, can be used.

For the enhancer, for example, SV40, enhancer derived from virus such as papillomavirus, etc., LTR of retrovirus, and cAMP response element (CRE), preferably cAMP response element may be used.

For the promoter, for example, SV40 promoter, CMV promoter, TATA-like promoter of thymidine kinase gene in HSV and the like, preferably TATA-like promoter may be used.

For the reporter gene, for example, luciferase gene, β-galactosidase gene, GFP gene, alkaline phosphatase gene, and the like can be used.

For a specific example of the plasmid, a plasmid ligating a TATA-like promoter and a gene encoding the reporter protein (e.g, luciferase gene) downstream cAMP response element such as pCRE-Luc (Clontech) can be used.

The cells used in the above include eukaryotic cells, and preferably animal cells (e.g, simian cell COS-7, Vero, CHO cell, CHO (dhfr⁻) cell, mouse L cell, mouse AtT-20, mouse myeloma cell, rat GH3, human FL cell, human HEK293 cell) and the like can be used.

Two or more (preferably two or three) receptor proteins may be expressed in the cells.

Where two or more receptor proteins may be expressed, two or more receptor proteins, which have similar properties, may be selected.

Example of similar properties includes an expression level of the reporter gene when two or more receptor proteins are expressed independently. Specifically, using (i) a basic expression level of the reporter gene, and/or (ii) an expression level of the reporter gene in the case of addition of forskolin as indices when two or more receptor proteins are expressed independently, the properties of respective receptor proteins can be distinguished.

In other words, where a ligand can be determined by expressing two or more ligand-undetermined receptor proteins, it is desirable that the basic expression level of the reporter gene may previously be classified into groups such as low, medium or distinctly high, or that a receptor protein, which is difficult to increase its expression level by the addition of forskolin, may be elucidated. When two receptor proteins, one with a high basic expression level of reporter protein and the other with a low basic expression level of reporter protein, will be expressed, an increase of the expression level of the reporter protein becomes to be blind in the case where the latter is a ligand. Therefore, based on the obtained information, it is preferred that:

(1) The combination of two receptor proteins, one with a high basic expression level of reporter protein and the other with a low basic expression level of reporter protein, may be avoided;
(2) The combination of two receptor proteins, one with significant increase of the expression level of the reporter protein by the addition of forskolin and the other without increase of the expression level of the reporter protein, may be avoided;
(3) By the combination of the receptor proteins with the same level of basic expression of the reporter protein, the expression may be performed.

Example of the combination of the receptor proteins, which possess the similar properties, includes a combination with APJ (apelin receptor; Gene Vol. 136, p. 355 (1993)) and TGR-1 (Patent Kokai 2002-078492).

Specific example of a method for determining a ligand will be described below.

The cells are seeded in a 96-well plate and cultured for example, in DMEM containing 10% fetal bovine serum for overnight. At this time, using a commercially available transfection kit, the cells are cotransfected with a receptor protein-expressing plasmid and a reporter plasmid. By culturing the cells for more overnight, the receptor protein may transiently express in the cells. After the cells are washed and the medium becomes to be serum-free, a test compound is added. Where the enhancer is CRE, forskolin may be added simultaneously with the test compound. After incubation for a given time, the cells are lysed and the activity of the reporter protein is assayed.

In the aforementioned method, when signal detection is difficult owing to a high baseline, one may take steps to reduce the baseline. For example, when the receptor protein is a G protein-coupled receptor protein (GPCR), by adding Gi protein, which exhibits an inhibitory effect against cAMP, among Gα proteins that is a subunit of G protein, it becomes to be easy to detect a signal. A Gi protein can also be introduced into the cells as a plasmid expressing a DNA encoding the Gi protein with a receptor protein-containing plasmid and a reporter plasmid. In this case, a mixing ratio of three plasmids (receptor plasmid: reporter plasmid: Gi plasmid) is preferred to be insofar as 5–15:1:1–6, more preferably, 7:1:3.

Antibodies to the receptor protein of the invention, its partial peptides, or salts thereof may be any of polyclonal antibodies and monoclonal antibodies, as long as they are capable of recognizing the receptor protein of the present invention, its partial peptides, or salts thereof.

The antibodies to the receptor protein of the invention, its partial peptides, or salts thereof (hereinafter sometimes merely referred to as the receptor protein of the invention) may be manufactured by publicly known methods for manufacturing antibodies or antisera, using as antigens the receptor protein of the invention.

[Preparation of Monoclonal Antibody]

(a) Preparation of Monoclonal Antibody-Producing Cells

The receptor protein of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable mammals are monkeys, rabbits, dogs, guinea pigs, mice, rats, sheep and goats, with mice and rats being preferred.

In the preparation of monoclonal antibody-producing cells, warm-blooded animals, e.g, mice, immunized with an antigen wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled form of the receptor protein, which will be described later, with the antiserum followed by assaying the binding activity of the labeling agent bound to the antibody. The fusion may be operated, for example, by the known Koehler and Milstein method (Nature, 256, 495, 1975). Examples of the fusion accelerator are polyethylene glycol (PEG), Sendai virus, etc., of which PEG is preferably employed.

Examples of the myeloma cells are NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to about 40° C., preferably at about 30 to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g, microplate) adsorbed with the receptor protein etc. as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the receptor protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g, DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

[Preparation of Polyclonal Antibody]

The polyclonal antibody of the present invention can be manufactured by publicly known methods or modifications thereof. For example, a complex of immunogen (antigen such as the receptor protein) and a carrier protein is prepared, and a mammal is immunized with the complex in a manner similar to the method described above for the manufacture of monoclonal antibodies. The product containing the antibody to the receptor protein of the present invention is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warm-blooded animals either solely or together with carriers or diluents to the site in which the antibody can be produce by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

The G protein-coupled receptor protein of the invention containing the same or substantially the same amino acid sequence as the amino acid sequence represented by SEQ ID NO: 5, SEQ ID NO: 7, SEQ ID NO: 14 or SEQ ID NO: 16 (except for the amino acid sequence represented by SEQ ID NO: 1), its salts, its partial peptides or salts thereof, and the DNA encoding the receptor protein or the partial peptide are a novel substance, and can be used for (1) prophylactic and/or therapeutic agents for diseases associated with dysfunction of the G protein-coupled receptor protein of the invention, (2) agents for gene diagnosis, (3) prophylactic and/or therapeutic agents for various diseases comprising a compound that alters the expression level of the receptor protein of the invention or partial peptides thereof, (4) methods of quantification of ligands to the G protein-coupled receptor protein of the invention, (5) prophylactic and/or therapeutic agents for various diseases comprising a compound (an agonist or an antagonist) that alters the binding property between the G protein-coupled receptor protein of the invention and ligands, (6) quantification of the receptor protein of the invention, its partial peptides or salts thereof, (7) prophylactic and/or therapeutic agents for various diseases comprising a compound that alters the amount of the receptor protein of the invention or its partial peptides in cell membranes, (8) neutralization by antibodies to the receptor protein of the invention, its partial peptides, or salts thereof, and (9) preparation of non-human animals that possess the DNA encoding the G protein-coupled receptor protein of the invention.

Hereinafter, the receptor protein of the invention, its partial peptides, or salts thereof (hereinafter sometimes referred to as the receptor protein of the invention), the DNA encoding the receptor protein of the invention or its partial peptides (hereinafter sometimes referred to as the DNA of the invention) and the antibodies to the receptor protein of the invention (hereinafter sometimes referred to as the antibodies of the invention) are specifically described for the use or applications.

(1) Prophylactic and/or Therapeutic Agents for Diseases Associated with Dysfunction of the G Protein-Coupled Receptor Protein of the Invention Depending on the activities possessed by the ligand to the receptor protein of the invention, (i) the receptor protein of the invention, or (ii) the DNA encoding the receptor protein can be used as a prophylactic and/or therapeutic agent for diseases associated with dysfunction of the receptor protein of the invention.

For example, when the physiological activity of the ligand cannot be expected in a patient (deficiency of the receptor protein) due to a decrease in the receptor protein of the present invention, the activity of the ligand can be exhibited by: (i) administering the receptor protein of the present invention to the patient thereby to supplement the amount of the receptor protein; or (ii) by increasing the amount of the receptor protein in the patient through: i) administration of the DNA encoding the receptor protein of the present invention to express the same in the patient; or ii) insertion and expression of the DNA encoding the receptor protein of the present invention in the objective cells to transplant the cells to the patient, whereby the activity of the ligand can be sufficiently exhibited. That is, the DNA encoding the receptor protein of the present invention is useful as a safe and low toxic prophylactic and/or therapeutic agent for diseases associated with dysfunction of the receptor protein of the present invention.

For example, the receptor protein of the invention is useful as a prophylactic and/or therapeutic agent for diseases such as central diseases (e.g, Alzheimer's disease, dementia, eating disorder), inflammatory diseases (e.g, allergy, rheumatism, osteoarthritis, erythematosus), circulatory diseases (e.g, hypertension, cardiac hypertrophy, cardiac angina, arteriosclerosis), cancer (e.g, non-small-cell lung cancer, ovarian cancer, prostate cancer, stomach cancer, bladder carcinoma, breast cancer, cancer of uterine cervix, colon cancer, rectum cancer), respiratory diseases (e.g, pneumonia, bronchitis, asthma, pulmonary fibrosis), diabetes, immune system diseases (e.g, Crohn's disease, atopic dermatitis, autoimmune disease, immunodeficiency, leukemia), diseases of liver and cholecyst (e.g, liver cirrhosis, hepatitis, liver failure, cholestasis, calculosis), alimentary diseases (e.g, ulcer, enterisis, malabsorption), infectious diseases (e.g, adiposis, hyperimmuno reaction after transplantation).

Among these diseases, against diseases caused by enhancement of immune function, function of macrophage or the like (e.g, inflammatory diseases, hyperimmuno reaction after transplantation), the compound that potentiates a physiological activity through the receptor protein of the invention (e.g, agonist) is particularly useful.

On the other hand, against diseases caused by suppression of immune function, function of macrophage or the like (e.g, immunodeficiency, infectious disease), the compound that reduces a physiological activity through the receptor protein of the invention (e.g, antagonist) is particularly useful.

When the receptor protein of the invention is used as the prophylactic and/or therapeutic agents described above, the receptor protein can be prepared into a drug product in a conventional manner.

On the other hand, where the DNA encoding the receptor protein of the invention (hereinafter sometimes referred to as the DNA of the invention) is used as the prophylactic and/or therapeutic agents described above, the DNA itself is administered; alternatively, the DNA is inserted into an appropriate vector such as retrovirus vector, adenovirus vector, adenovirus-associated virus vector, etc. and then administered in a conventional manner. The DNA of the present invention may also be administered as naked DNA, or with adjuvants to assist its uptake by gene gun or through a catheter such as a catheter with a hydrogel.

For example, (i) the receptor protein of the invention or (ii) the DNA encoding the receptor protein can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing (i) the receptor protein of the invention or (ii) the DNA encoding the receptor protein with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The effective component in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g, D-sorbitol, D-mannitol, sodium chloride, etc.) and may be used in combination with an appropriate dissolution aid such as an alcohol (e.g., ethanol or the like), a polyalcohol (e.g, propylene glycol and polyethylene glycol), a nonionic surfactant (e.g, polysorbate 80™ and HCO-50), etc. Examples of the oily medium include sesame oil and soybean oil, which may also be used in combination with a dissolution aid such as benzyl benzoate and benzyl alcohol.

The prophylactic and/or therapeutic agent described above may further be formulated with a buffer (e.g., phosphate buffer, sodium acetate buffer, etc.), a soothing agent (e.g, benzalkonium chloride, procaine hydrochloride, etc.), a stabilizer (e.g., human serum albumin, polyethylene glycol, etc.), a preservative (e.g, benzyl alcohol, phenol, etc.), an antioxidant, etc. The thus-prepared liquid for injection is normally filled in an appropriate ampoule.

Since the thus obtained pharmaceutical preparation is safe and low toxic, the preparation can be administered to human and other mammals (e.g, rats, mice, rabbits, sheep, swine, bovine, cats, dogs, monkeys, etc.).

The dose of the receptor protein of the present invention varies depending on subject to be administered, organs to be administered, conditions, routes for administration, etc.; in oral administration, e.g, for the patient with hypertension, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g, for the patient with hypertension, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

The dose of the DNA of the present invention varies depending on subject to be administered, organs to be administered, conditions, routes for administration, etc.; in oral administration, e.g, for the patient with hypertension, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g, for the patient with hypertension, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(2) Agents for Gene Diagnosis

By using the DNA of the invention as a probe, an abnormality (gene abnormality) of the DNA or mRNA encoding the receptor protein of the invention or its partial peptide in human or other mammals (e.g, rats, mice, rabbits, sheep, swine, bovine, cats, dogs, monkeys, etc.) can be detected. Therefore, the DNA of the invention is useful as a gene diagnostic agent for the damage against the DNA or mRNA, its mutation, or its decreased expression, or increased expression or overexpression of the DNA or mRNA. More specifically, it is useful as a gene diagnostic agent for diseases such as central diseases (e.g. Alzheimer's disease, dementia, eating disorder), inflammatory diseases (e.g, allergy, asthma, rheumatism), circulatory diseases (e.g, hypertension, cardiac hypertrophy, cardiac angina, arteriosclerosis), cancer (e.g, non-small-cell lung cancer, ovarian cancer, prostate cancer, stomach cancer, bladder carcinoma, breast cancer, cancer of uterine cervix, colon cancer, rectum cancer), diabetes, immune system diseases (e.g, autoimmune disease, immunodeficiency, leukemia), diseases of liver and cholecyst (e.g, liver cirrhosis, hepatitis, liver failure, cholestasis, calculosis), alimentary diseases (e.g, ulcer, enterisis, malabsorption), adiposis.

The gene diagnosis described above using the DNA of the present invention can be performed by, for example, the publicly known Northern hybridization assay or the PCR-SSCP assay (Genomics, 5, 874–879 (1989); Proceedings of the National Academy of Sciences of the United States of America, 86, 2766–2770 (1989)).

(3) Prophylactic and/or Therapeutic Agents for Various Diseases Comprising the Compounds that Alter the Expression Level of the Receptor Protein of the Invention or its Partial Peptide As described above, the receptor protein of the present invention is considered to play some important role such as a role in the central function. Therefore, the compounds that alter the expression level of the receptor protein of the invention or its partial peptide is useful as prophylactic and/or therapeutic agents for diseases associated with dysfunction of the receptor protein of the invention, such as central diseases (e.g, Alzheimer's disease, dementia, eating disorder), inflammatory diseases (e.g, allergy, rheumatism, osteoarthritis, erythematosus), circulatory diseases (e.g, hypertension, cardiac hypertrophy, cardiac angina, arteriosclerosis), cancer (e.g, non-small-cell lung cancer, ovarian cancer, prostate cancer, stomach cancer, bladder carcinoma, breast cancer, cancer of uterine cervix, colon cancer, rectum cancer), respiratory diseases (e.g, pneumonia, bronchitis, asthma, pulmonary fibrosis), diabetes, immune system diseases (e.g, Crohn's disease, atopic dermatitis, autoimmune disease, immunodeficiency, leukemia), diseases of liver and cholecyst (e.g, liver cirrhosis, hepatitis, liver failure, cholestasis, calculosis), alimentary diseases (e.g, ulcer, enterisis, malabsorption), infectious diseases, adiposis, hyperimmuno reaction after transplantation.

Among these diseases, against diseases caused by enhancement of immune function, function of macrophage or the like (e.g, inflammatory diseases, hyperimmuno reaction after transplantation), the compound that potentiates a physiological activity through the receptor protein of the invention (e.g, agonist) is particularly effective.

On the other hand, against diseases caused by suppression of immune function, function of macrophage or the like (e.g, immunodeficiency, infectious disease), the compound that reduces a physiological activity through the receptor protein of the invention (e.g, antagonist) is particularly effective.

When the compounds are used as the prophylactic and/or therapeutic agents for diseases associated with dysfunction of the receptor protein of the invention, the compound can be prepared into a drug product in a conventional manner.

For example, the compounds can be administered orally as a sugar coated tablet, capsule, elixir, and microcapsule, or non-orally as injection such as aseptic solution or suspension in water or other pharmaceutically acceptable liquid. For example, preparations of the compounds can be manufactured by mixing with physiologically acceptable known carrier, flavor, filler, vehicle, antiseptic, stabilizer, and binder in a unit-dosage form required for generally approved drug preparation. The amount of the active ingredient is set to an appropriate volume within the specified range.

For the additive miscible with tablets and capsules, for example, binders such as gelatin, cornstarch, tragacanth, and acacia, fillers such as crystalline cellulose, imbibers such as cornstarch, gelatin, and alginic acid, lubricants such as magnesium stearate, sweeteners such as sucrose and saccharin, and flavors such as peppermint, akamono oil and cherry are used. When the dosage form is a capsule, liquid carrier such as fat and oil may be contained. Aseptic compositions for injection can be formulated following the usual preparation procedure such as dissolving or suspending the active substance in vehicle, e.g., water for injection, and natural plant oils e.g., sesame oil and coconut oil. For the aqueous solution for injection, for example, physiological saline and isotonic solutions (e.g, D-sorbitol, D-mannitol, sodium hydrochloride) containing glucose and other adjuvant are used. Appropriate dissolution-assisting agents, for example, alcohol (e.g., ethanol), polyalcohol (e.g., propylene glycol, polyethylene glycol), nonionic surfactant (e.g, polysorbate 80™, HCO-50) may be combined. For the oily solution, for example, sesame oil and soybean oil are used, and dissolution-assisting agents such as benzyl benzoate and benzyl alcohol may be combined.

The prophylactic and/or therapeutic agents described above may be combined with buffers (e.g, phosphate buffer, sodium acetate buffer), soothing agents (e.g, benzalkonium chloride, procaine hydrochloride), stabilizers (e.g., human serum albumin, polyethylene glycol), preservatives (e.g., benzyl alcohol, phenol), antioxidants, and the like. The preparation for injection is usually filled in appropriate ampoules.

The preparations obtained as described above are safe and low toxic, and can be administered to, for example, human and other mammals (e.g, rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g. for the patient with hypertension, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g, for the patient with hypertension, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(4) Methods of Quantification of Ligands to the G Protein-Coupled Receptor Protein of the Invention Since the receptor protein etc. of the present invention has binding affinity to ligands, the ligand concentration can be quantified in vivo with good sensitivity.

The quantification methods of the present invention can be used in combination with, for example, a competitive method. The ligand concentration in a test sample can be measured by contacting the test sample to the receptor protein etc. of the present invention. Specifically, the methods can be used by the followings, for example, the methods described in (i) and (ii) below or its modified methods.

(i) Hiroshi Irie, ed. "Radioimmunoassay," Kodansha, published in 1974

(ii) Hiroshi Irie, ed. "Sequel to the Radioimmunoassay," Kodansha, published in 1979

(5) Prophylactic and/or Therapeutic Agents for Various Diseases Comprising the Compounds (Agonists or Antagonists) that Alter the Binding Property Between the G Protein-Coupled Receptor Protein of the Invention and Ligands As described above, the receptor protein of the invention may play some important role in the body such as a role in the central function. Therefore, the compounds (agonists or antagonists) that alter the binding property between the G protein-coupled receptor protein of the invention can be used as prophylactic and/or therapeutic agents for diseases associated with dysfunction of the receptor protein of the invention.

When the compounds are used as the prophylactic and/or therapeutic agents for diseases associated with dysfunction of the receptor protein of the invention, the pharmaceutical preparations can be obtained in a conventional manner.

For example, the compounds can be administered orally as sugar coated tablet, capsule, elixir, and microcapsule, or non-orally as injection such as aseptic solution or suspension in water or other pharmaceutically acceptable liquid. For example, preparations of the compounds can be manufactured by mixing with physiologically acceptable known carrier, flavor, filler, vehicle, antiseptic, stabilizer, and binder in a unit-dosage form required for generally approved drug preparation. The amount of the active ingredient is set to an appropriate volume within the specified range.

For the additive miscible with tablets, capsules, etc., for example, binders such as gelatin, cornstarch, tragacanth, and acacia, fillers such as crystalline cellulose, imbibers such as cornstarch, gelatin, and alginic acid, lubricants such as magnesium stearate, sweeteners such as sucrose and saccharin, and flavors such as peppermint, akamono oil and cherry are used. When the dosage form is a capsule, liquid carrier such as fat and oil may be contained. Aseptic compositions for injection can be formulated following the usual preparation such as dissolving or suspending the active substance in vehicle, e.g, water for injection, and natural plant oils e.g, sesame oil and coconut oil. For the aqueous solution for injection, for example, physiological saline and isotonic solutions (e.g, D-sorbitol, D-mannitol, sodium hydrochloride) containing glucose and other adjuvant are used. Appropriate dissolution-assisting agents, for example, alcohol (e.g., ethanol), polyalcohol (e.g., propylene glycol, polyethylene glycol), non-ionic surfactants (e.g., polysorbate 80™, HCO-50) may be combined. For the oily solution, for example, sesame oil and soybean oil are used, and dissolution-assisting agents such as benzyl benzoate and benzyl alcohol may be combined.

The prophylactic and/or therapeutic agents described above may be combined, for example, with buffers (e.g, phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol), and antioxidants. The preparation for injection is usually filled in appropriate ampoules.

The preparations obtained as described above are safe and low toxic, and can be administered to, for example, human and other mammals (e.g., rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g, for the patient with hypertension, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g, for the patient with hypertension, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(6) Quantification of the Receptor Protein of the Invention, its Partial Peptide, or its Salt Form The antibodies of the invention are capable of specifically recognizing the receptor protein etc. of the invention. Therefore, the antibodies can be used to quantify the receptor protein etc. of the invention in a test fluid, especially for quantification by the sandwich immunoassay. That is, the present invention provides, for example, the following quantification methods:

(i) A method of quantifying the receptor protein etc. of the invention in a test fluid, which comprises competitively reacting the antibody of the invention with the test fluid and a labeled form of the receptor protein etc. of the invention, and measuring the ratio of the labeled receptor protein etc. bound to the antibody; and, (ii) A method of quantifying the receptor protein etc. of the invention in a test fluid, which comprises reacting the test fluid with the antibody of the invention immobilized on a carrier and a labeled form of the antibody of the invention simultaneously or sequentially, and measuring the activity of the label on the immobilized carrier.

In (ii) described above, it is preferred that one antibody recognizes the N-terminal region of the receptor protein etc. of the invention, and another antibody reacts with the C-terminal region of the receptor protein etc. of the invention.

Using monoclonal antibodies to the receptor protein etc. of the invention (hereinafter sometimes referred to as the monoclonal antibodies of the invention), the receptor protein etc. of the invention can be assayed and also detected by tissue staining or the like. For this purpose, an antibody molecule itself may be used, or $F(ab')_2$, Fab' or Fab fractions of the antibody molecule may also be used. Assay methods using antibodies to the receptor protein etc. of the invention are not particularly limited. Any assay method can be used, so long as the amount of antibody, antigen, or antibody-antigen complex corresponding to the amount of antigen (e.g, the amount of the receptor protein) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the methods using labeled substances, there are employed, for example, radioisotopes, enzymes, fluorescent substances, luminescent substances, etc. For the radioisotope, for example, $[^{125}I]$, $[^{131}I]$, $[^{3}H]$ and $[^{14}C]$ are used. As the enzyme described above, stable enzymes with high specific activity are preferred; for example, β-galactosidase, β-glucosidase, alkaline phosphatase, peroxidase, malate dehydrogenase and the like are used. Example of the fluorescent substance used is fluorescamine and fluorescein isothiocyanate are used. For the luminescent substances, e.g, luminol, luminol derivatives, luciferin, and lucigenin. Furthermore, the biotin-avidin system may be used for binding antibody or antigen to the label.

For immobilization of antigen or antibody, physical adsorption may be used. Chemical binding methods conventionally used for insolubilization or immobilization of proteins or enzymes may also be used. For the carrier, for example, insoluble polysaccharides such as agarose, dextran, cellulose, etc.; synthetic resin such as polystyrene, polyacrylamide, silicon, and glass or the like is used.

In the sandwich method, the immobilized monoclonal antibody of the invention is reacted with a test fluid (primary reaction), then with the labeled monoclonal antibody of the invention (secondary reaction), and the activity of the label on the immobilizing carrier is measured, whereby the amount of the receptor protein of the invention in the test fluid can be quantified. The order of the primary and secondary reactions may be reversed, and the reactions may be performed simultaneously or with an interval. The methods of labeling and immobilization can be performed by the methods described above.

In the immunoassay by the sandwich method, the antibody used for immobilized or labeled antibodies is not necessarily one species, but a mixture of two or more species of antibody may be used to increase the measurement sensitivity.

In the methods of assaying the receptor protein etc. of the invention by the sandwich method, antibodies that bind to different sites of the receptor protein etc. are preferably used as the monoclonal antibodies of the invention for the primary and secondary reactions. That is, in the antibodies used for the primary and secondary reactions are, for example, when the antibody used in the secondary reaction recognizes the C-terminal region of the receptor protein, it is preferable to use the antibody recognizing the region other than the C-terminal region for the primary reaction, e.g., the antibody recognizing the N-terminal region.

The monoclonal antibodies of the invention can be used for the assay systems other than the sandwich method, for example, competitive method, immunometric method, nephrometry, etc. In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the measurement methods of the present invention, any particular conditions or procedures are not required. Systems for measuring the receptor protein of the present invention or its salts are constructed by adding the usual technical consideration in the art to the conventional conditions and procedures. For the details of these general technical means, reference can be made to the following reviews and texts. [For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immonoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies))(all published by Academic Press Publishing).

As described above, the receptor protein of the invention or its salts can be quantified with high sensitivity, using the antibodies of the invention.

By quantifying the receptor protein of the invention or its salts in vivo using the antibodies of the invention, diagnosis can be made on various diseases associated with dysfunction of the receptor protein of the invention.

The antibodies of the invention can also be used for specifically detecting the receptor protein etc. of the invention present in test samples such as body fluids or tissues. The antibodies may also be used for preparation of antibody columns for purification of the receptor protein etc. of the invention, for detection of the receptor protein etc. of the invention in each fraction upon purification, and for analysis of the behavior of the receptor protein of the invention in the test cells.

(7) Prophylactic and/or Therapeutic Agents for Various Diseases Comprising Compounds that Alter the Amount of the Receptor Protein of the Invention or its Partial Peptides in Cell Membrane As described above, the receptor protein of the invention is considered to play some important role in vivo, such as a role in the central function. Therefore, the compounds that alter the amount of the receptor protein of the invention or its partial peptide in cell membrane are useful as prophylactic and/or therapeutic agents for diseases associated with dysfunction of the receptor protein of the invention, such as central diseases (e.g, Alzheimer's disease, dementia, eating disorder), inflammatory diseases (e.g, allergy, rheumatism, osteoarthritis, erythematosus), circulatory diseases (e.g, hypertension, cardiac hypertrophy, cardiac angina, arteriosclerosis), cancer (e.g, non-small-cell lung cancer, ovarian cancer, prostate cancer, stomach cancer, bladder carcinoma, breast cancer, cancer of uterine cervix, colon cancer, rectum cancer), respiratory diseases (e.g, pneumonia, bronchitis, asthma, pulmonary fibrosis), diabetes, immune system diseases (e.g, Crohn's disease, atopic dermatitis, autoimmune disease, immunodeficiency, leukemia), diseases of liver and cholecyst (e.g, liver cirrhosis, hepatitis, liver failure, cholestasis, calculosis), alimentary diseases (e.g, ulcer, enterisis, malabsorption), infectious diseases, adiposis, hyperimmuno reaction after transplantation.

Among these diseases, against diseases caused by enhancement of immune function, function of macrophage or the like (e.g, inflammatory diseases, hyperimmuno reaction after transplantation), the compound that potentiates a physiological activity through the receptor protein of the invention (e.g, agonist) is particularly effective.

On the other hand, against diseases caused by suppression of immune function, function of macrophage or the like (e.g, immunodeficiency, infectious disease), the compound that reduces a physiological activity through the receptor protein of the invention (e.g, antagonist) is particularly effective.

When the compounds are used as the prophylactic and/or therapeutic agents for diseases associated with dysfunction of the receptor protein of the invention, the compound can be prepared into a drug product in a conventional manner.

For example, the compounds can be administered orally as a sugar coated tablet, capsule, elixir, and microcapsule, or non-orally as injection such as aseptic solution or suspension in water or other pharmaceutically acceptable liquid. For example, preparations of the compounds can be manufactured by mixing with physiologically acceptable known carrier, flavor, filler, vehicle, antiseptic, stabilizer, and binder in a unit-dosage form required for generally approved drug preparation. The amount of the active ingredient is set to an appropriate volume within the specified range.

For the additive miscible with tablets and capsules, for example, binders such as gelatin, cornstarch, tragacanth, and acacia, fillers such as crystalline cellulose, imbibers such as cornstarch, gelatin, and alginic acid, lubricants such as magnesium stearate, sweeteners such as sucrose and saccharin, and flavors such as peppermint, akamono oil and cherry are used. When the dosage form is a capsule, liquid carrier such as fat and oil may be contained. Aseptic compositions for injection can be formulated following the usual preparation procedure such as dissolving or suspending the active substance in vehicle, e.g., water for injection, and natural plant oils e.g., sesame oil and coconut oil. For the aqueous solution for injection, for example, physiological saline and isotonic solutions (e.g., D-sorbitol, D-mannitol, sodium hydrochloride) containing glucose and other adjuvant are used. Appropriate dissolution-assisting agents, for example, alcohol (e.g., ethanol), polyalcohol (e.g., propylene glycol, polyethylene glycol), nonionic surfactant (e.g, polysorbate 80™, HCO-50) may be combined. For the oily solution, for example, sesame oil and soybean oil are used, and dissolution-assisting agents such as benzyl benzoate and benzyl alcohol may be combined.

The prophylactic and/or therapeutic agents described above may be combined with buffers (e.g, phosphate buffer, sodium acetate buffer), soothing agents (e.g, benzalkonium chloride, procaine hydrochloride), stabilizers (e.g, human serum albumin, polyethylene glycol), preservatives (e.g, benzyl alcohol, phenol), antioxidants, and the like. The preparation for injection is usually filled in appropriate ampoules.

The preparations obtained as described above are safe and low toxic, and can be administered to, for example, human and other mammals (e.g, rats, mice, rabbits, sheep, swine, bovine, cats, dogs, monkeys, etc.).

The dose of the compounds or their salt forms varies depending on subject to be administered, target organs, conditions, routes for administration, etc.; in oral administration, e.g. for the patient with hypertension, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g, for the patient with hypertension, to administer the active ingredient intravenously in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(8) Neutralization by Antibodies to the Receptor Protein, its Partial Peptides, or their Salts of the Invention The neutralizing activity of antibodies to the receptor protein of the present invention, its partial peptides, or its salts refers to an activity of inactivating the signal transduction function involving the receptor protein.

Therefore, when the antibody has the neutralizing activity, the antibody can inactivate the signal transduction in which the receptor protein participates, for example, inactivate the receptor protein-mediated cell-stimulating activity (e.g., activity that promotes or inhibits arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc.). Therefore, the antibody can be used for the prevention and/or treatment of diseases caused by overexpression of the receptor protein.

(9) Preparation of Animals Carrying the DNA Encoding the G Protein-Coupled Receptor Protein of the Invention Using the DNA of the invention, transgenic animals expressing the receptor protein etc. of the invention can be prepared. Examples of the animals include non-human mammals (e.g, rats, mice, rabbits, sheep, swine, bovine, cats, dogs, monkeys, etc.) (hereinafter, merely referred to as animals) can be used, with mice and rabbits being particularly appropriate.

To introduce the DNA of the invention to target animals, it is generally advantageous to use the DNA in a gene construct ligated downstream of a promoter that can express the DNA in animal cells. For example, when the DNA of the invention derived from rabbit is transferred, e.g., the gene construct, in which the DNA is ligated downstream of a promoter that can expresses the DNA of the invention derived from animals containing the DNA of the invention highly homologous to the rabbit-derived DNA, is microinjected to rabbit fertilized ova; thus, the DNA-introduced animal, which is capable of producing a high level of the receptor protein etc. of the invention, can be produced. Examples of the promoters that are usable include virus-derived promoters and ubiquitous expression promoters such as metallothionein promoter, but promoters of NGF gene and enolase that are specifically expressed in the brain are preferably used.

The introduction of the DNA of the invention at the fertilized egg cell stage secures the presence of the DNA in all germ and somatic cells in the produced animal. The presence of the receptor protein etc. of the invention in the germ cells in the DNA-introduced animal means that all germ and somatic cells contain the receptor protein etc. of the invention in all progenies of the animal. The progenies of the animal that took over the gene contain the receptor protein etc. of the invention in all germ and somatic cells.

The DNA-introduced animals of the invention can be maintained and bled in the conventional environment as animals carrying the DNA after confirming the stable retention of the gene in the animals through mating. Furthermore, mating male and female animals containing the objective DNA results in acquiring homozygous animals having the introduced gene on both homologous chromosomes. By mating the male and female homozygotes, bleeding can be performed so that all progenies contain the DNA.

Since the receptor protein etc. of the invention is highly expressed in the animals in which the DNA of the invention has been introduced, the animals are useful for screening of agonists or antagonists to the receptor protein etc. of the invention.

The animals in which the DNA of the invention has been introduced can also be used as cell sources for tissue culture. The receptor protein of the invention can be analyzed by, for example, directly analyzing the DNA or RNA in tissues from the mouse in which the DNA of the invention has been introduced, or by analyzing tissues containing the receptor protein etc. expressed from the gene. Cells from tissues containing the receptor protein etc. of the invention are cultured by the standard tissue culture technique. Using these cells, for example, the function of tissue cells such as cells derived from the brain or peripheral tissues, which are generally difficult to culture, can be studied. Using these cells, for example, it is possible to select pharmaceuticals that increase various tissue functions. When a highly expressing cell line is available, the receptor protein etc. of the invention can be isolated and purified from the cell line.

(10) Knockout Animal

The present invention provides a non-human mammal embryonic stem cell bearing the DNA of the invention inactivated and a non-human mammal deficient in expressing the DNA of the invention.

Thus, the present invention provides:

(1) A non-human mammal embryonic stem cell in which the DNA of the invention is inactivated;

(2) The embryonic stem cell according to (1), wherein the DNA is inactivated by introducing a reporter gene (e.g, β-galactosidase gene derived from *Escherichia coli*);

(3) The embryonic stem cell according to (1), which is resistant to neomycin;

(4) The embryonic stem cell according to (1), wherein the non-human mammal is a rodent;

(5) An embryonic stem cell according to (4), wherein the rodent is mouse;

(6) A non-human mammal deficient in expressing the DNA of the invention, wherein the DNA of the invention is inactivated;

(7) The non-human mammal according to (6), wherein the DNA is inactivated by inserting a reporter gene (e.g, β-galactosidase derived from *Escherichia coli*) therein and the reporter gene is capable of being expressed under control of a promoter for the DNA of the invention;

(8) The non-human mammal according to (6), which is a rodent;

(9) The non-human mammal according to (8), wherein the rodent is mouse; and,

(10) A method for screening a compound or its salt that promotes or inhibits the promoter activity for the DNA of the invention, which comprises administering a test compound to the mammal of (7) and detecting expression of the reporter gene.

The non-human mammalian embryonic stem cell, in which the DNA of the invention is inactivated, refers to a non-human mammalian embryonic stem cell that suppresses the ability of the non-human mammalian to express the DNA by artificially mutating the DNA of the invention possessed in the non-human mammal, or the DNA has no substantial ability to express the polypeptide of the invention (hereinafter sometimes referred to as the knockout DNA of the invention) by substantially inactivating the activities of the polypeptide of the invention encoded by the DNA (hereinafter merely referred to as ES cell).

As the non-human mammals, the same examples as described above apply.

Techniques for artificially mutating the DNA of the invention include deletion of a part or all of the DNA sequence and insertion of or substitution with other DNA, e.g., by genetic engineering. By these variations, the knockout DNA of the invention may be prepared, for example, by shifting the reading frame of a codon or by disrupting the function of a promoter or exon.

Specifically, the non-human mammalian embryonic stem cell, in which the DNA of the invention is inactivated (hereinafter merely referred to as the ES cell with the DNA of the invention inactivated or the knockout ES cell of the present invention), can be obtained by, for example, isolating the DNA of the invention possessed by the target non-human mammal, inserting a DNA strand (hereinafter simply referred to as targeting vector) having a DNA sequence constructed so as to eventually destroy the gene by inserting into its exon site a chemical resistant gene such as a neomycin resistant gene or a hygromycin resistant gene, or a reporter gene such as lacZ (β-galactosidase gene) or cat (chloramphenicol acetyltransferase gene), etc. thereby to destroy the functions of exon, or by inserting into the intron site between exons a DNA sequence which terminates gene transcription (e.g, polyA-added signal, etc.) thereby to disable the synthesis of complete messenger RNA, into a chromosome of the animal cells by, e.g, homologous recombination. The thus-obtained ES cells are analyzed by the Southern hybridization using as a probe a DNA sequence on or near the DNA of the invention, or by PCR using as primers a DNA sequence on the targeting vector and another DNA sequence near the DNA of the invention which is not included in the targeting vector, and the knockout ES cell of the invention is selected.

The parent ES cells to inactivate the DNA of the invention by homologous recombination, etc. may be of a strain already established as described above, or may be originally established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum collection per C57BL/6 mouse or C57BL/6 has been improved by crossing with DBA/2, may be preferably used, instead of obtaining a pure line of ES cells with the clear immunological genetic background. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes of 3.5 days after fertilization are commonly used. A large number of early stage embryos may be acquired more efficiently, by collecting the embryos of the 8-cell stage and using the same after culturing until the blastocyte stage.

Although the ES cells used may be of either sex, male ES cells are generally more convenient for generation of a germ cell line chimera and are therefore preferred. It is desirable to identify sexes as soon as possible also in order to save painstaking culture time.

As an example of the method for sex identification of the ES cell, mention may be made of a method in which a gene in the sex-determining region on the Y-chromosome is amplified by PCR and detected. When this method is used, ES cells (about 50 cells) corresponding to almost 1 colony are sufficient, whereas karyotype analysis hitherto required about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1–10000 U/ml) on appropriate feeder cells such as STO fibroblasts, treated with a trypsin/EDTA solution (normally about 0.001 to about 0.5% trypsin/about 0.1 to 5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in monolayers or to form cell aggregates in suspension under appropriate conditions, it is possible to differentiate them to various cell types, for example, parietal and visceral muscles, cardiac muscle or the like [M. J. Evans and M. H. Kaufman, Nature, 292,154, 1981; G. R. Martin, Proc. Natl. Acad. Sci. U.S.A., 78, 7634,1981; T. C. Doetschman et al., Journal of Embryology Experimental Morphology, 87, 27,1985]. The cells deficient in expression of the DNA of the invention, which are obtainable from the differentiated ES cells of the invention, are useful for studying the functions of the polypeptide of the invention in vitro cytologically or molecular biologically.

The non-human mammal deficient in expression of the DNA of the invention can be identified from a normal animal by measuring the amount of mRNA in the subject animal by a publicly known method, and indirectly comparing the levels of expression.

As the non-human mammal, the same examples described above, apply.

With respect to the non-human mammal deficient in expression of the DNA of the invention, the DNA of the invention can be made knockout by transfecting a targeting vector, prepared as described above, to mouse embryonic stem cells or mouse oocytes thereof, and conducting homologous recombination in which a targeting vector DNA sequence, wherein the DNA of the invention is inactivated by the transfection, is replaced with the DNA of the invention on a chromosome of a mouse embryonic stem cell or mouse oocyte.

The cells, in which the DNA of the invention is rendered knockout, can be identified by the Southern hybridization analysis using as a probe a DNA sequence on or near the DNA of the invention, or by PCR analysis using as primers a DNA sequence on the targeting vector and another DNA sequence which is not included in the DNA of the invention derived from mouse, which is used as the targeting vector. When non-human mammalian embryonic stem cells are used, the cell line wherein the DNA of the invention is inactivated is cloned by homologous recombination; the resulting cloned cell line is injected to, e.g, a non-human mammalian embryo or blastocyte, at an appropriate stage such as the 8-cell stage. The resulting chimeric embryos are transplanted to the uterus of the pseudo-pregnant non-human mammal. The resulting animal is a chimeric animal composed of both cells having the normal locus of the DNA of the invention and those having an artificially mutated locus of the DNA of the invention.

When some germ cells of the chimeric animal have a mutated locus of the DNA of the invention, an individual, in which all tissues are composed of cells having an artificially mutated locus of the DNA of the invention, can be selected from a series of offspring obtained by crossing between such a chimeric animal and a normal animal, e.g., by coat color identification, etc. The individuals thus obtained are normally deficient in heterozygous expression of the polypeptide of the invention. The individuals deficient in homozygous expression of the polypeptide of the invention can be obtained from offspring of the intercross between the heterozygotes.

When an oocyte is used, a DNA solution may be injected, e.g., to the prenucleus by microinjection thereby to obtain a transgenic non-human mammal having a targeting vector introduced into its chromosome. From such transgenic non-human mammals, those having a mutation at the locus of the DNA of the invention can be obtained by selection based on homologous recombination.

As described above, individuals wherein the DNA of the invention is rendered knockout permit passage rearing under ordinary rearing conditions, after it is confirmed that in the animal individuals obtained by their crossing, the DNA has been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the invention is inactivated, is very useful for preparing a non-human mammal deficient in expression of the DNA of the invention.

Since the non-human mammal, in which the DNA of the invention fails to express, lacks various biological activities induced by the polypeptide of the invention, such an animal can be a disease model suspected of inactivated biological activities of the polypeptide of the invention and thus, offers an effective study to investigate causes for and therapy for these diseases.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
lie: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid The substituents, protective groups and reagents, which are frequently used throughout the specification, are shown by the following abbreviations.
Me: methyl
Et: ethyl
Bu: butyl
Ph: phenyl
TC: thiazolidine-4(R)-carboxamide
Tos: p-toluenesulfonyl
CHO: formyl
Bzl: benzyl
$Cl_2Bzl$: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenztriazole

[SEQ ID NO: 11]
This shows the base sequence of primer 3, which is used for PCR reaction in Example 5 below.

[SEQ ID NO: 12]
This shows the base sequence of primer 4, which is used for PCR reaction in Example 5 below.

[SEQ ID NO: 13]
This shows the DNA sequence of bovine TGR5.

[SEQ ID NO: 14]
This shows the amino acid sequence of bovine TGR5.

[SEQ ID NO: 15]
This shows the DNA sequence of rabbit TGR5.

[SEQ ID NO: 16]
This shows the amino acid sequence of rabbit TGR5.

[SEQ ID NO: 17]
This shows the base sequence of of primer, which is used for PCR reaction in Example 6 below.

[SEQ ID NO: 18]
This shows the base sequence of bR primer, which is used for PCR reaction in Example 6 below.

[SEQ ID NO: 19]
This shows the base sequence of rabbit F primer, which is used for PCR reaction in Example 7 below.

[SEQ ID NO: 20]
This shows the base sequence of rabbit R primer, which is used for PCR reaction in Example 7 below.

[SEQ ID NO: 21]
This shows the base sequence of primer, which is used for the quantification of the expression level of IL-1α mRNA in Example 11 below.

[SEQ ID NO: 22]
This shows the base sequence of primer, which is used for the quantification of the expression level of IL-1α mRNA in Example 11 below.

[SEQ ID NO: 23]
This shows the base sequence of probe, which is used for the quantification of the expression level of IL-1α mRNA in Example 11 below.

[SEQ ID NO: 24]
This shows the base sequence of primer, which is used for the quantification of the expression level of IL-1β mRNA in Example 11 below.

[SEQ ID NO: 25]
This shows the base sequence of primer, which is used for the quantification of the expression level of IL-1β mRNA in Example 11 below.

[SEQ ID NO: 26]
This shows the base sequence of probe, which is used for the quantification of the expression level of IL-1β mRNA in Example 11 below.

[SEQ ID NO: 27]
This shows the base sequence of primer, which is used for the quantification of the expression level of IL-6 mRNA in Example 11 below.

[SEQ ID NO: 28]
This shows the base sequence of primer, which is used for the quantification of the expression level of IL-6 mRNA in Example 11 below.

[SEQ ID NO: 29]
This shows the base sequence of probe, which is used for the quantification of the expression level of IL-6 mRNA in Example 11 below.

[SEQ ID NO: 30]
This shows the base sequence of primer, which is used for the quantification of the expression level of IL-8 mRNA in Example 11 below.

[SEQ ID NO: 31]
This shows the base sequence of primer, which is used for the quantification of the expression level of IL-8 mRNA in Example 11 below.

[SEQ ID NO: 32]
This shows the base sequence of probe, which is used for the quantification of the expression level of IL-8 mRNA in Example 11 below.

[SEQ ID NO: 33]
This shows the base sequence of primer, which is used for the quantification of the expression level of TNFα mRNA in Example 11 below.

[SEQ ID NO: 34]
This shows the base sequence of primer, which is used for the quantification of the expression level of TNFα mRNA in Example 11 below.

[SEQ ID NO: 35]
This shows the base sequence of probe, which is used for the quantification of the expression level of TNFα mRNA in Example 11 below.

[SEQ ID NO: 36]
This shows the amino acid sequence of the human GPR7 ligand precursor H.

[SEQ ID NO: 37]
This shows the base sequence of DNA encoding the human GPR7 ligand precursor H.

[SEQ ID NO: 38]
This shows the amino acid sequence of GPR7.

[SEQ ID NO: 39]
This shows the base sequence of DNA encoding GPR7.

[SEQ ID NO: 40]
This shows the synthetic DNA, which is used for the screening of cDNA encoding the human GPR7 ligand precursor H in Reference Example 4.

[SEQ ID NO: 41]
This shows the synthetic DNA, which is used for the screening of cDNA encoding the human GPR7 ligand precursor H in Reference Example 4.

[SEQ ID NO: 42]
This shows the base sequence of primer, which is used in Reference Example 2.

[SEQ ID NO: 43]
This shows the base sequence of primer, which is used in Reference Example 2.

The transformant *Escherichia coli* JM109/pCR4-hTGR5 obtained in Reference Example 1 described below was on deposit with International Patent Organisms Depository, National Institute of Advanced Industrial Science and Technology (formerly, National Institute of Bioscience and Human-Technology (NIBH), Ministry of International Trade and Industry), located at Central 6, 1-1-1 Higashi, Tsukuba, Ibaraki, 305-8566, Japan, as the Accession Number FERM BP-7114 on Apr. 3, 2000 and with Institute for Fermentation (IFO), located at 2-17-85 Juso-honmachi, Yodogawa-ku, Osaka-shi, Osaka, Japan, as the Accession Number IFO 16410 on Mar. 23, 2000.

The transformant *Escherichia coli* DH5α/pAKKO1.11 H-rTGR5 obtained in Example 5 described below was on deposit with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7114 on Feb. 7, 2002 and with Institute for Fermentation (IFO), located at 2-17-85 Juso-honmachi, Yodogawa-ku, Osaka-shi, Osaka, Japan, as the Accession Number IFO 16745 on Jan. 10, 2002.

The transformant *Escherichia coli* DH5α/pCR2.1-mTGR5 obtained in Example 5 described below was on deposit with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7878 on Feb. 7, 2002 and with Institute for Fermentation (IFO), located at 2-17-85 Juso-honmachi, Yodogawa-ku, Osaka-shi, Osaka, Japan, as the Accession Number IFO 16746 on Jan. 10, 2002.

The transformant *Escherichia coli* JM109/pTAbTGR5-1 obtained in Example 6 described below was on deposit with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7879 on Feb. 7, 2002 and with Institute for Fermentation (IFO), located at 2-17-85 Juso-honmachi, Yodogawa-ku, Osaka-shi, Osaka, Japan, as the Accession Number IFO 16747 on Jan. 10, 2002.

The transformant *Escherichia coli* JM109/pTArabbit-TGR5-1 obtained in Example 7 described below was on deposit with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7880 on Feb. 7, 2002 and with Institute for Fermentation (IFO), located at 2-17-85 Juso-honmachi, Yodogawa-ku, Osaka-shi, Osaka, Japan, as the Accession Number IFO 16748 on Jan. 10, 2002.

The transformant *Escherichia coli* JM109/pTAhGPR7-1 obtained in Reference Example 4 described below was on deposit with International Patent Organisms Depository, National Institute of Advanced Industrial Science and Technology, located at Central 6, 1-1-1 Higashi, Tsukuba, Ibaraki, 305-8566, Japan, as the Accession Number FERM BP-7640 on Jun. 27, 2001, as *Escherichia coli* JM109/pTAhGPR7L-1, and with Institute for Fermentation (IFO), located at 2-17-85 Juso-honmachi, Yodogawa-ku, Osaka-shi, Osaka, Japan, as the Accession Number IFO 16644 on Jun. 19, 2001.

EXAMPLES

The present invention is described in detail below with reference to EXAMPLES, but is not deemed to limit the scope of the present invention thereto. The gene manipulation procedures using *Escherichia coli* were performed according to the methods described in the Molecular Cloning.

Reference Example 1

Cloning of the cDNA encoding the human pancreas-derived G protein-coupled receptor protein and determination of the base sequence Using human pancreas cDNA (CLONTECH) as a template and two primers, namely, primer 1 (SEQ ID NO: 3) and primer 2 (SEQ ID NO: 4), PCR was carried out. The reaction solution in the above reaction comprised of 1/10 volume of the above cDNA as a template, 1/50 volume of Advantage-GC2 Polymerase Mix (Clontech), 0.5 μM each of primer 1 (SEQ ID NO: 3) and primer 2 (SEQ ID NO: 4), 200 μM of dNTPs, and 1/5 volume of buffer attached to the enzyme, and 1/5 volume of GC Melt to make the total volume 20 μl. The PCR reaction was carried out by reaction of 94° C. for 5 minute, then a cycle set to include 94° C. for 30 seconds followed by 60° C. for 30 seconds and 68° C. for 2 minutes, which was repeated 30 times, and finally, extension reaction at 68° C. for 5 minutes. The PCR product was subcloned into plasmid vector pCR4 (Invitrogen) following the instructions attached to the TA Cloning Kit (Invitrogen). The plasmid was then introduced into *Escherichia coli* JM109, and the clones containing the cDNA were selected on LB agar plates containing ampicillin. As a result of analysis for sequence of each clone, the base sequences of cDNA encoding the novel G protein-coupled receptor protein were obtained (SEQ ID NO: 2). A novel G protein-coupled receptor protein having the amino acid sequence deduced from the cDNA sequence (SEQ ID NO: 1) was designated TGR5. In addition, the transformant containing the DNA shown by SEQ ID NO: 2, was designated *Escherichia coli* JM109/pCR4-hTGR5.

Example 1

Detection of the Activity Mediated by a Substance Relating to Cholesterol Metabolism in HK293 Cells, in which TGR5 is Transiently expressed Detection of a TGR5-specific stimulus activity mediated by substancesrelating to cholesterol metabolism was performed using an expression level of reporter gene product (luciferase), which has been produced by expression induction of CRE promoter as an index.

HEK293 cells were suspended in growth medium (DMEM (Dulbecco's Modified Eagle Medium) (Gibco-BRL) supplemented with 10% fetal bovine serum (Gibco-BRL)), and seeded on Blackwell 96-well plate (Becton Dickinson) coated with collagen at the concentration of $1\times^5$ cells/well. After overnight culture under conditions of 37° C. and 5% $CO_2$, using the expression vector plasmid, which was prepared by inserting TGR5 gene into the expression vector for animal cells, pAKKO-111H (the same plasmid as pAKKO-1.111H described in Biochem. Biophys. Acta, Vol.1219, 251-259 (1994) by Hinuma, S. et al.), or pAKKO-111H containing no TGR5 gene, concurrently with pCRE-Luc (Clontech), which is a plasmid containing a reporter gene, cells were transfected as described below.

Lipofectamine diluted solution was prepared by mixing OPTI-MEM-I (GibcoBRL) and Lipofectamine™ 2000 Reagent (GibcoBRL) at the ratio of 24:1. In addition, DNA diluted solution was prepared by mixing OPTI-MEM-I, TGR5 expressing vector plasmid or an original vector plasmid (240 ng/μl) and pCRE-Luc (240 ng/μl) at the ratio of 24:0.9:0.1. The Lipofectamine diluted solution was mixed with the same volume of the DNA diluted solution to form a complex of DNA and Lipofectamine by standing for 20 minutes at room temperature. Then, 25 μl of the above solution was added to the plate, in which the HEK293 cells had been cultured. The cells were cultured for overnight under conditions of 37° C. and 5% $CO_2$.

The transfected HEK293 cells were washed with medium for assay (DMEM supplemented with 0.1% bovine serum albumin), and lithocholic acid (Wako Pure Chemicals Industries, Ltd.) and progesterone (Wako Pure Chemicals Industries, Ltd.), which were diluted with medium for assay, were added to the cells to make $2 \times 10^{-5}$ M. Thereafter, the cells were cultured for 4 hours under conditions of 37° C. and 5% $CO_2$. The culture supernatant was discarded, and 50 μl of PicaGene LT2.0 (Toyo Ink Manufacturing Co., Ltd.), the substrate for luciferase activity assay, were added to the cells. Then the luminescence of luciferase was measured using plate reader (ARVO sx multilabel counter, Wallac).

As a result, in the HEK293 cells, in which TGR5 gene having the base sequence represented by SEQ ID NO: 2 was introduced, enhancement of the luciferase activity by lithocholic acid and progesterone was specifically observed (FIG. 6).

Example 2

Introduction of G Protein-Coupled Receptor Protein Expressing Plasmid and Reporter Plasmid into Host Cells Using an expression plasmid for animal cells wherein cDNA encoding a variety of G protein-coupled receptor proteins such as thyroid hormone stimulating factor receptor (TRHR), neuromedine U receptor (FM-3 and TGR-1), prolactin releasing factor receptor (hGR3), apelin receptor (APJ) and the like was inserted, which was prepared by a publicly known method, *Escherichia coli* JM109 was transformed. After the resultant colony was isolated and cultured, a plasmid was prepared using QIAGEN Plasmid Maxi Kit (QIAGEN). Further, pCRE-Luc (Clontech), a reporter plasmid, in which luciferase gene was ligated downstream cAMP response element (CRE) as a reporter, was prepared in the same way.

As host cells wherein an expression plasmid for G protein-coupled receptor protein and a reporter plasmid were introduced, HEK293 cells in 100 μl of culture fluid were seeded in collagen type I-coated 96-well black plate (Beckton Dickinson) at the concentration of 100,000 cells/well, and was cultured for overnight. In a similar way, CHO-mock cells wherein CHO (dhfr⁻) cells were transformed with pAKKO-111H, in 100 μl of culture fluid were seeded in 96-well black plate by Coaster at 40,000 cells/well, and cultured for overnight. In each cell, as a medium for plate culture, DMEM (GibcoBRL) only supplemented with 10% fetal bovine serum was used.

Each plasmid was diluted to the concentration of 240 ng/μl. Plasmids were added to 240 μl of Opti-MEM-I (GibcoBRL) at the ratio of 9 μl of the expression plasmid for G protein-coupled receptor protein to 1 μl of reporter plasmid. By mixing this solution with equal volume of the solution wherein 10 μl of Lipofectamine 2000 (GibcoBRL) was added to 240 μl of Opti-MEM-I, a complex of liposome with plasmids was formed in accordance with the method described in the attached manual. Further, in order to operate an effective screening, the solution with the same ratio of other reagents as described above except for addition of 5 μl each of three receptor-expressing plasmids at the concentration of 240 ng/μl was prepared. By adding 25 μl/well of these solutions to culture fluid of HEK293 or CHO-mock cells and culturing at 37° C., the plasmids were introduced. For CHO-mock cells, over 4 hours after plasmid addition, the culture fluid was replaced with an assay buffer (DMEM supplemented with 0.1% bovine serum albumin) to be serum-free.

Example 3

Detection of Ligand Activity by Reporter Assay

For HEK293 cells, by replacing the culture fluid with the assay buffer described in EXAMPLE 2 before 1 hour of assay, preincubation was performed. A solution, which a ligand or ligand candidate compound was dissolved in the assay buffer, was prepared and added to HEK293 cells or CHO-mock cells prepared in EXAMPLE 2. Alternatively, an assay under condition wherein forskolin was added to the assay buffer at the final concentration of 2 μM, was performed in the same way. By incubating for 4 hours after addition of sample, enhancement or inhibition of transcription/translation of the reporter gene, which is derived from intracellular signal transduction caused by an agonist activity of ligand mediated by receptor, was introduced. After completion of incubation, the assay buffer was removed from each well. Then 50 μl of luminescent substrate for PicaGene LT2.0 (Toyo Ink) was added to each well. After lysing the cells and completely mixing the lysate with the substrate, a luminescent level derived from induction level of reporter gene expression in each well was measured with the plate reader described in EXAMPLE 1.

According to the methods described in EXAMPLES 2 and 3, using the expression plasmid wherein cDNA encoding a variety of G protein-coupled receptor proteins were inserted, induction of reporter gene expression by stimulating a ligand was measured in HEK293 cells. For CRFR coupled with Gs, the G protein α subunit, which transduces a signal into cells through receptor, activation of the reporter gene by addition of ligand was detected under conditions both with and without forskolin. In addition, for APJ coupled with suppressive Gαi, activation of the reporter gene by addition of ligand was detected under conditions with forskolin.

Figure 7:
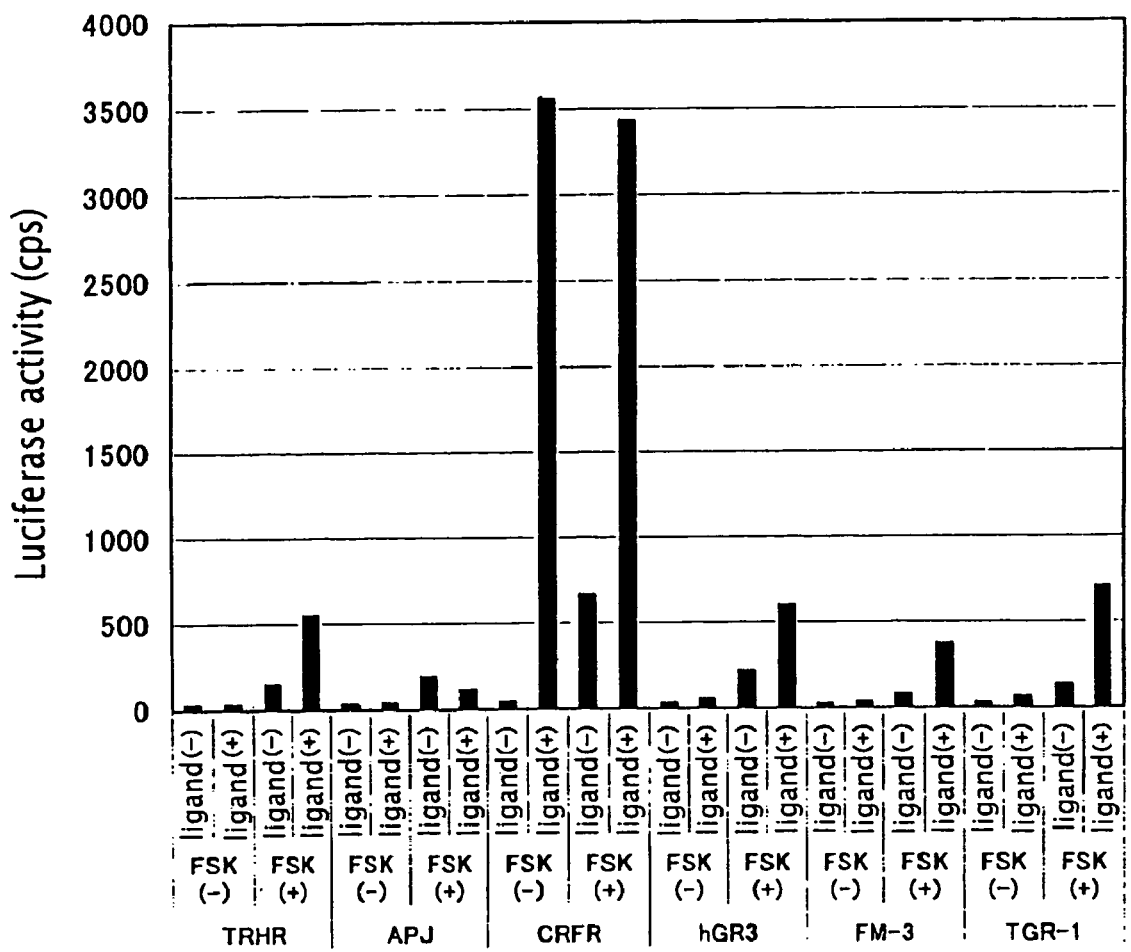
FIG. 7 shows the result of expression induction of the reporter gene by stimulation of ligand in HEK293 cells.

Further, for the receptors, TRHR, FM-3 and TGR-1 coupled with Gq, enhancement of the reporter gene expression was detected under condition with forskolin. For the receptor, hGR3 coupled with both Gq and Gi, enhancement of the reporter gene expression was also detected under condition with forskolin (FIG. 7).

Example 4

Reporter Assay Using Suppressive G Protein α Subunit Gi Expressing Plasmid

A suppressive G protein α subunit (Gi) plasmid was constructed and prepared with the similar method to that for the expression plasmid for G protein-coupled receptor protein shown in EXAMPLE 2 (here, for Gi, no object as to animal species). The Gi plasmid, the receptor expressing plasmid and the reporter plasmid were added to 240 μl of Opti-MEM-I at the ratio of 3 μl, 7μ and 1μ, respectively. Using the method with the same conditions as that of EXAMPLE 2 except for the above condition, DNA was introduced into HEK293 or CHO-mock cells. The mixing ratio of these three plasmids is, where the total volume is 11 μl, appropriate for 1 to 6, preferably 1 to 3 of Gi. According to the method of EXAMPLE 3, the assay was done, and ligand activity was detected.

Figure 8:
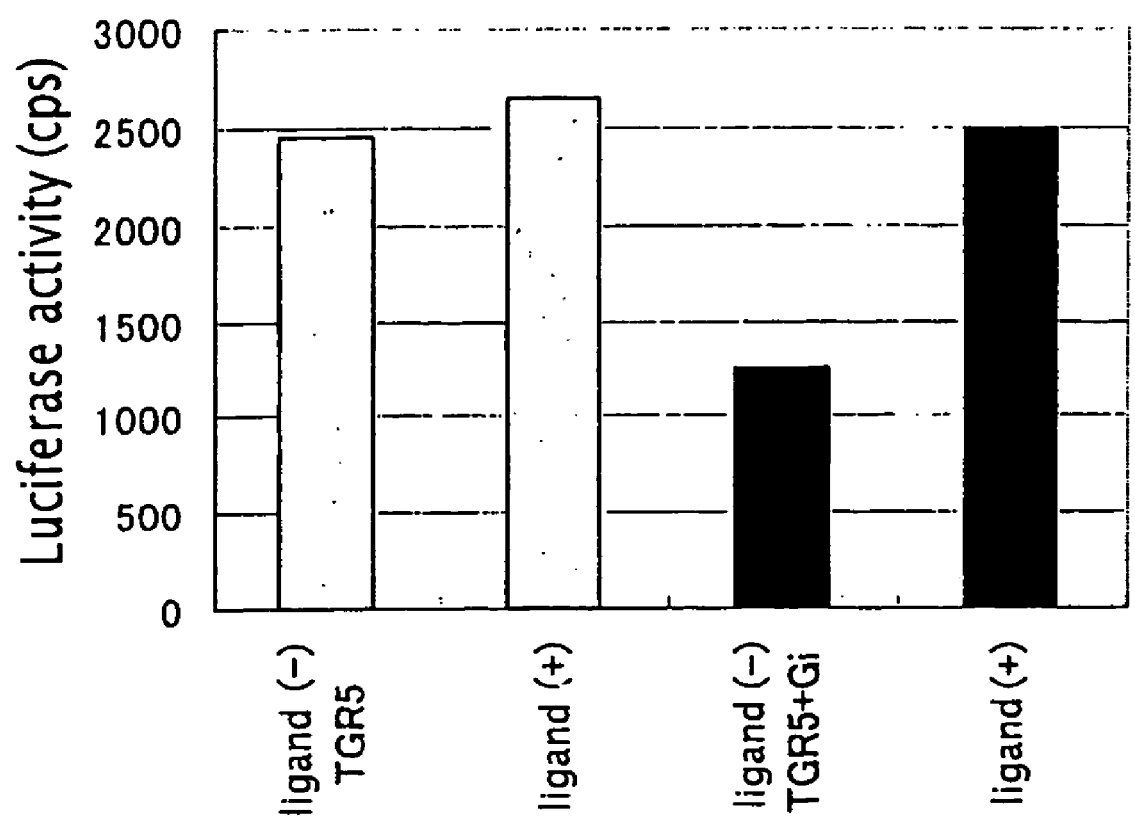
FIG. 8 shows the result of the reaction of TGR5 for lithocholic acid using Gi.

As a result of detection for the reaction of TGR5 against lithocholic acid using Gi, in the assay for the G. protein-coupled receptor TGR5 using CHO-mock cells, by co-expressing Gi with TGR5, luciferase activity without ligand (ligand (−)) can significantly be reduced. Thereby, detection for increasing an activity by ligand ($2 \times 10^{-5}$ M lithocholic acid, ligand (+)) became possible (FIG. 8).

Example 5

Cloning of the cDNA Encoding the Mouse and Rat TGR5 Protein and Determination of the Base Sequence Thirty μl of mixture consisting of 0.4 μM oligo DNA represented SEQ ID NO: 9 as sense primer 1, 0.4 μM oligo DNA represented SEQ ID NO: 10 as sense primer 2, 0.3 μl of GC2 DNA Polymerase (Clontech), 6 μl of 5×Buffer, 6 μl of GC-Melt, 0.2 mM dNTP (TaKaRa), 3 μl of heart cDNA solution of Marathon-Ready Mouse cDNA library (Clontech) and 9.9 μl of sterilized water, was prepared. Using thermal cycler (GeneAmp PCR system model 9700 (Applied Biosystems)), with programme of touchdown PCR comprising standing at 94° C. for 20 seconds, a cycle set to include 94° C. for 30 seconds, 64° C. for 30 seconds, and 68° C. for 2 minutes, wich is repeated 5 cycles, a cycle set to include 94° C. for 30 seconds, 62° C. for 30 seconds, and 68° C. for 2 minutes, wich is repeated 5 cycles, a cycle set to include 94° C. for 30 seconds, 60° C. for 30 seconds, and 68° C. for 2 minutes, wich is repeated 35 cycles, and finally an extension reaction at 68° C. for 7 minutes, PCR reaction was carried out. Next, a portion of reaction product was electrophoresed using 1.5% agarose gel containing ethydium bromide. Then a band corresponding to DNA amplified by PCR reaction at the position of approximately 1 kb compared with molecular weight marker was confirmed under UV irradiation. Subsequently, for determination of the base sequence, using pCR2.1-TOPO (Invitrogen), TA cloning was performed, and the obtained plasmid was introduced into *Escherichia coli* DH5a competent cells. Clones harboring plasmid, in which foreign DNA fragment was inserted, were selected from colonies of ampicillin resistant transformants appearing on ampicillin-containing LB agar medium by colony PCR. For determination of the base sequence of insert DNA, sequencing reaction using ABI PRISM BigDye Terminator Cycle Sequencing FS Ready Reaction Kit (Applied Biosystems) was carried out with thermal cycler (GeneAmp PCR system model 9700 (Applied Biosystems)) in accordance with the conditions in the information attached to the product. Then the sample was analyzed with DNA sequencer, ABI PRISM 3100 Genetic Analyzer (Applied Biosystems).

As a result, from PCR product, a sequence of structure gene having homology to novel 329 amino acids shown by SEQ ID NO: 5, i.e, TGR5, which consists of the base sequence of 990 bases represented by SEQ ID NO: 6, was determined. A novel G protein-coupled receptor protein containing the sequence shown by SEQ ID NO: 5 was designated mTGR5. Further, the transformant was designated *Escherichia coli* DH5a/pCR2.1-mTGR5.

Thirty μl of mixture consisting of 0.4 μM oligo DNA represented SEQ ID NO: 11 as sense primer 3, 0.4 μM oligo DNA represented SEQ ID NO: 12 as sense primer 4, 0.3 μl of Advantage 2 DNA Polymerase (Clontech), 3 μl of 10×Buffer, 0.2 mM dNTP (TaKaRa), 3 μl of heart cDNA solution of Marathon-Ready Rat cDNA library (Clontech) and 18.9 μl of sterilized water, was prepared. Using thermal cycler (GeneAmp PCR system model 9700 (Applied Biosystems)), with programme of touchdown PCR comprising standing at 94° C. for 20 seconds, a cycle set to include 94° C. for 30 seconds, 64° C. for 30 seconds, and 68° C. for 2 minutes, wich is repeated 5 cycles, a cycle set to include 94° C. for 30 seconds, 62° C. for 30 seconds, and 68° C. for 2 minutes, wich is repeated 5 cycles, a cycle set to include 94° C. for 30 seconds, 60° C. for 30 seconds, and 68° C. for 2 minutes, wich is repeated 35 cycles, and finally an extension reaction at 68° C. for 7 minutes, PCR reaction was carried out. Next, a portion of reaction product was electrophoresed using 1.5% agarose gel containing ethydium bromide. Then a band corresponding to DNA amplified by PCR reaction at the position of approximately 1 kb compared with molecular weight marker was confirmed under UV irradiation. Subsequently, for determination of the base sequence, using pCR2.1-TOPO (Invitrogen), TA cloning was performed, and the obtained plasmid was introduced into *Escherichia coli* DH5α competent cells. Clones harboring plasmid, in which foreign DNA fragment was inserted, were selected from colonies of ampicillin resistant transformants appearing on ampicillin-containing LB agar medium by colony PCR. For determination of the base sequence of insert DNA, sequencing reaction using ABI PRISM BigDye Terminator Cycle Sequencing FS Ready Reaction Kit (Applied Biosystems) was carried out with thermal cycler (GeneAmp PCR system model 9700 (Applied Biosystems)) in accordance with the conditions in the information attached to the product. Then the sample was analyzed with DNA sequencer, ABI PRISM 3100 Genetic Analyzer (Applied Biosystems).

As a result, from PCR product, a sequence of structure gene having homology to novel 329 amino acids shown by SEQ ID NO: 7, i.e, TGR5, which consists of the base sequence of 990 bases represented by SEQ ID NO: 8, was determined. A novel G protein-coupled receptor protein containing the sequence shown by SEQ ID NO: 7 was designated rTGR5.

Next, the DNA fragment inserted into pCR2.1-TOPO was digested with enzyme at the sites of restriction enzymes SalI and SpeI, which were added to primer 3 and primer 4. The DNA fragment having the excised sequence of rTGR5 was inserted into SalI and SpeI sites of expression plasmid pAKKO1.11H (Hinuma, S., Hosoya, M., Ogi., Tanaka, H., Nagai, Y., and Onda, H. (1994) Biochim. Biophys. Acta 1129, 251–259), and the plasmid was inroduced to *Escherichia coli* DH5α competent cells. Clones harboring plasmid, in which rTGR5 fragment was inserted, were selected from colonies of ampicillin resistant transformants appearing on ampicillin-containing LB agar medium by colony PCR. Further, the transformant was designated *Escherichia coli* DH5α/pAKKO1.11H-rTGR5.

Example 6

Cloning of the cDNA Encoding the TGR5 Protein from Bovine Spleen cDNA by PCR Method, and Determination and Acquisition of the Base Sequence Using bovine spleen cDNA as a template, primer bF represented by SEQ ID NO: 17 and primer bR represented by SEQ ID NO: 18, amplification by PCR was performed.

The reaction solution comprised of 1 μl of cDNA solution, 0.5 μl of bF (10 μM), 0.5 μl of bR (10 μM), 2.5 μl of 10×reaction solution attached, 2.5 μl of dNTPs (10 mM), 0.5 μl of Advantage 2 DNA Polymerase (CLONTECH) and 17.5 μl of distilled water to the enzyme to make the total volume 25 μl. The PCR reaction was carried out using Thermal Cycler 9600 by heating of 95° C. for 2 minutes, then a cycle set to include 98° C. for 10 seconds followed by 63° C. for 20 seconds and 72° C. for 60 seconds, which was repeated 30 times. Using a portion of the PCR product, an amplification of the PCR product consisting of about 1000 bp was confirmed by electrophoresis. Then, the PCR product was purified using Qiagen PCR Purification Kit (QIAGEN). Directly the sequencing was done, and a sequence shown in SEQ ID NO: 13, was obtained. An amino acid sequence deduced from the DNA sequence shown in SEQ ID NO: 13, was shown in SEQ ID NO: 14. Subsequently, the PCR product recovered from the gel was subcloned into *Escherichia coli* JM109 using the TA Cloning Kit (Invitrogen) to get *Escherichia coli* JM109/pTAbTGR5-1. From *Escherichia coli* obtained by subcloning, plasmid pTAbTGR5-1 was extracted with plasmid extraction instrument (Kurabo). A base sequence of inserted fragment was determined and was confirmed to be a bovine TGR5 gene.

Example 7

Cloning of the cDNA Encoding the TGR5 Protein from Rabbit Spleen cDNA by PCR Method, and Determination and Acquisition of the Base Sequence Using rabbit spleen cDNA as a template, primer rabbitF represented by SEQ ID NO: 19 and primer rabbitR represented by SEQ ID NO: 20, amplification by PCR was performed.

The reaction solution comprised of 1 μl of cDNA solution, 0.5 μl of rabbitF (10 μM), 0.5 μl of rabbitR (10 μM), 2.5 μl of 10×reaction solution attached, 2.5 μl of dNTPs (10 mM), 0.5 μl of Advantage 2 DNA Polymerase (CLONTECH) and 17.5 μl of distilled water to. the enzyme to make the total volume 25 μl. The PCR reaction was carried out using Thermal Cycler 9600 by heating of 95° C. for 2 minutes, then a cycle set to include 98° C. for 10 seconds followed by 63° C. for 20 seconds and 72° C. for 60 seconds, which was repeated 30 times. Using a portion of the PCR product, an amplification of the PCR product consisting of about 1000 bp was confirmed by electrophoresis. Then, the PCR product was purified using Qiagen PCR Purification Kit (QIAGEN). Directly the sequencing was done, and a sequence shown in SEQ ID NO: 15, was obtained. An amino acid sequence deduced from the DNA sequence shown in SEQ ID NO: 15, was shown in SEQ ID NO: 16. Subsequently, the PCR product recovered from the gel was subcloned into *Escherichia coli* JM109 using the TA Cloning Kit (Invitrogen) to get *Escherichia coli* JM109/pTArabbitTGR5-1. From *Escherichia coli* obtained by subcloning, plasmid pTArabbitTGR5-1 was extracted with plasmid extraction instrument (Kurabo). A base sequence of inserted fragment was determined and was confirmed to be a rabbit TGR5 gene.

Example 8

Figure 9:
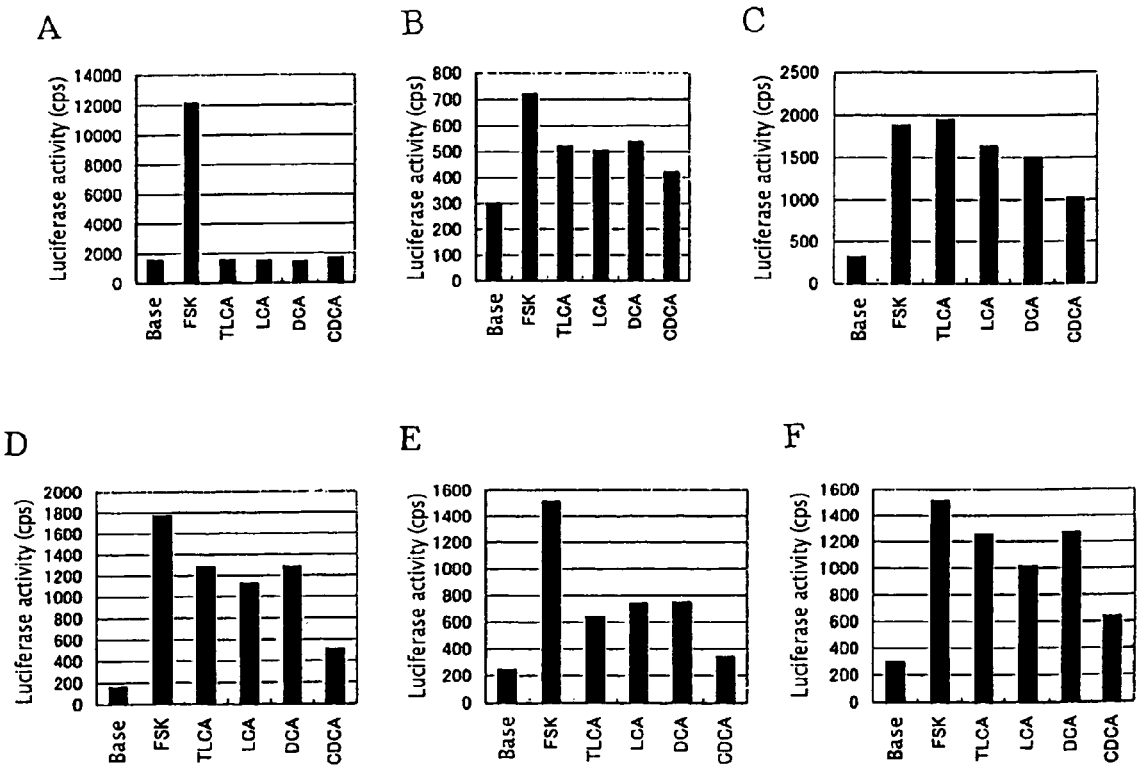
FIG. 9 shows an elevation of expression level of the reporter gene by stimulation of human (B), rabbit (C), bovine (D), mouse (E) and rat (F) TGR5 by bile acid. Bile acid was added to the medium to be 10 µM. "A" represents a control (only plasmid).

Detection of Increase of the Expression Level of Reporter Gene by Stimulation of Human, Rabbit, Bovine, Mouse and Rat TGR5 with Bile Acid Using the similar method to that shown in EXAMPLE 1, by inserting mouse and rat TGR5 gene shown in EXAMPLE 5, bovine TGR5 gene shown in EXAMPLE 6 and rabbit TGR5 gene shown in EXAMPLE 7 into an expression vector for animal cells, pAKKO-111H, the expression vectors for respective genes were prepared. According to the method shown in EXAMPLE 4, using the above vectors, an original vector inserted no fragment and the expression vector for human TGR5 shown in EXAMPLE 1, with suppressive G protein a subunit (Gi) and the reporter plasmid, protein was transiently expressed in CHO-Mock cells. Then, according to the method in EXAMPLE 3, an expression level of reporter gene by stimulation of bile acid was detected. As bile acid, taurolithocholic acid (TCLA), lithocholic acid (LCA), deoxycholic acid (DCA) and chenodeoxycholic acid (CDCA) were used at 10 μM. For a positive control of reporter gene expression, forskolin (FSSK, 2 μM) was used. Where TGR5 derived from any animal was expressed in a group with bile acid, higher luciferase activity than that of a group with no bile acid (Base) was detected (FIG. 9). From this result, it was shown that rabbit, bovine, mouse and rat TGR5 as well as human TGR5 act as a receptor for bile acid.

Example 9

Figure 10:
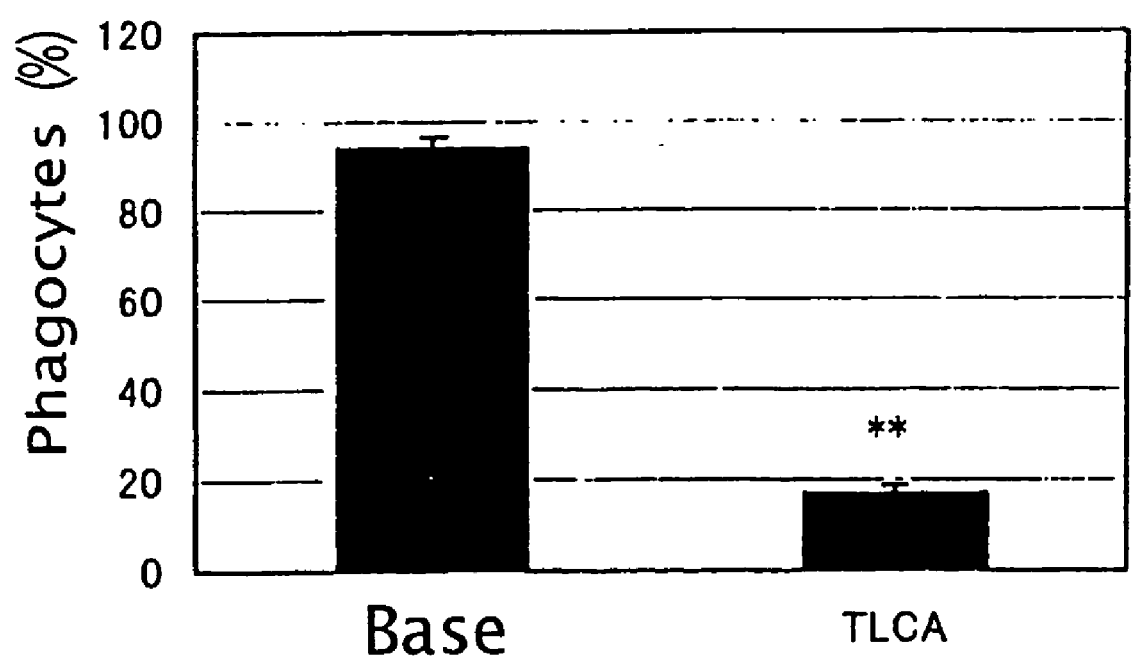
FIG. 10 shows an inhibitory effect of TLCA (100 µM) for phagocyte of rabbit alveolar macrophage. It represents a mean value of n=3. **, significance p<0.01.

Inhibitory Effects of Taurolithocholic Acid (TLCA) Against Phagocytotic Activity of Rabbit Alveolus Macrophage From rabbit (NZW, female, approximately 2.5 to 3.0 kg of weight), under anesthesia, serum and lung were collected. By washing with PBS (phosphate-buffered saline) transfused through trachea, suspension containing alveolus macrophage in the lung was recovered. After washing the obtained cells with further PBS, the cells were suspended in medium (DMEM supplemented with 2% FBS, 0.1 mM non-essential amino acids, 50 μg/ml streptomycin, 50 U/ml penicillin and 50 μg/ml gentamicin; any component from GibcoBRL), loaded on Ficoll-Paque Plus (Amersham Pharmacia), isolator for mononuclear cells, and treated with centrifugation to remove erythrocyte. After washing the mononuclear cells with the medium, the cells were seeded on 24-well plate at the concentration of $0.25 \times 10^6$/well and cultured at 37° C. under 5% $CO_2$ for overnight. After removal of the medium, 0.5 ml each of a medium supplemented with 100 μM TLCA and a control medium were added to the cells. Then the cells were further cultured for 16 hours. Fifty μl of serum obtained from the same rabbit, and $0.8 \times 10^8$/ml of yeast suspension sterilized by heating, were added to the culture. Subsequently, the cell were cultured under 5% $CO_2$ for 40 minutes. After adding 60 μl of 0.1% fuchsin solution (Wako Pure Chemicals) to the culture, the cells were peeled and were centrifuged. The suspension was observed by microscope. Utilizing the fact that the yeast is stained with fuchsin, but not the yeast eaten by alveolus macrophage, number of macrophage exhibiting a phagocytoticactivity was estimated. Accordingly, as shown in FIG. 10, in the case of TLCA addition, it was perceived that a phagocytotic activity, which is one of the immunological functions of macrophage, significantly reduced.

Example 10

Figure 11:
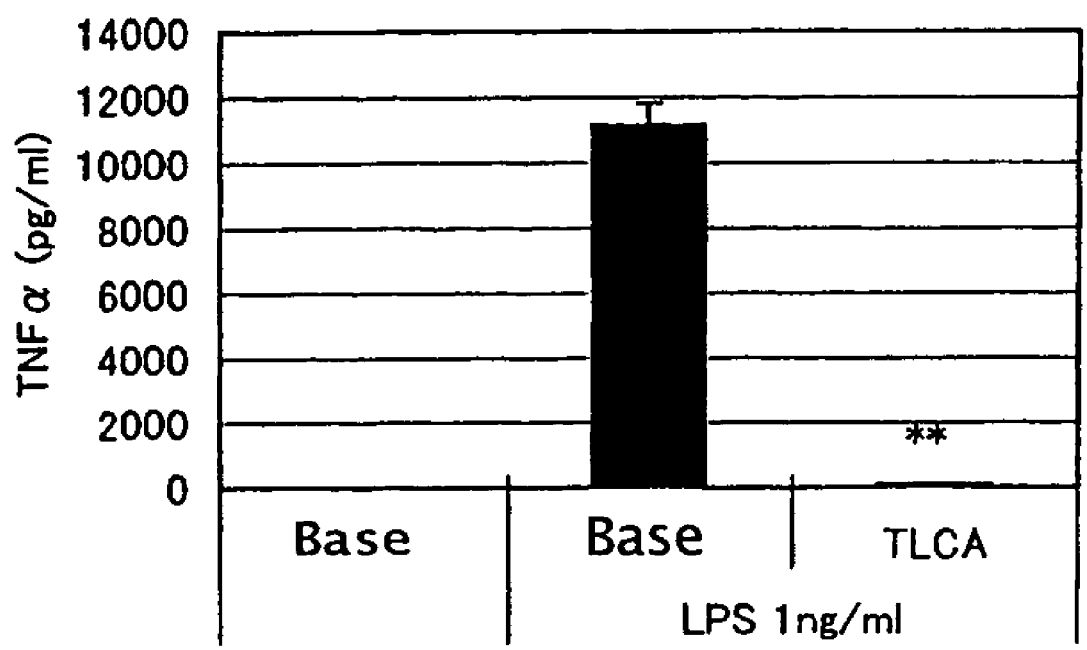
FIG. 11 shows an inhibitory effect of TLCA (50 µM) for secretion of tumor necrosis factor (TNF) α induced by lipopolysaccharide (LPS) in rabbit alveolar macrophage. It represents a mean value of n=3. **, significance p<0.01.

Inhibitory Effects of TLCA Against Secretion of Tumor Necrosis Factor (TNF)α that was Induced by Lipopolysaccharide (LPS) in Rabbit Alveolus Macrophage Rabbit alveolus macrophage collected by the method of EXAMPLE 9 was diluted to the concentration of $0.25 \times 10^6$/well and cultured in 24-well plate for overnight. Then the effects against secretion of TNFα that is induced by stimulation of LPS were investigated. After replacing the medium with 0.5 ml of the medium containing 50 μM TLCA or the medium for control, the cells were cultured for 1 hour. Then 0.5 ml of the medium containing the same concentration as described above of TLCA supplemented with LPS (*E. coli* O111:B4, Wako Pure Chemicals) or the medium for control supplemented with LPS wherein the concentration at the time of addition was 1 ng/ml, was added to the culture, and was further cultured at 37° C. under 5% $CO_2$ for 12 hours. After cultivation, the supernatant was recovered. Then using growth inhibitory function against TNF sensitive cell line L929 (RIKEN Institute) as an index, a level of TNFα was measured. L929 cells were seeded on 96-well plate at $2 \times 10^4$/well and cultured at 37° C. under 5% $CO_2$ for overnight. Subsequently, supernatant containing alveolus macrophage was appropriately diluted and cultured in the presence of 2 μg/ml actinomycin D (Wako Pure Chemicals) for overnight. As a standard sample, human recombinant TNFα (Genzyme) was used. The growth of L929 cells was measured with Cell Counting Kit-8 (Wako Pure Chemicals). As shown in FIG. 11, it was perceived that by addition of TLCA, secretion level of TNFα was significantly decreased.

Example 11

Figure 12:
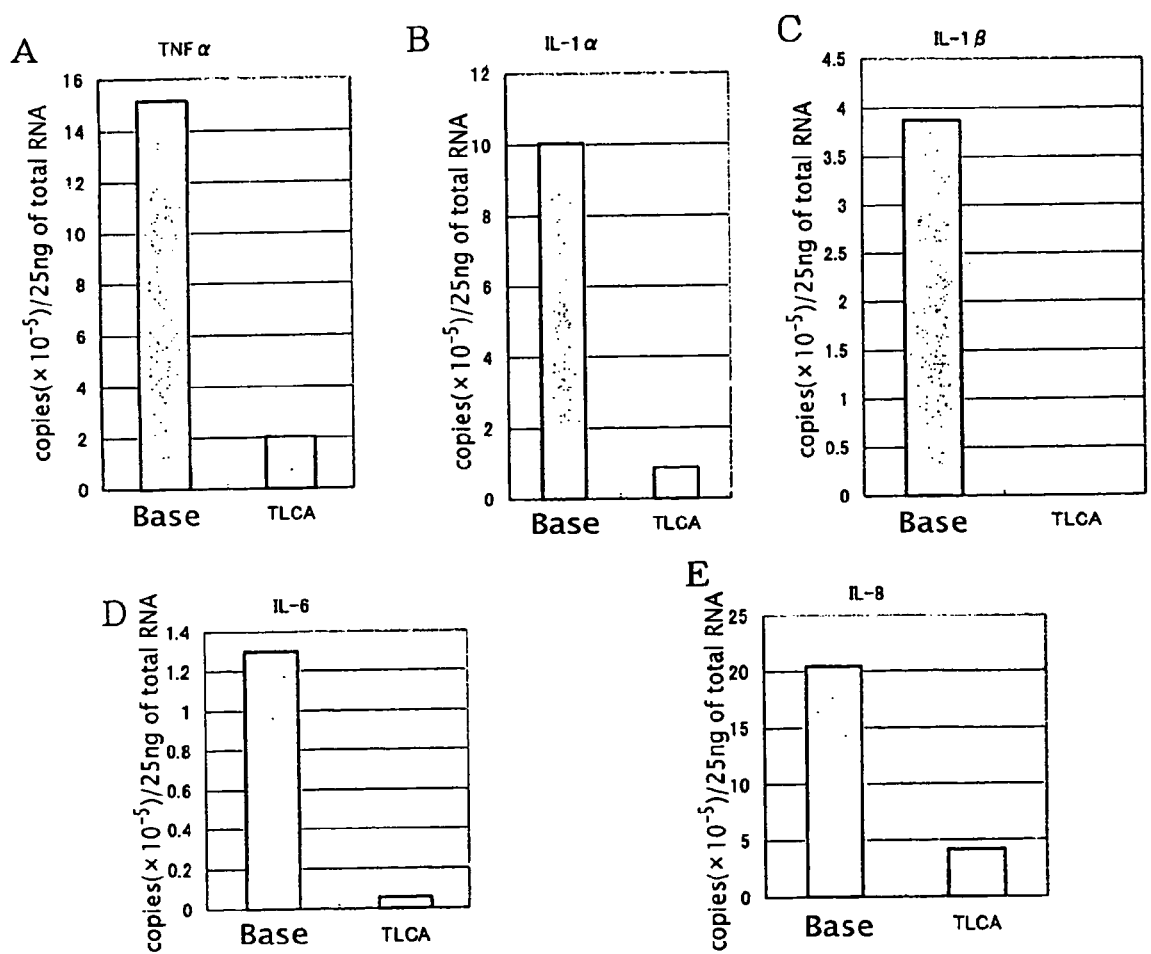
FIG. 12 shows an inhibitory action of TLCA for rabbit alveolar macrophage on the expression of various cytokine mRNA. The symbol represents as fllows: A: TNFα; B: IL-1α; C: IL-1β; D: IL-6; E: IL-8.

Inhibitory Action of Taurolithocholic Acid (TLCA) Against an Expression Level of Various Cytokine mRNA in Rabbit Alveolus Macrophage Rabbit alveolus macrophage collected by the method of EXAMPLE 9 was diluted to the concentration of $0.25 \times 10^6$/ well and cultured in 6-well plate for overnight. After replacing the medium with 1.5 ml of the medium containing 100 μM TLCA or the medium for control, the cells were cultured for 1 hour. Then 1.5 ml of the medium containing the same concentration as described above of TLCA supplemented with LPS (*E. coli* O111:B4, Wako Pure Chemicals) or the medium for control supplemented with LPS wherein the concentration at the time of addition was 1 ng/ml, was added to the culture, and was further cultured at 37° C. under 5% $CO_2$ for 2 hours. After removing the medium and adding 3 ml of Isogen (Nippon Gene), in accordance with the manual, total RNA was prepared. From 1 μg of total RNA, using SuperScriptII reverse transcriptase (GibcoBRL), in accordance with the manual, cDNA was synthesized. Then cDNA corresponding to 25 ng of total RNA/μl was prepared. An expression level of various cytokine mRNA was quantified using ABI prism 7700 Sequence Detector (ABI). In each reaction, primers and probes specific to each cytokine represented by SEQ ID NOs: 21 through 35 were designed and used. The reaction solution comprised of 12.5 μl of Universal PCR master mix (ABI), 0.225 μl each of primers (100 μM), 1.25 μl of 5 μM probe, 1 μl of cDNA solution prepared described above and distilled water to make the total volume 25 μl. In each sample, the reaction for quantification was performed as the following conditions: 50° C. for 2 minutes, 95° C. for 10 minutes and a cycle set to 95° C. for 15 seconds and 60° C. for 1 minute, which is repeated 40 times. As a result, in any cytokine among TNFα, IL-1α, IL-1β, IL-6 and IL-8, the expression level was apparently decreased by addition of TLCA. Thereby, inhibitory action of expression for various cytokine mRNA against rabbit alveolus macrophage with TLCA was found (FIG. 12).

Example 12

Preparation of THP-1 Cells, in which TGR5 Gene is Introduced

By Introducing TGR5 gene into human macrophage cell line THP-1, TGR5 highly expressed cells were established. Firstly, pcDNA-TGR5, which human TGR5 cDNA was incorporated into pcDNA3.1 (Invitrogen), was prepared according to the ordinary method. THP-1 was cultured in medium (RPMI 1640/10% FBS), and pcDNA-TGR5 was introduced using Lipofectamine (GibcoBRL) in accordance with the ordinary method. Thereafter, by addition of G418 (GibcoBRL), resistant strain was selected. Then the cell line THP-TGR5, in which TGR5 is stably and highly expressed, was established.

Example 13

Inhibitory Effects of TLCA Against Levels of Secretion and mRNA Expression of Tumor Necrosis Factor (TNF)α, which were Induced by Lipopolysaccharide (LPS) in THP-TGR5

Figure 13:
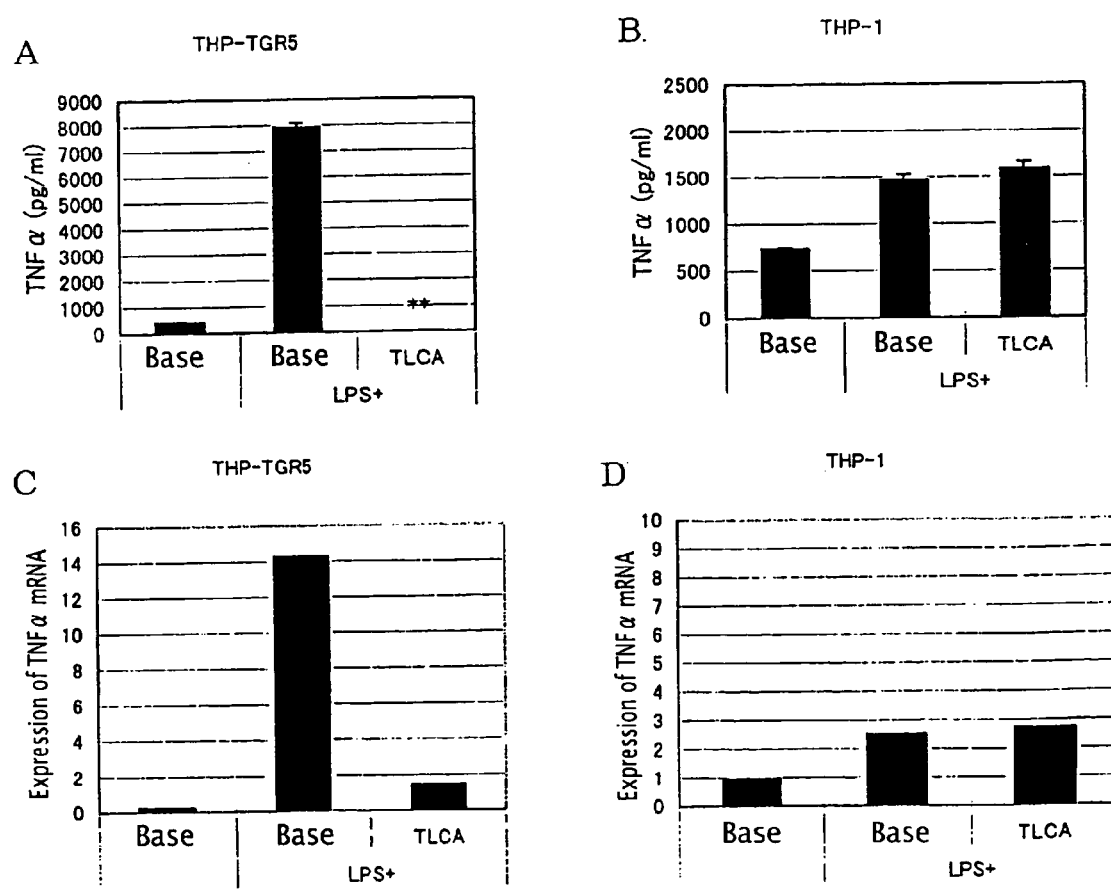
FIG. 13 shows an inhibitory effect of TLCA (100 µM) for secretion of tumor necrosis factor (TNF) α induced by lipopolysaccharide (LPS) in THP-TGR5. Secretion level represents a mean value of n=3. **, significance p<0.01. Expression level of mRNA represents a mean value of n=2.

THP-TGR5 obtained in EXAMPLE 12 or original THP-1 was diluted to the concentration of $0.5 \times 10^6$/well, and cultured on 24-well plate in the presence of $10^{-8}$ M phorbol ester (Wako Pure Chemicals) for overnight. Then affection against TNFα secretion induced by LPS stimulatiion was studied. Using the medium supplemented with 100 μM TLCA, or 0.5 ml of control medium, the cells were cultured for 1 hour. Then 0.5 ml of LPS, which is added to the medium containing the same concentration of TLCA or the control medium (the concentration at the time of addition is 50 ng/ml), was added to the culture, and the cells were cultured at 37° C. under 5% $CO_2$ for 24 hours. After cultivation, the supernatant was recovered. In the similar way to that of EXAMPLE 10, contents of TNFα was quantified by growth inhibitory activity of L929. Total RNA from THP-1 and THP-TGR5was prepared from the cells after 2 hours of LPS addition in the same method as that of EXAMPLE 11. The expression level of human TNFα mRNA was measured using TaqMan Cytokine Gene Expression plate I (ABI). As shown in FIG. 13, in the THP-TGR5, significant decrease of TNFα secretion level by TLCA addition was perceived. On the other hand, in the original THP-1, no significant inhibitory action of TNFα secretion was observed. For mRNA, significant decrease of expression level was also perceived. From these results, it was confirmed that inhibitory effects against TNFα secretion, which was observed in rabbit alveolus macrophage, is mediated by TGR5. Thus, it was indicated that in vivo, TGR5 is linked to the control of such immunological functions.

Example 14

Intracellular Translocation of TGR5-GFP Fusion Protein, which is Expressed in CHO Cells, by Addition of Taulithocholic Acid Expression plasmid wherein fusion protein that cDNA encoding Green Fluorescent protein (GFP) isolated from Aequorea coerulescens was ligated to the C-terminus of TGR5 by adjusting a translation frame, was constructed. As GFP cDNA, a fragment excised from GFP-expressing vector pQBI25 (Takara Shuzo) was used. The stop codon of TGR5 was corrected to the recognition sequence of restriction enzyme NheI by the PCR method. GFP fragment was ligated to the terminus, and the obtained fragment was inserted into the expression vector pAKKO-111H described in EXAMPLE 1. The thus obtained plasmid, which is an expression vector for fusion protein of TGR5 and GFP (hereinafter referred to as TGR5-GFP) was transfected to CHO-mock cells by the following method. The CHO-mock cells were suspended in growth medium (DMEM (Dulbecco's Modified Eagle Medium) (GIBCO BRL) supplemented with 10% fetal bovine serum (GIBCO BRL)), seeded on Lab-Tek II coverglass chamber (Nalgen Nunc), which has 4 chambers, at the concentration of $0.6 \times 10^5$ cells/chamber. After cultivation at 37° C. in the presence of 5% $CO_2$ for overnight, transfection was carried out. For transfection, Lipofectamine™ 2000 Reagent (GIBCO BRL) was used. Firstly, 2 μl of Lipofectamine™ 2000 Reagent and 50 μl of OPTI-MEM-I (GIBCO BRL) were admixed and stood for 20 minutes at room temperature to form a complex of DNA with lipofectamine. Then 100 μl of the above CHO cells were added to the cultured chamber. The culture was further performed at 37° C. in the presence of 5% $CO_2$ for overnight. The medium was replaced with the medium for confocal microscopic observation (Hanks' Balanced Salt Solution (GIBCO BRL) supplemented with 0.1% bovine albumin (essentially Fatty Acid Free, GIBCO BRL). Then with confocal microscope (Leica), fluorescent image of GFP was observed. In this case, the excitation of GFP was performed at 488 nm.

Figure 14:
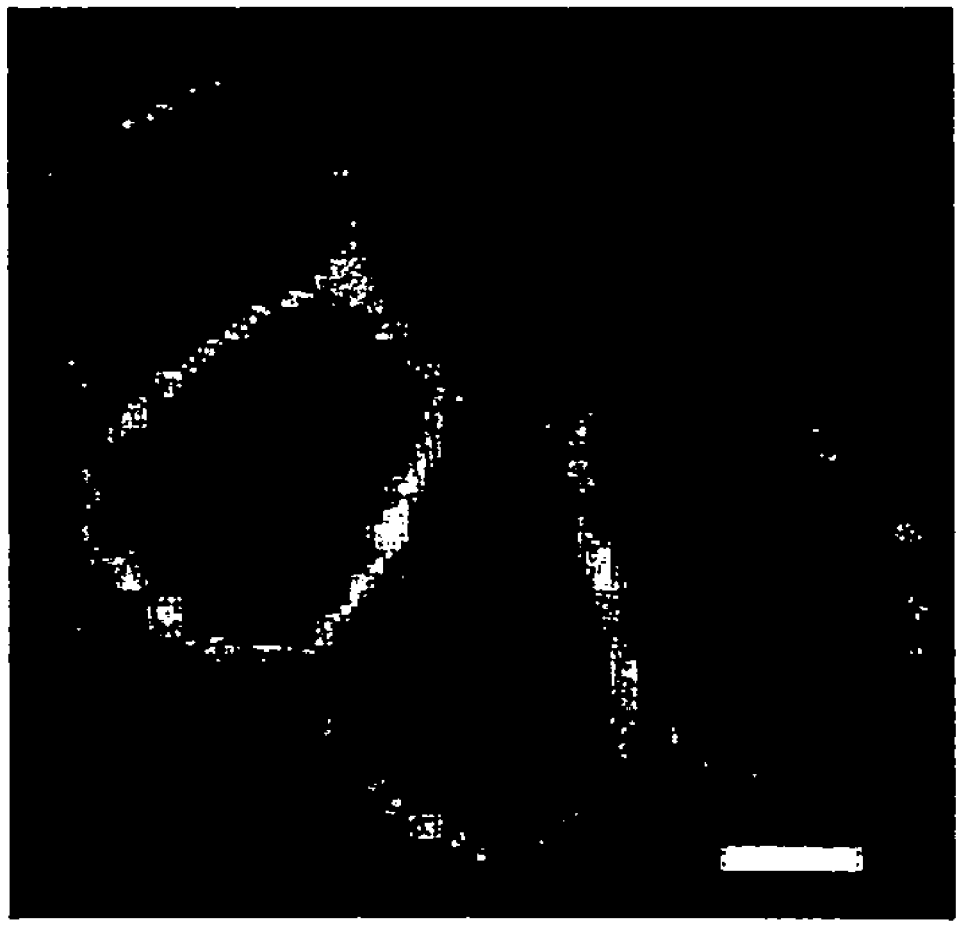
FIG. 14 shows a localization of TGR5-GFP fused protein expressed in CHO cells. White bar in the figure shows 4 µm.
Figure 15:
FIG. 15 shows a localization of the fused protein at 30 minutes after addition of TLCA in CHO cells, in which TGR5-GFP has been expressed. White bar in the figure shows 4 µm.

As a result, TGR5-GFP fusion protein was observed in cell membrane (FIG. 14). 30 minutes after addition of taurolithocholic acid to the medium to be $10^{-5}$ M, the GFP fluorescence was not found in cell membrane. It was found that the fluorescence was translocated to cytoplasm (FIG. 15). This fact indicated that TGR5 is a G protein-coupled receptor, which is expressed in cell membrane and translocates to cytoplasm by reaction with taurolithocholic acid, i.e, internalizes.

Example 15

Figure 16:
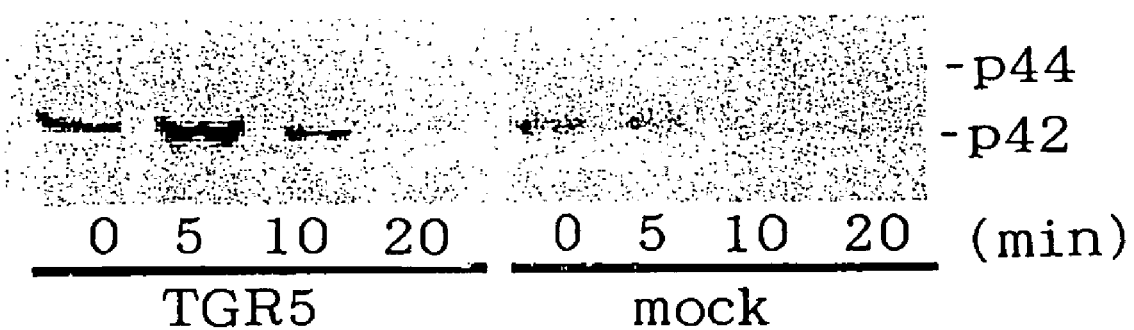
FIG. 16 shows detection for activation of MAP kinase in CHO-TGR5 by TLCA.

Activation of MAP Kinase in TGR5 Expressing CHO Cells by Addition of Taurolithocholic Acid TGR5 stably expressing CHO (CHO-TGR5) cells, which were prepared by the publicly known method using TGR expressing vector that was prepared in EXAMPLE 1, or CHO-mock cells were seeded on 6-well plate at he concentration of $3\times10^5$/well, and cultured for overnight with low serum medium (no nucleic acid containing MEMα supplemented with 0.5% dialyzed fetal bovine serum). Further, the medium was replaced with seum-free medium (no nucleic acid containing MEMα supplemented with 0.1% bovine serum albumin), and the cells were cultured for overnight. The medium was replaced with fresh serum-free medium and the culture was continued for 3 hours. Then 2 μM taurolithocholic acid (TLCA) was added. After incubation for 0 through 20 minutes, the cells were lysed and extracted with sample buffer (TEFCO). Subsequently, isolation by SDS-PAGE was carried out. Then, using PhosphoPlus p44/42 MAP kinase (Thr202/Tyr204) Antibody Kit (Cell Signaling Technology, Inc), Western blotting was performed. As shown in FIG. 16, in only TGR5-expressing CHO cells, it was found that activation of the protein, which is indicated by phsphorylation of MAP kinase, occurs as a peak at 5 minutes after TLCA addition.

Figure 17:
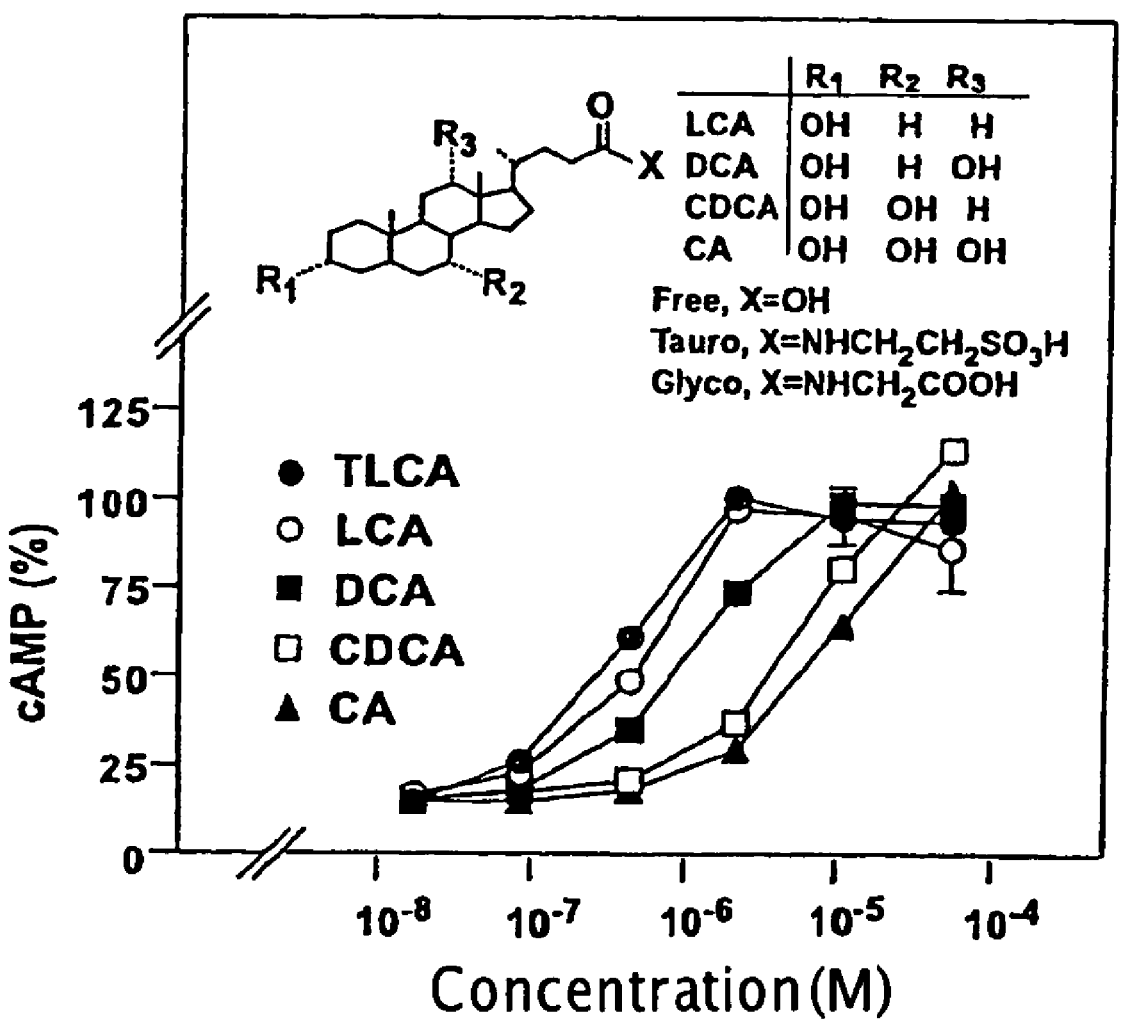
FIG. 17 shows cAMP production increasing activity by TLCA, LCA, DCA, CDCA and CA in CHO-TGR5. It represents a mean value of n=3. Structural formula in the graph represents bile acid.
Figure 18:
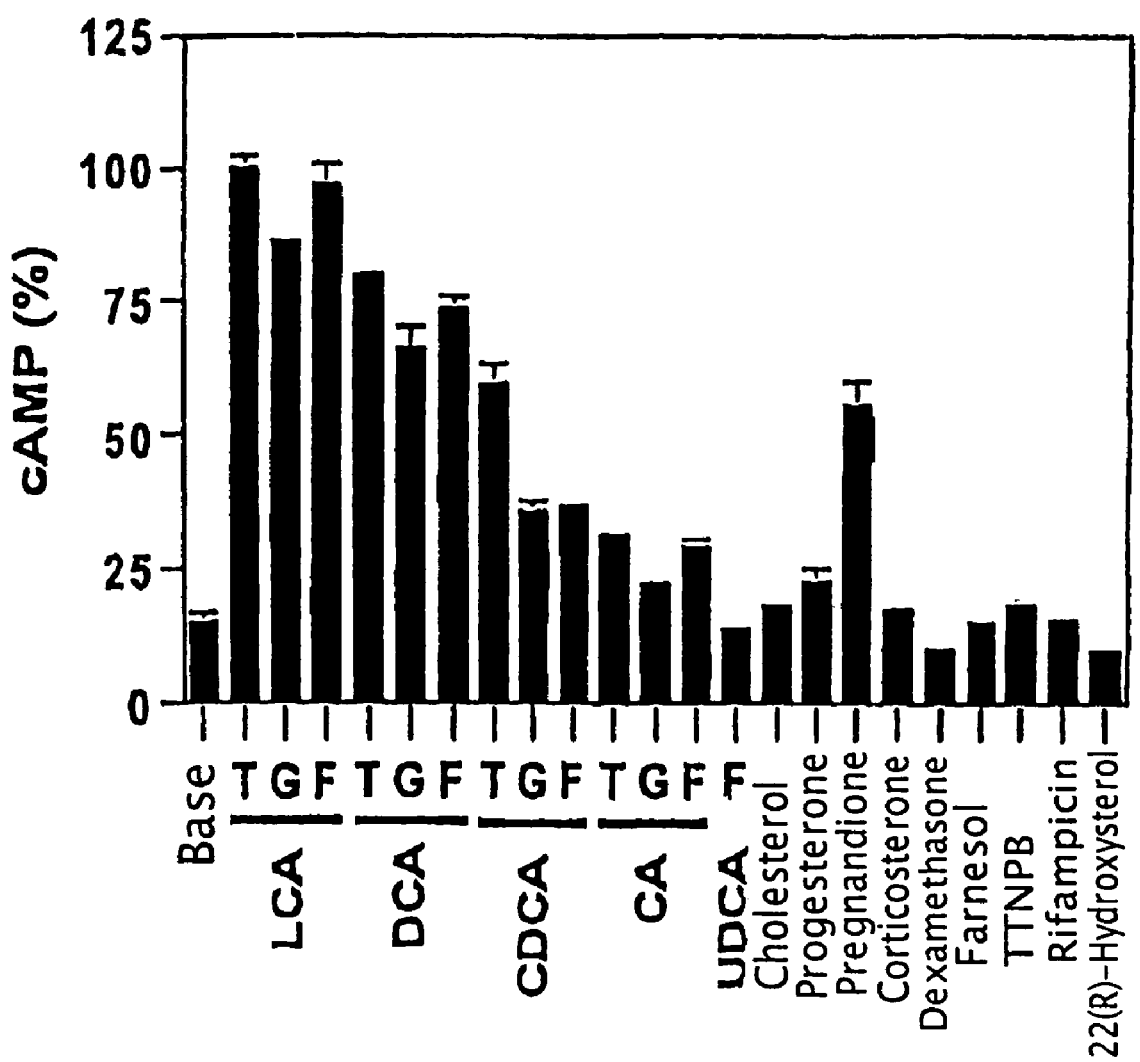
FIG. 18 shows the comparison of cAMP production increasing activity by various compounds relating bile acid (2 µM) in CHO-TGR5. It represents a mean value of n=3. TTNPB shows an abbreviation of (E)-[(tetrahydrotetramethylnaphtalenyl) propyl] benzoic acid.

Example 16 cAMP Production Increasing Activity in TGR5 Expressing CHO Cells by Various Bile Acid CHO-TGR5 cells were seeded on 96-well plate at the concentration of $2\times10^4$/well, cultured for overnight and used in the assay for cAMP production level. The cells were washed twice with assay buffer (DMEM supplemented with 0.1% bovine serum albumin and 0.2 mM 3-isobutyl-1-methylxanthine (IBMX)) and preincubated for 30 minutes. After washing the cells twice, a sample diluted with assay buffer was added to the cells, and the cells were incubated for 20 minutes. The culture supernatant was discarded, and by cAMP Screen System (ABI), cAMP production level was measured. As a positive control, 10 μM lithocholic acid was used. The cAMP production level was represented by % for positive control as 100%. As shown in FIG. 17, in order of taurolithocholic acid (TLCA), lithocholic acid (LCA), deoxycholic acid (DCA), chenodeoxycholic acid (CDCA) and cholic acid (CA), increase of cAMP production, which is dependent on concentration, was observed. The cAMP production increasing activity by other bile acids and cholesterol metabolic compound at the concentration of 2 μM in CHO-TGR5 was compared, and the result was shown in FIG. 18. In respetive cases of LCA, DCA, CDCA and CA, it was found that all of taurine inclusion body (T), glycine inclusion body (G) and non-inclusion body (F) have a cAMP production increasing activity.

Example 17

Analysis of Expression Distribution of Human TGR5 mRNA

For quantification of mRNA expression level, ABI PRISM 7700 Sequence Detector (Applied Biosystems) was used. Primers and probe used for quantification of expression level were designed based on the base sequence of human TGR5 (SEQ ID NO: 2) using software for ABI PRISM 7700 Sequence Detector, PrimerExpress (applied Biosystems). The cDNA for template was synthesized from 1 μg of polyA+ RNA derived from various human tissues using random primers at 42° C. For reverse trancription, SuperScript II reversetranscriptase (GIBCO BRL) was used. The reaction was performed in accordance with the manual attached. After completion of the reaction, the product was precipitated with ethanol and dissolved in 100 μl. For fractionated cDNA from hemocyte, Multiple Tissue cDNA (MYTC™) panels Human Blood Fractions (Clontech) was used. The reaction solution for ABI PRISM 7700 Sequence Detector consisted of, according to the manual of TaqMan Universal PCR Master Mix (Applied Biosystems), 12.5 μl of Master Mix, 0.9 μM primers, 0.25 μM probe and 1 μl of cDNA solution of each sample, and filled up to 25 μl with distilled water. The reaction for ABI PRISM 7700 Sequence Detector was done under the following conditions: 50° C. for 2 minutes, 95° C. for 10 minutes, then a cycle set to include 95° C. for 15 seconds and 60° C. for 1 minute, which is repeated 40 times.

Figure 19:
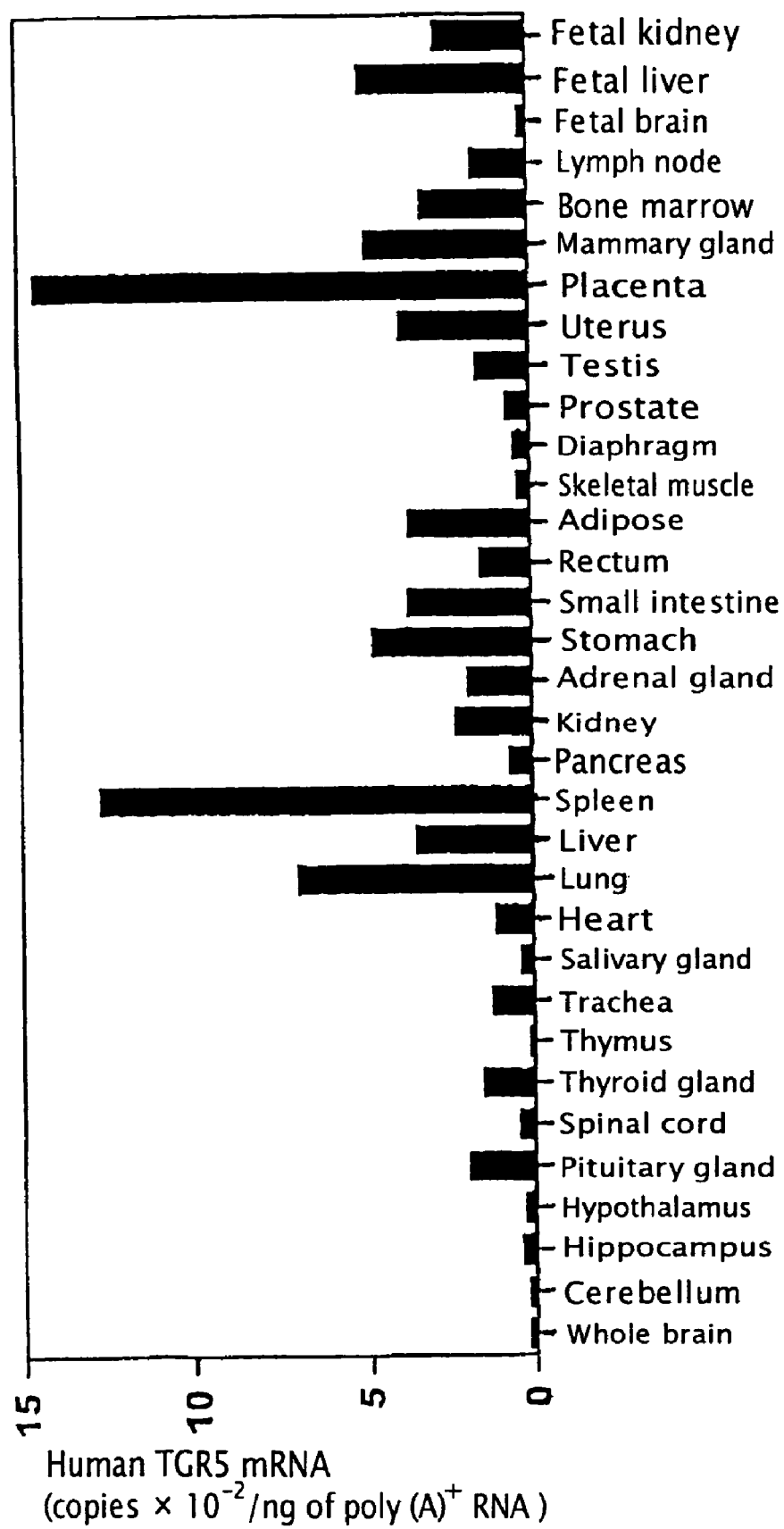
FIG. 19 shows an expression distribution of TGR5 mRNA in human tissues.
Figure 20:
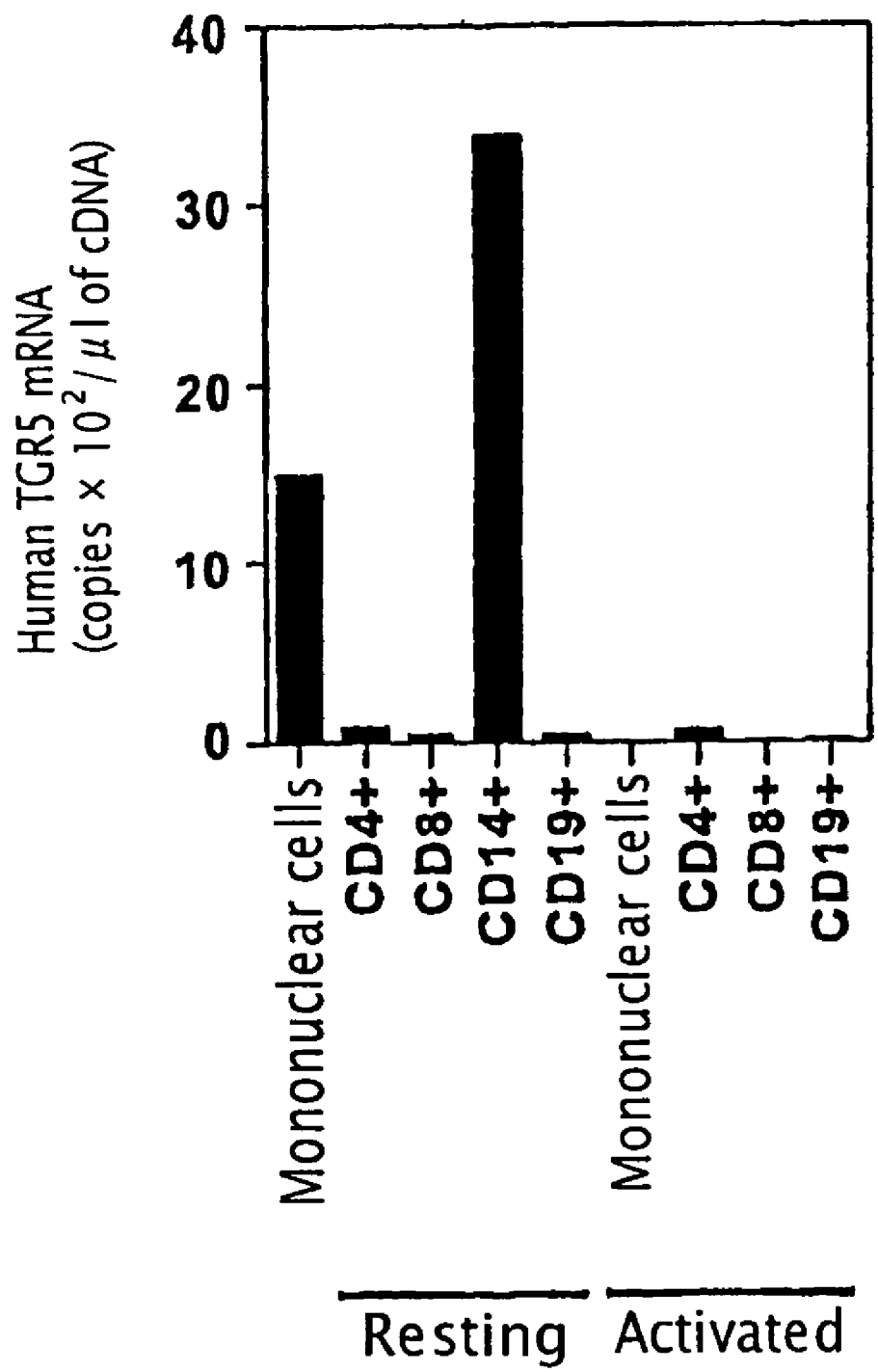
FIG. 20 shows an expression distribution of TGR5 mRNA in human blood cell.

Expression distribution of TGR5 mRNA in various human tissues was shown in FIG. 19. In tissues such as placenta, spleen and lung, which are associated with immune system, high expression was observed. In addition, an expression level of TGR5 mRNA in human hemocyte was shown in FIG. 20. In the CD14-expressing hemocyte, that is, monocyte and macrophage, high expression was found.

Example 18

Analysis of Expression Distribution of Rabbit TGR5 mRNA

In the similar method to that of EXAMPLE 17, an expression level of rabbit TGR5 mRNA was estimated. The primers and probe used were designed based on rabbit TGR5 (SEQ ID NO: 15). Total RNA derived from various tissues of rabbit was prepared by obtaining various tissues from individual of NZW purchased from Kitayama Labes, which was female weighing approximately 2.5 to 3.0 kg, and using Isogen (Nippon Gene) in accordance with the attached manual. CDNA was synthesized from 1 μg of total RNA in the similar method to that of EXAMPLE 17 except dissolution to 40 μl after reverse transcription.

Figure 21:
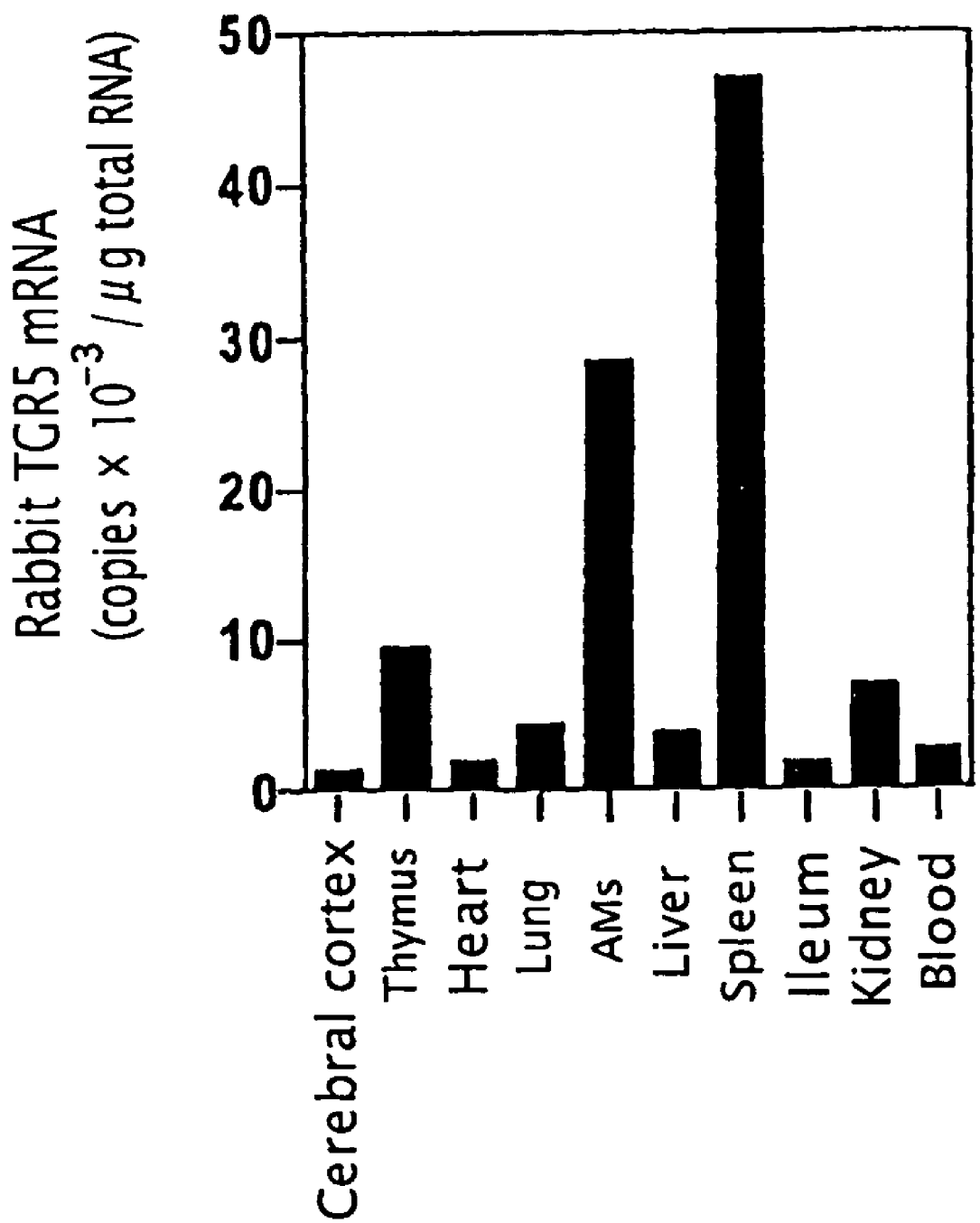
FIG. 21 shows an expression distribution of rabbit TGR5 mRNA.

Expression of rabbit TGR5 mRNA was, as shown in FIG. 21, highly observed in spleen, alveolus macrophage and thymus, which were associated with immune system.

Example 19

Increase of cAMP Production of Rabbit Alveolus Macrophage by TLCA

Figure 22:
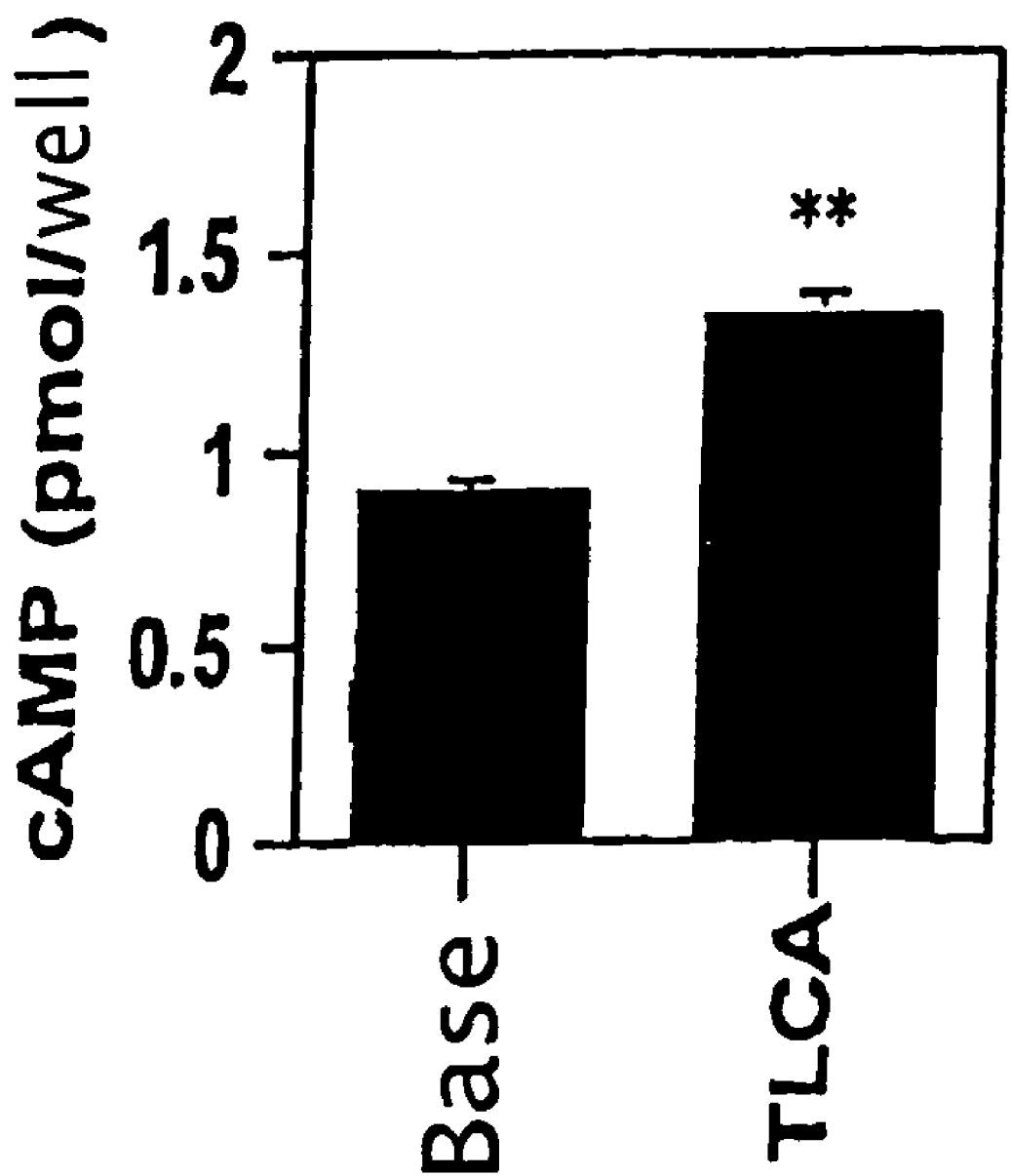
FIG. 22 shows cAMP production increasing activity of rabbit alveolar macrophage by TLCA. It represents a mean value of n=3. **, significance p<0.01.

Rabbit alveolus macrophage that was prepared by the method of EXAMPLE 9 was suspended in the medium (DMEM supplemented with 2% FBS, 0.1 mM non-essential amino acids, 50 μg/ml streptomycin, 50 U/ml penicillin and 50 μg/ml gentamicin), seeded on 96-well plate at the concentration of $2\times10^5$/well, and cultured for overnight. After washing the cells twice with the medium, that is, DMEM supplemented with 0.1% BSA and 1 mM IBMX, 200 μM TLCA diluted with the same medium, or the medium was added to the cells. Then incubation for 4 minutes was carried out. With cAMP Screen System (ABI), a level of cAMP production was measured. From the result, it was perceived that as shown in FIG. 22, a level of cAMP production was increased by addition of TLCA.

Example 20

Figure 23:
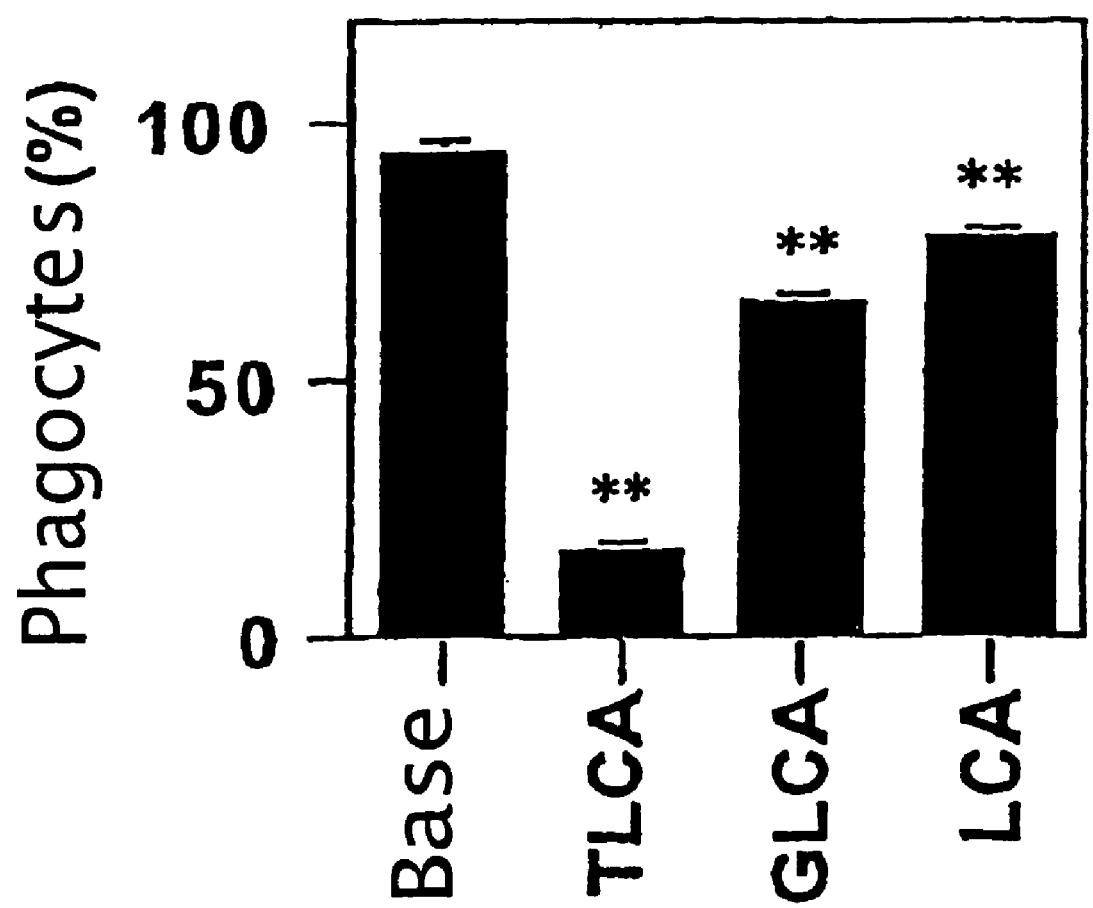
FIG. 23 shows an inhibitory effect of various bile acids for phagocyte of rabbit alveolar macrophage. It represents a mean value of n=3. **, significance p<0.01.

Inhibitory Effects of Various Bile Acids, which Affect to a Phagocytotic Activity of Rabbit Alveolus Macrophage According to the method of EXAMPLE 9, rabbit alveolus macrophage was prepared. Then using this, inhibitory effects against phagocytic ability by various bile acids were investigated. As shown in FIG. 23, in the case of GLCA and LCA as well as TLCA, which were added at the concentration of 100 µM, it was perceived that a phagocytotic activity, which is one of the immunological functions in macrophage, was significantly decreased.

Example 21

Figure 24:
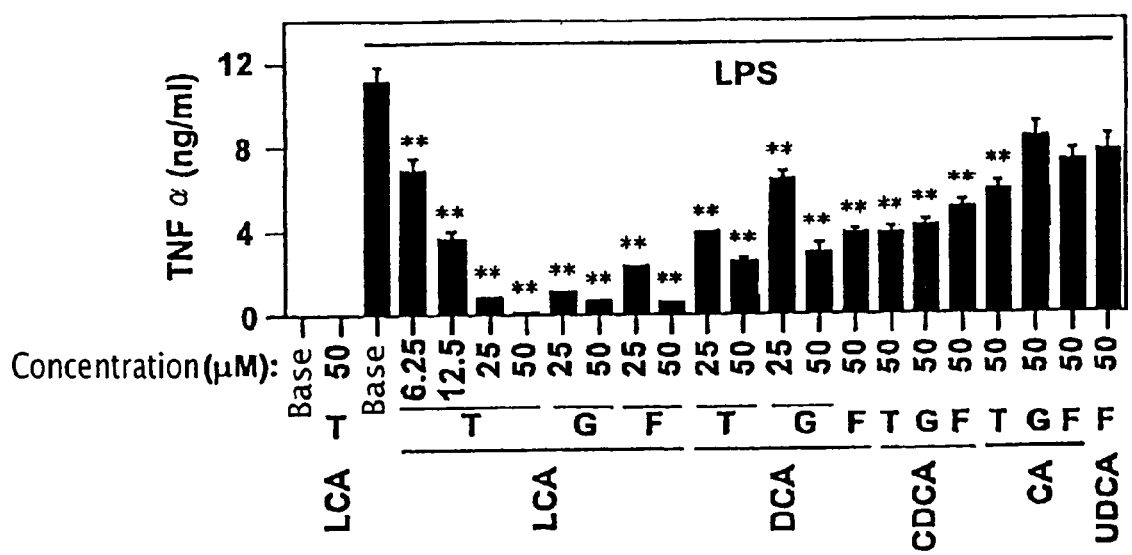
FIG. 24 shows an inhibitory effect of various bile acids for secretion of TNFα from rabbit alveolar macrophage. It represents a mean value of n=3. **, significance p<0.01.

Inhibitory Effects of Bile Acid Against Secretion of TNFα from Rabbit Alveolus Macrophage Rabbit alveolus macrophage that was prepared by the method of EXAMPLE 9 was suspended in the medium (DMEM supplemented with 2% FBS, 0.1 mM non-essential amino acids, 50 µg/ml streptomycin, 50 U/ml penicillin and 50 µg/ml gentamicin), seeded on 24-well plate at the concentration of $0.25 \times 10^6$/well, and cultured for overnight. Bile acid diluted with the same medium was added to alveolus macrophage at the concentration depicted in graph. Then the macrophage was cultured for 1 hour. Further, bile acid sample having the same concentration, which was supplemented with lipopolysaccharide (LPS, E. coli O111:B4, Wako Pure Chemicals), was added. Then the culture was done for further 12 hours. The concentration of LPS was 1 ng/ml. After cultivation, the supernatant was collected, and TNFα in the supernatant was quantified in the same manner as that in EXAMPLE 10. As shown in FIG. 24, by addition of bile acid, which exhibits an agonist activity for TGR5, an inhibitory activity on TNFα secretion, which is dependent on the concentration, was perceived.

Example 22

Increase of cAMP Production in THP-1 Cells, in which TGR5 Gene is Introduced

Figure 25:
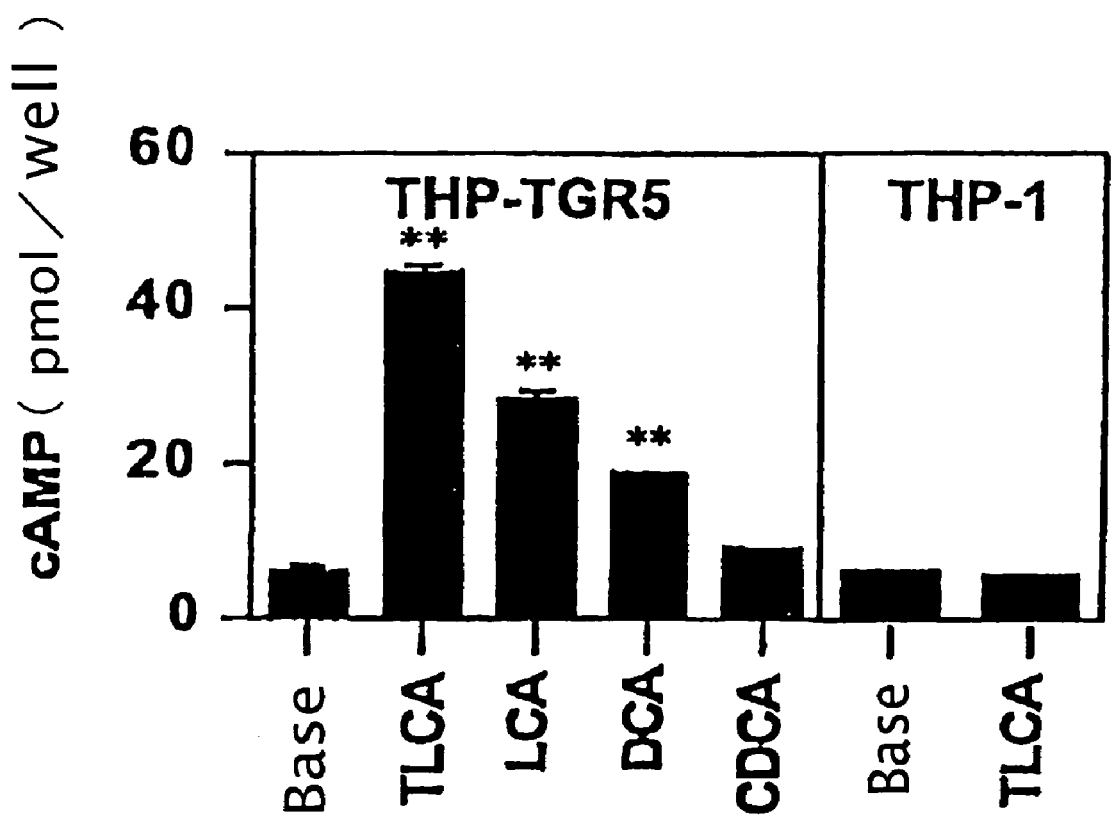
FIG. 25 shows increase of cAMP production by addition of bile acid in THP-TGR5 cells. It represents a mean value of n=3. **, significance p<0.01.

After washing THP-1 or TGR5 highly expressing cell line THP-TGR5 obtained in EXAMPLE 12 with the medium for assay (DMEM supplemented with 0.1% BSA and 1 mM IBMX), the cells were seeded on 96-well plate at $1 \times 10^5$/well. Bile acid, which was diluted by the medium for assay described above, was added to the cells. Then the cells were incubated for 20 minutes. Subsequently, with cAMP Screen System (ABI), a level of cAMP production was assayed. As shown in FIG. 25, in THP-TGR5, increase of cAMP production by addition of TLCA, LCA and DCA was observed. On the other hand, in THP-1, increase of cAMP production by addition of TLCA was not observed. Therefore, it was confirmed that increase of cAMP by these bile acids is mediated by TGR5.

Example 23

Inhibitory Effects of Various Bile Acids Against Secretion of Tumor Necrosis Factor (TNF)α from LPS-Stimulated THP-TGR5

Figure 26:
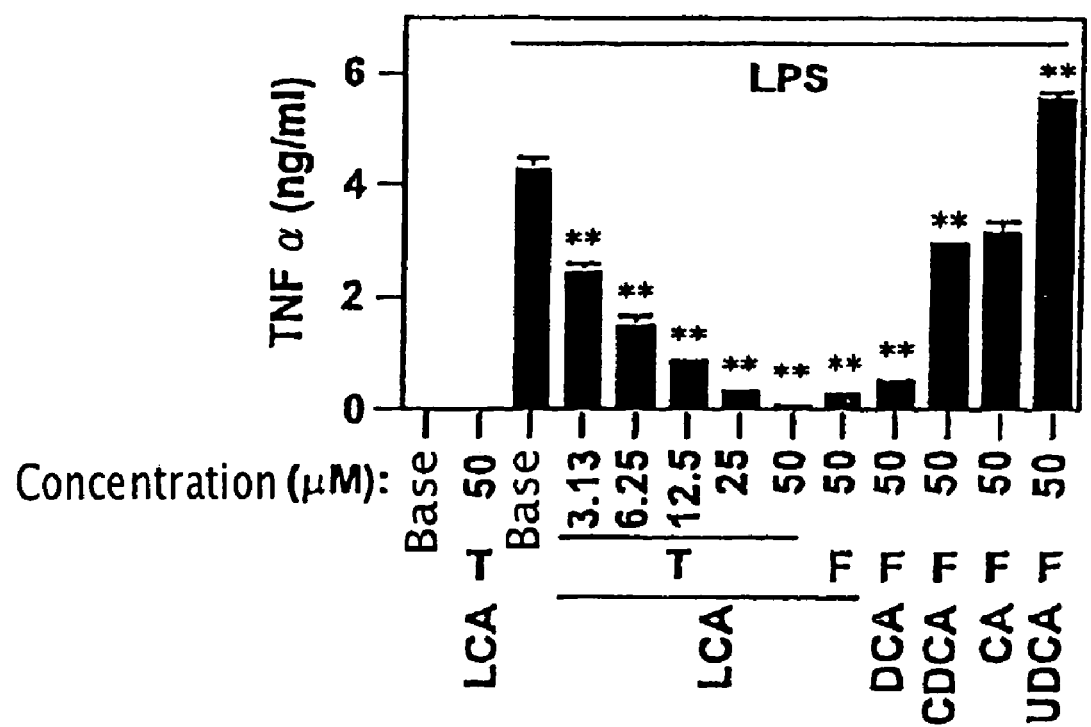
FIG. 26 shows an inhibitory effect of various bile acids for secretion of tumor necrosis factor (TNF) α from THP-TGR5 stimulated by LPS. It represents a mean value of n=3. **, significance p<0.01.
Figure 27:
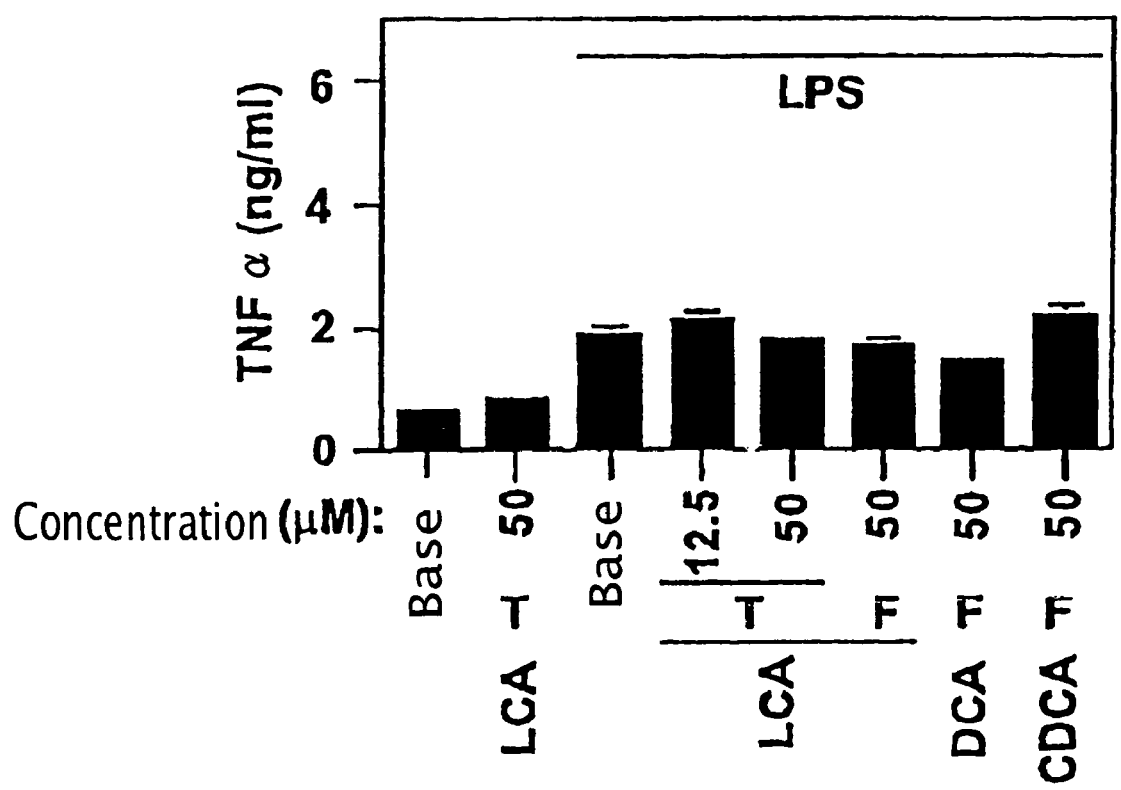
FIG. 27 shows an effect of various bile acids for secretion of tumor necrosis factor (TNF) α from THP-1 stimulated by LPS. It represents a mean value of n=3.

THP-TGR5 or THP-1 cells was treated in the same manner as that of EXAMPLE 13, and inhibitory effects of various bile acids against secretion of TNFα from LPS stimulation was investigated. Duration for LPS stimulation was 12 hours. After recovery of culture supernatant, as well as EXAMPLE 13, TNFα contents were measured by bioassay. As shown in FIG. 26, in THP-TGR5, it was perceived that a level of TNFα secretion was reduced in the manner dependent on the concentration of bile acid. On the other hand, in THP-1, significant inhibitory action against TNFα secretion was not observed (FIG. 27). From these results, it was confirmed that inhibitory effects against TNFα secretion, which was observed in rabbit alveolus macrophage, is mediated by TGR5. Thus, it was indicated that in vivo, TGR5 is linked to the control of such immunological functions.

Reference Example 1

Amplification of Human GPR7 DNA Using Human Chromosomal DNA by PCR Method

Using the human chromosomal DNA as a template and two synthetic primers (SEQ ID NO: 42 and SEQ ID NO: 43), DNA amplification by PCR was carried out. The synthetic primers were constructed to allow a region of the gene to be translated to the receptor protein to amplify. Therewith, at the 5' end of the gene, the base sequence recognized by restriction enzyme ClaI was added, and at the 3' end, the base sequence recognized by restriction enzyme SpeI was added. The reaction solution in the above reaction comprised of 0.5 µg of human chromosomal DNA, 1 µM each of synthetic DNA primers, 0.8 mM dNTPs, 1 mM $MgCl_2$, 1 µl of KOD Polymerase (TOYOBO) and a buffer attached to the enzyme to make the total volume 50 µl. The cycle for amplification was carried out using a thermal cycler (PE Biosystems) by heating of 94° C. for 60 seconds, then a cycle set to include 98° C. for 15 seconds followed by 65° C. for 2 seconds and 74° C. for 30 seconds, which was repeated 35 times. The amplified product was confirmed by 0.8% agarose gel electrophoresis follwed by ethidium bromide staining.

Reference Example 2

Subcloning of PCR Product into a Plasmid Vector and Confirmation of the Amplified DNA by Decoding the Base Sequence of the Insert DNA Portion Using the PCR reaction solution in Reference Example 1, DNA was isolated by 0.8% low melting agarose gel electrophoresis. The DNA band was excised from the gel with razor, and was recovered by crashing the pieces of agarose, phenol extraction, phenol-chroloform extraction and ethanol precipitation. In the manner prescribed in PCR-Script™ Amp SK(+) Cloning Kit (Stratagene), the recovered DNA was subcloned to plasmid vector pCR-Script Amp SK(+). After transformation of *Escherichia coli* DH5α competent cell (TOYOBO) by introducing the above-mentioned vector, clones harboring cDNA insert fragment was selected on LB agar medium containing ampicillin, IPTG and X-gal. All the white-colored clones were isolated with sterilized toothpick, and then the transformant *E. coli* DH5α/GPR7 was obtained. Respective clones were cultured in LB medium containing ampicillin for overnight. Subsequently, the plasmid DNA was prepared using QIAwell 8 Plasmid Kit (Qiagen). A portion of the prepared DNA was cleaved with the restriction enzymes ClaI and SpeI, and a size of the receptor cDNA fragment inserted was confirmed. The reaction for determination of the base sequence was carried out using DyeDeoxy Terminator Cycle Sequence Kit (Applied Biosystems). As a result, after decoding with the fluorescent automated sequencer, the DNA sequence was obtained (SEQ ID NO: 39). The plasmid pCR-Script Amp SK(+) harboring DNA having the base sequence represented by SEQ ID NO: 39 was designated pCR-Script human GPR7. The amino acid sequence of human GPR7 encoded by DNA having the base sequence represented by SEQ ID NO: 39 was shown as SEQ ID NO: 38. In the DNA sequence of human GPR7, which the sequence was determined herein, 2 bases were diferrent from the DNA sequence reported by O'Dowd et al. (O'Dowd, B. F. et al., Genomics 28: 84–91 (1995)). These bases correspond to the $893^{rd}$ and $894^{th}$ nucleotides of the sequence represented by SEQ ID NO: 39, wherein respective nucleotides are C and G in the report by O'Dowd et al., and G and C in the present reference example. From this result, in the amino acid sequence translated, the 296th amino acid residue of the sequence represented by SEQ ID NO: 38 is Thr in the report by O'Dowd et al., and Ser in the present reference example.

Reference Example 3

Acquisition of GPR7 Ligand Precursor Gene from Human Whole Brain cDNA by PCR Method and Construction of Expression Vector Using the human whole brain cDNA purchased from Clontech as a template and the following two synthetic primers, amplification by PCR was carried out.

```
                                         (SEQ ID NO: 40)
GSF1:  5'-GTCGACATGGCCCGGTCCGCGACACTGGCGGCC-3'

(SEQ ID NO: 41)
GSR2:  5'-GCTAGCAGCGGTGCCAGGAGAGGTCCGGGCTCA-3'
```

The reaction solution comprised of 1 µl of cDNA solution, 0.5 µl of GSF1 (10 µM), 0.5 µl of GSR2 (10 µM), 2.5 µl of 10×reaction solution attached, 2.5 µl of dNTPs (10 mM), 0.5 µl of KlenTaq (Clontech) and 17.5 µl of Ohtsuka distilled water to make the total volume 25 µl. The PCR reaction was carried out using Thermal Cycler 9600 by heating of 95° C. for 2 minutes, then a cycle set to include 98° C. for 10 seconds followed by 60° C. for 20 seconds and 72° C. for 20 seconds, which was repeated 35 times. Using a portion of the PCR product, an amplification of the PCR product consisting of about 400 bp was confirmed by electrophoresis. Then, the PCR product was purified using QIAGEN PCR Purification Kit. Directly the sequencing was done, and a sequence shown in FIG. 28 (SEQ ID NO: 37) was obtained. An amino acid sequence deduced from the DNA sequence shown in FIG. 28 was shown in FIG. 29 (SEQ ID NO: 36). Subsequently, the PCR product recovered from the gel was subcloned into *Escherichia coli* JM109 using the TA Cloning Kit (Invitrogen) to get *Escherichia coli* JM109/pTAhGPR7-1. From *Escherichia coli* obtained by subcloning, plasmid pTAhGPR7-1 was extracted with plasmid extraction instrument (Kurabo). A base sequence of inserted fragment was determined and was confirmed to be a human GPR7 ligand cDNA identical to that shown in FIG. 28. Then, from the plasmid, after digestion by restriction enzymes SalI and NheI, about 0.4 kb of human GPR7 ligand cDNA fragment was obtained. Further, a vector region of the expression vector for animal cells, pAKKO-111H was recovered by digestion of restriction sites, i.e. SalI site and NheI site in the multicloning site, and electrophoresis. The human GPR7 ligand cDNA fragment prepared as described above and expression vector were ligated by ligation. *Escherichia coli* JM109 was transformed with this plasmid to obtain *E. coli* JM109/pAK-S64.

Transformant *Escherichia coli* JM109/pAK-S64 was cultured for preparation of pAK-S64 plasmid DNA in large quantities.

Reference Example 4

Transient Expression of GPR7 Expressing Plasmid and Reporter Plasmid in Chinese Hamster Ovary (CHO) Cells Using a plasmid, which human GPR7 DNA obtained in REFERENCE EXAMPLE 3 was inserted to the expression plasmid for animal cells, pAKKO-111H, *Escherichia coli* JM109 was transformed. After isolating and culturing the obtained colony, a GPR7 expressing plasmid DNA was prepared using QIAGEN Plasmid Maxi Kit (QIAGEN). The pCRE-Luc plasmid DNA (Clontech), to which luciferase gene was ligated as a reporter gene downstream cAMP response element (CRE), was prepared in the similar way.

The GPR7 expressing plasmid and pCRE-Luc were transiently expressed in CHO cells, in which an expression plasmid inserted no receptor gene was introduced. In 100 µl of culture fluid, CHO cells were seeded on 96-well plate (Corning Coaster) at 40,000 cells/well, and cultured at 37° C. for overnight. For a culture on the plate, DMEM (Dulbecco's modified Eagle's medium, GibcoBRL) only supplemented with 10% fetal bovine serum was used.

Each plasmid was diluted to 240 ng/µl. Nine µl of GPR7 expressing plasmid and 1 µl of pCRE-Luc were added to 240 µl of Opti-MEM-I. This was mixed with equal volume of the solution, in which 10 µl of Lipofectamine 2000 was added to 240 µl of Opti-MEM-I to form a complex with liposome and plasmid DNA according to the method described in the manual attached to Lipofectamine 2000. This solution was added to the CHO cell culture at 25 µl/well. Four hours later, culture fluid was replaced with assay buffer (DMEM supplemented with 0.1% fetal bovine serum) to be serum-free, and the solution was incubated at 37° C. for overnight.

Reference Example 5

Expression of Ligand Gene in CHO Cells

The expression plasmid for animal cells, pAK-S64, in which human ligand cDNA prepared in REFERENCE EXAMPLE 4 was inserted, was transiently expressed in CHO cells in the similar manner to that of REFERENCE EXAMPLE 5. The cells were seeded on 6-well plate (Falcon) at 600,000 cells/well and cultured for overnight. Then the plasmid haboring ligand gene was introduced. Ten µl of plasmid, which is diluted to 240 ng/µl, was added to 240 µl of Opti-MEM-I. This was mixed with equal volume of the solution, in which 10 µl of Lipofectamine 2000 was added to 240 µl of Opti-MEM-I to form a complex with liposome and plasmid DNA according to the method described in the manual attached to Lipofectamine 2000. This solution was added to the CHO cell culture at 500 µl/well. Four hours later, culture fluid was replaced with assay buffer to be serum-free. Eighteen hours after replacement of medium, the medium in each well was recovered, thereby supernatant of CHO cell culture containing ligand peptide was obtained.

Example 24

Detection of Ligand Activity by Reporter Assay

Figure 30:
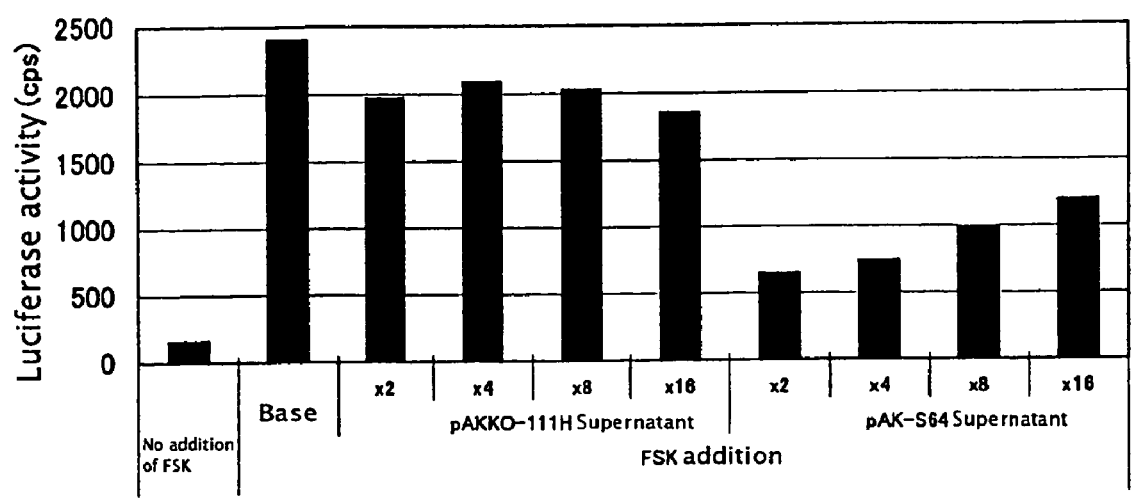
FIG. 30 shows the result of detection for inhibition of luciferase activity by stimulation of ligand when culture supernatant of CHO cells, in which ligand expressing vector pAK-S64 and expression vector with no insert (pAKKO-111H) was expressed, was added to medium of CHO cells, in which expression plasmid wherein GPR7 cDNA was inserted, was transiently expressed, with Fforskolin (FSK).

The culture supernatant prepared in Reference Example 5, in which pAK-S64 was expressed, and forskolin at 2 µM of final concentration were added to the culture fluid of CHO cells, in which GPR7 was transiently expressed following the method of Reference Example 4. The culture supernatant of CHO cells, in which the expression vector (pAKKO-111H) with no insertion of ligand gene was transiently expressed by the method of Reference Example 5, was also added in the same way. At that time, the supernatant, in which the expression was observed, was diluted double, 4-fold, 8-fold and 16-fold with assay buffer. For 4 hours after addition of the supernatant, incubation was performed at 37° C., enhancement or inhibition of transcription and/or translation of reporter (luciferase) gene derived from intracellular signal transduction, which was raised by an agonist activity of ligand mediated by receptor, was introduced. After incubation, the assay buffer in each well was removed, and 50 µl of luminescent substrate for PicaGene LT2.0 (Toyo Ink) were added to each well. The cells were lysed, and the cell lysate was fully mixed with the substrate. Then luminescence derived from the expression induction level of reporter gene in the well was measured using plate reader (ARVOsx multilabel counter, Perkin Elmer). As a result, only when the culture supernatant of pAK-S64 was added, inhibition of expression for reporter gene was detected as reduction of luciferase activity (FIG. 30). Further, the level of inhibition was dependent on the concentration of the culture supernatant of pAK-S64. This fact indicates that intracellular signal was transduced through GPR7 by the product expressed by the plasmid that inserted to pAK-S64. That is, it shows that GPR7 acted as a ligand.

INDUSTRIAL APPLICABILITY

By using a screening method/kit of the invention, compounds that alter the binding property between a novel G protein-coupled receptor protein, its partial peptide or salts thereof, and a substance relating to cholesterol metabolism as a ligand, or salts:thereof are obtained. The compounds or salts thereof can be used as medicines for prophylaxis and/or therapy for central diseases (e.g, Alzheimer's disease, dementia, eating disorder), inflammatory diseases (e.g, allergy, asthma, rheumatism), circulatory diseases (e.g, hypertension, cardiac hypertrophy, cardiac angina, arteriosclerosis), cancer (e.g, non-small-cell lung cancer, ovarian cancer, prostate cancer, stomach cancer, bladder carcinoma, breast cancer, cancer of uterine cervix, colon cancer, rectum cancer), diabetes, immune system diseases (e.g, autoimmune disease, immunodeficiency, leukemia), diseases of liver and cholecyst (e.g, liver cirrhosis, hepatitis, liver failure, cholestasis, calculosis), alimentary diseases (e.g, ulcer, enterisis, malabsorption), adiposis.

In the method for determining a ligand to the receptor protein, of which ligand is undetermined, a variety of cell lines can be used. Thus the method of the invention is convenient and an assay can be performed for a short time.

The invention claimed is:

1. A method of screening a compound or salts thereof that alters the binding property between a G protein-coupled receptor protein or salts thereof, and a bile acid, wherein said method comprises:
   a) contacting a labeled bile acid with the G protein-coupled receptor protein containing the amino acid sequence represented by SEQ ID NO: 1 or a protein containing an amino acid sequence having at least 90% homology to the amino acid sequence represented by SEQ NO: 1 and having the same ligand binding activity as the amino acid sequence represented by SEQ ID NO: 1 or salts thereof, and measuring the amount of said labeled bile acid bound to said G protein-coupled receptor protein or said protein or salts thereof; and
   b) contacting a labeled bile acid and a test compound with the G protein-coupled receptor protein containing the amino acid sequence represented by SEQ ID NO: 1 or a protein containing an amino acid sequence having at least 90% homology to the amino acid sequence represented by SEQ NO: 1 and having the same ligand binding activity as the amino acid sequence represented by SEQ ID NO: 1 or salts thereof, and measuring the amount of said labeled bile acid, bound to said G protein-coupled or said protein or salts thereof; and
   c) comparing binding property between a) and b).

2. A kit for screening a compound or salts thereof that alters the binding property between a G protein-coupled receptor protein or salts thereof, and a bile acid, which comprises (1) the G protein-coupled receptor protein containing the amino acid sequence represented by SEQ ID NO: 1 or a protein containing an amino acid sequence having at least 90% homology to the amino acid sequence represented by SEQ NO: 1 and having the same ligand binding activity as the amino acid sequence represented by SEQ ID NO: 1, or salts thereof, and (2) the bile acid.

* * * * *